United States Patent
Percec et al.

(10) Patent No.: US 9,623,046 B2
(45) Date of Patent: Apr. 18, 2017

(54) AMPHIPHILIC JANUS-DENDRIMERS

(75) Inventors: Virgil Percec, Philadelphia, PA (US); Andrew D. Hughes, Philadelphia, PA (US); Pawaret Leowanawat, Bangkok (TH); Daniela A. Wilson, Rotherham (GB); Christopher J. Wilson, Rotherham (GB)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/388,587

(22) PCT Filed: Aug. 5, 2010

(86) PCT No.: PCT/US2010/044520
§ 371 (c)(1),
(2), (4) Date: Aug. 13, 2012

(87) PCT Pub. No.: WO2011/017500
PCT Pub. Date: Feb. 10, 2011

(65) Prior Publication Data
US 2012/0308640 A1 Dec. 6, 2012

Related U.S. Application Data

(60) Provisional application No. 61/231,840, filed on Aug. 6, 2009.

(51) Int. Cl.
*C07C 69/78* (2006.01)
*C07D 493/10* (2006.01)
(Continued)

(52) U.S. Cl.
CPC .......... *A61K 31/74* (2013.01); *A61K 49/0028* (2013.01)
(Continued)

(58) Field of Classification Search
None
See application file for complete search history.

(56) References Cited

U.S. PATENT DOCUMENTS

2005/0019923 A1   1/2005 Uchegbu et al.
2006/0216265 A1*  9/2006 Goodman et al. ......... 424/78.27

OTHER PUBLICATIONS

Bury I, Interfacial behavior of a series of amphiphilic block co-dendrimers, 2007, Langmuir, 23, 619-625.*
(Continued)

*Primary Examiner* — Brian Gulledge
*Assistant Examiner* — Celeste A Roney
(74) *Attorney, Agent, or Firm* — Baker & Hostetler LLP

(57) ABSTRACT

The invention concerns compounds of the formula: $X—(Y)_t$ wherein: X is Formula (X), each Y is the same or different and is Formula (Y) $—O—[CH_2—CH(OH)—CH_2—O—]_m—H$; or $—C(OR^5)_3$; $R^1, R^2, R^3, R^6, R^7, R^8, R^9, R^{10}$ are each, independently, $—(CH_2CH_2O)_m—R^4$, $—[CH_2CH(OH)CH_2O]_nH$, $OR^{11}$, $—O(CH_2)_pR^{13}$, or $—(CH_2)R^{12}$; each $R^4$ is independently $OR^5$ or OH; $R^5$, $R^{11}$ and $R^{12}$ are each, independently, H or $C_1$-$C_{30}$ alkyl; $R^{13}$ is $—NH_3^+Cl^-$ or —NHBoc; t is an integer from 2 to 6; m, n, and p are each, independently, an integer from 1 to 12; and each q, r, and s is 0 or 1 and the sum of q+r+s is at least 2.

(Continued)

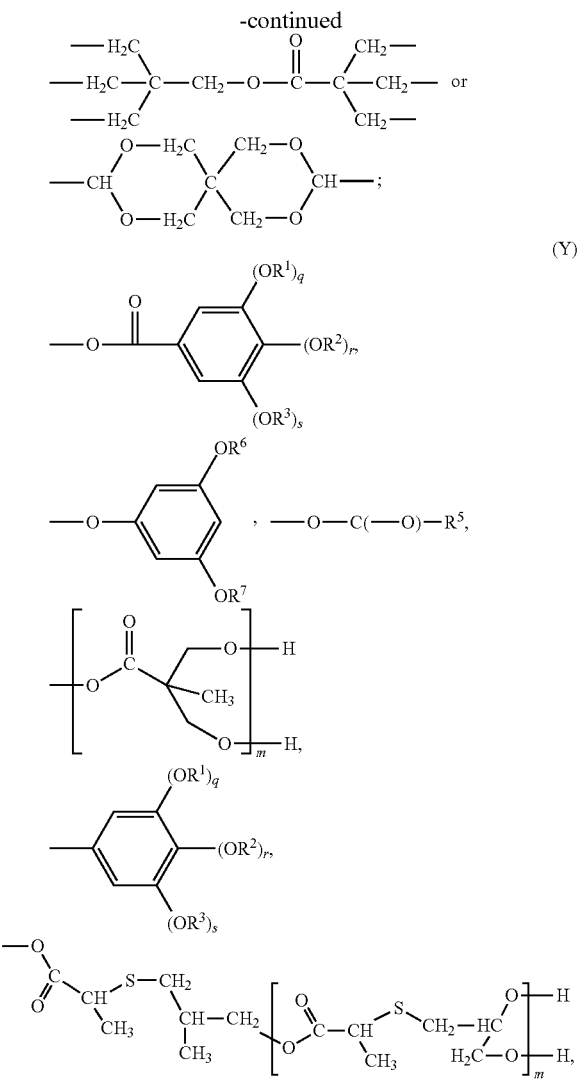

20 Claims, 6 Drawing Sheets

(51) Int. Cl.
| | | |
|---|---|---|
| C07C 69/708 | (2006.01) | |
| C07C 215/50 | (2006.01) | |
| A61K 9/127 | (2006.01) | |
| A61K 9/133 | (2006.01) | |
| A61K 31/704 | (2006.01) | |
| A61P 35/00 | (2006.01) | |
| A61K 31/74 | (2006.01) | |
| A61K 49/00 | (2006.01) | |

(56) References Cited

OTHER PUBLICATIONS

Ropponen J, Bisfunctionalized Janus Molecules, 2004, American Chemical Society, Org Lett, 6, 15, 2495-2497.*

Al-Jamal et al., "Dendrisomes: Vesicular structures derived from a cationic lipidic Dendron", J. Pharm. Sci., Jan. 2005, 94(1), 102-113.
Almgren et al., "Cryo transmission electron microscopy of liposomes and related structures", Colloid Surf A:, Phys. Eng. Asp., Nov. 2000, 174(1-2), 3-21.
Bridson, "The preparation of liposomes using compressed carbon dioxide: strategies, important considerations and comparison with conventional techniques", J. Pharm. Pharmacol., Jun. 2006, 58(6), 775-785.
Bury et al., "Interfacial behavior of a series of amphiphillic block co-dendrimers", Langmuir, Jan. 2007, 23(2), 619-625.
Chiruvolu et al., "A phase of liposomes with entangled tubular vesicles", Science, Nov. 1994, 266(5188), 1222-1225.
Das et al., "A Nitro-Hunsdiecker Reaction: From Unsaturated Carboxylic Acids to Nitrostyrenes and Nitroarenes", Org. Lett., Sep. 2002, 4(18), 3055-3058.
Deamer et al., "Large volume liposomes by an ether vaporization method", Biochem. Biophys. Acta Biomembr., Sep. 1976, 443(3), 629-634.
Dubois et al., "Self-assembly of regular hollow icosahedra in salt-free catanionic solutions", Nature, Jun. 2001, 411(6838), 672-675.
Dumoulin, "Synthesis and Liquid Crystalline Properties of Mono-, Di- and Tri-O-alkyl Pentaerythritol Derivatives Bearing Tri-, Di- or Monogalactosyl Heads: The Effects of Curvature of Molecular Packing on Mesophase Formation", Chem. Eur. J., Jun. 2007, 13(19), 5585-5600.
Esfand et al., "Poly(amidoamine) (PAMAM) dendrimers: from biomimicry to drug delivery and biomedical applications", Drug Discov. Today, Apr. 2001, 6(8), 427-436.
Haag et al., "An approach to glycerol dendrimers and pseudo-dendritic polyglycerols", J. Am. Chem. Soc., Mar. 2000, 122(12), 2954-2955.
Hillmyer et al., "Complex phase behavior in solvent-free nonionic surfactants", Science, Feb. 1996, 271(5251), 976-978.
Huang, "Phosphatidylcholine vesicles. Formation and physical characteristics", Biochemistry, Jan. 1969, 8(1), 344-352.
Ihre et al., "Fast and Convenient Divergent Synthesis of Aliphatic Ester Dendrimers by Anhydride Coupling", J. Am. Chem. Soc., Jun. 2001, 123(25), 5908-5917.
International Search Report and Written Opinion for Application No. PCT/US2010/044520, mailed Sep. 21, 2010, 8 pages.
Klein & Shinoda, "Large-Scale Molecular Dynamics Simulations of Self-Assembling Systems", Science, Aug. 2008, 321(5890), 798-800.
Lasic et al., "A new method for the instant preparation of large unilamellar vesicles", J. Am. Chem. Soc., Feb. 1988, 110(3), 970-971.
Lasic, "Liposomes within liposomes", Nature, May 1997, 387(6628), 26-27.
Mamdouh et al., "Expression of Molecular Chirality and Two-Dimensional Supramolecular Self-Assembly of Chiral, Racemic, and Achiral Monodendrons at the Liquid-Solid Interface", Langmuir, Aug. 2004, 20(18), 7678-7685.
Monnard et al., "Preparation of Vesicles from Nonphospholipid Amphiphiles", Methods in Enzymology, 2003, 372, 133-151.
Moore, "Room temperature polyesterification", Macromolecules, Jan. 1990, 23(1), 65-70.
Mulders et al., "Synthesis of a novel amino acid based dendrimer", Tetrahedron Lett., Jan. 1997, 38(4), 631-634.
Needham, "Elastic deformation and failure of lipid bilayer membranes containing cholesterol", Biophys. J., Oct. 1990, 58(4), 997-1009.
Ouchi, "Convenient and efficient tosylation of oligoethylene glycols and the related alcohols in tetrahydrofuran-water in the presence of sodium hydroxide", Bull. Chem. Soc. Jpn., Apr. 1990, 63(4), 1260-1262.
Percec et al., "Coassembly of a Hexagonal Columnar Liquid Crystalline Superlattice from Polymer(s) Coated with a Three-Cylindrical Bundle Supramolecular Dendrimer", Chem. Eur. J., Mar. 1999, 5(3), 1070-1083.

(56) References Cited

OTHER PUBLICATIONS

Percec, "Steric Communication of Chiral Information Observed in Dendronized Polyacetylenes", J. Am. Chem. Soc., Dec. 2006, 128(50), 16365-16372.

Percec, "Tubular Architectures from Polymers with Tapered Side Groups. Assembly of Side Groups via a Rigid Helical Chain Conformation and Flexible Helical Chain Conformation Induced via Assembly of Side Groups", Macromolecules, Feb. 1996, 29(5), 1464-1472.

Ropponen et al., "Bisfuntionalized Janus molecules", Organic Letters, Jun. 2004, 6(15), 2495-2497.

Rosen, "Synthesis of dendrimers through divergent iterative thio-bromo "Click" chemistry", J. Polym. Sci. Part A: Polym. Chem., Aug. 2009, 47(15), 3931-3939.

Sindhu, "Synthesis and characterization of ferrite nanocomposite spheres from hydroxylated polymers", J. Magn. Magn. Mater., Jan. 2006, 296(2), 104-113.

Szoka, Comparative Properties and Methods of Preparation of Lipid Vesicles (Liposomes), Annu. Rev. Biophys. Bioeng., Jun. 1980, 9, 467-508.

Van Hest et al., "Polystyrene-Dendrimer Amphiphilic Block Copolymers with a Generation-Dependent Aggregation," Science, Jun. 1995, 268(5217), 1592-1595.

Wagner et al., "Liposomes produced in a pilot scale: production, purification and efficiency aspects", Eur. J. Pharm. Biopharm., Sep. 2002, 54(2), 213-219.

Walter, "Intermediate structures in the cholate-phosphatidylcholine vesicle-micelle transition", Biophys. J., Dec. 1991, 60(6), 1315-1325.

Wyszogrodzka et al., "New Approaches Towards Monoamino Polyglycerol Dendrons and Dendritic Triblock Amphiphiles," Eur. J. Org. Chem., Jan. 2008, Issue 1, 53-63.

Yang, "Barrel-stave model or toroidal model? A case study on melittin pores", Biophys. J., Sep. 2001, 81(3), 1475-1485.

\* cited by examiner

AMPHIPHILIC JANUS-DENDRIMERS

RELATED APPLICATIONS

This application is the National Stage of International Application No. PCT/US2010/044520, filed Aug. 5, 2010, which claims the benefit of U.S. Provisional Application No. 61/231,840 filed Aug. 6, 2009, the disclosures of which are incorporated herein by reference in their entireties.

TECHNICAL FIELD

The invention relates to the amphiphilic Janus-dendrimers, their production and their use.

BACKGROUND

Biological membranes are complex systems assembled from phospholipids that are stabilized by cholesterol, proteins and carbohydrates. They are equipped with machinery that includes protein channels to mediate the exchange of the cell with the environment and control electron and proton transfer. Liposomes are vesicles assembled from either natural or synthetic amphiphiles. They can mimic biological membranes, probe cell machinery, and be configured into bio-inspired technological materials for medical and other applications. The design of synthetic amphiphiles represents a formidable challenge since both natural and synthetic types generated by traditional methods, produce unstable and polydisperse liposomes that require tedious separation and stabilization. There is a need in the art for systems that avoid the tedious separation and stabilization problems of the art.

SUMMARY

In some aspects, the invention concerns compounds of the formula:

$$X—(Y)_t \quad \text{Formula I}$$

wherein:
X is

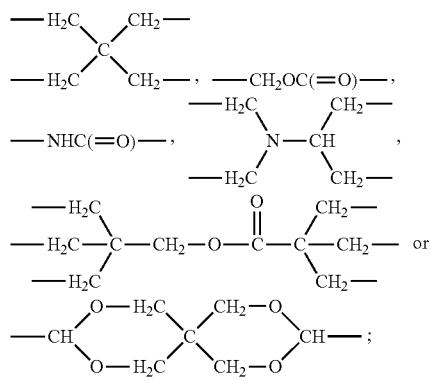

each Y is the same or different and is

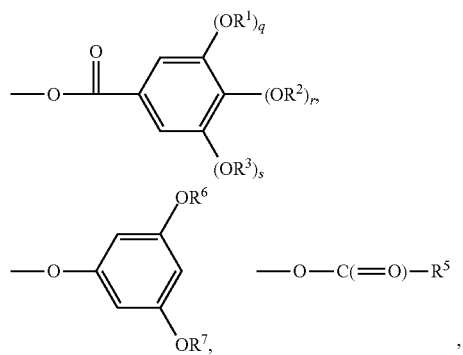

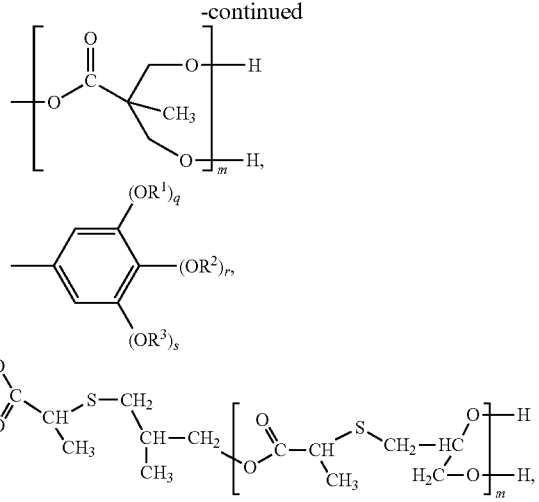

$—O—[CH_2—CH(OH)—CH_2—O—]_m—H$; or $—C(OR^5)_3$;

$R^1$, $R^2$, $R^3$, $R^6$, $R^7$, $R^8$, $R^9$, $R^{10}$ are each, independently, $—(CH_2CH_2O)_m—R^4$, $—[CH_2CH(OH)CH_2O]_nH$, $OR^{11}$, $—O(CH_2)_pR^{13}$, or $—(CH_2)_pR^{12}$;

each $R^4$ is independently $OR^5$ or $OH$;

$R^5$, $R^{11}$ and $R^{12}$ are each, independently, H or $C_1$-$C_{30}$ alkyl;

$R^{13}$ is $—NH_3^+Cl^-$ or $—NHBoc$;

t is an integer from 2 to 6;

m, n, and p are each, independently, an integer from 1 to 12;

each q, r, and s is 0 or 1 and the sum of q+r+s is at least 2;

provided that not more than one Y is of the formula $C(=O)—R^5$; and provided that Y moieties on a single compound cannot be

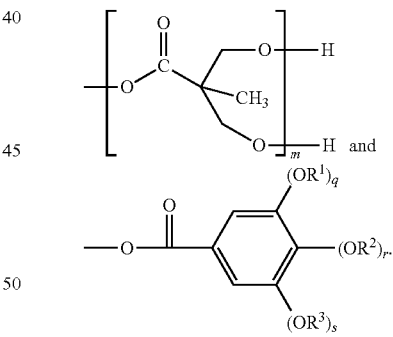

In another aspect, the invention concerns liposomes comprising the compounds described herein. One method of forming such liposomes comprises contacting a mixture of an alcohol and a plurality of compounds of claim 1 with water. In some preferred embodiments, the alcohol is ethanol.

The invention also concerns methods of delivery of therapeutic compositions utilizing the liposomes described herein. The method can comprise contacting a liposome comprising a plurality of the compounds described herein and one or more therapeutic compositions with a mammal under conditions effective to deliver said liposome to a cell or tissue within said mammal. In some preferred embodiments, the mammal is a human.

One important feature of the invention is that the compounds described herein form monodisperse and stable liposomes by simple injection of their ethanol solution into water.

DETAILED DESCRIPTION OF ILLUSTRATIVE EMBODIMENTS

The present invention concerns libraries of amphiphillic Janus-dendrimers that can self-assemble into stable, monodisperse and mechanically superior liposomes denoted dendrosomes. In some embodiments, the assembly follows simple injection of ethanol solutions into water. In contrast with polydisperse polymersome membranes assembled from block copolymer amphiphiles with limited bioresorbability, dendrosomes exhibit a host of morphologies in addition to the classic spherical shape, including the less encountered tubular, dendrosomes within dendrosomes, polygonal, dendrocubosomes and other complex architectures such as disc-like, toroidal, rod-like, polygonal, spherical, ribbon-like and helical ribbon-like dendromicelles. Initial experiments demonstrate that dendrosomes are non-toxic to cells, produce pH-sensitive membranes that deliver cancer drugs and incorporate pore forming proteins. Therefore, dendrosomes expand the precise and monodisperse primary structure of dendritic building blocks into new functions. Amphiphilic Janus-dendrimers also self-assemble in bulk and can be used to elucidate the mechanism of self-assembly of amphiphiles in the absence and presence of water. Dendrosomes are believed to extend the capabilities of synthetic amphiphiles, generating responsive membranes with permeability controllable for desirable technological applications including novel pathways for targeted drug and gene delivery, in vivo imaging, and mediation of the efficiency of enzymes and nucleic acids.

In some embodiments, the invention concerns compound of formula I. Such compounds include compounds of the formulas:

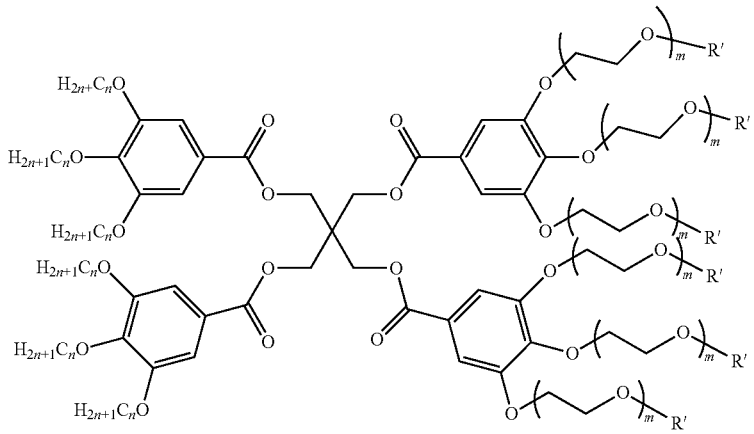

wherein R' is OH or OCH₃, and in some embodiments, where m is an integer from 1 to 6;
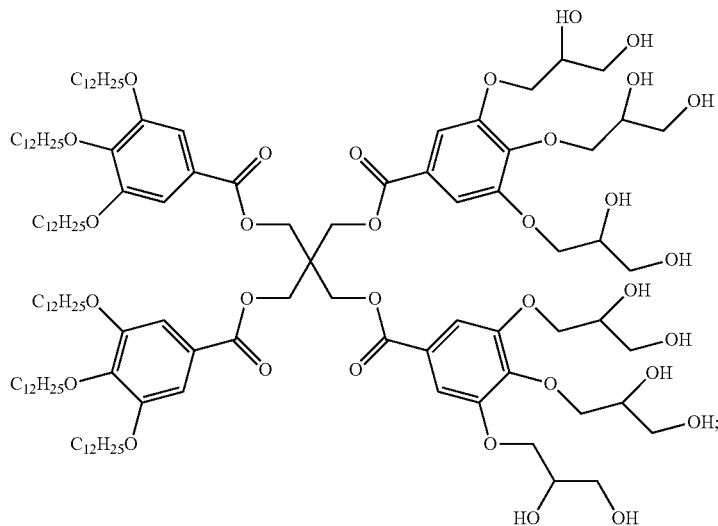
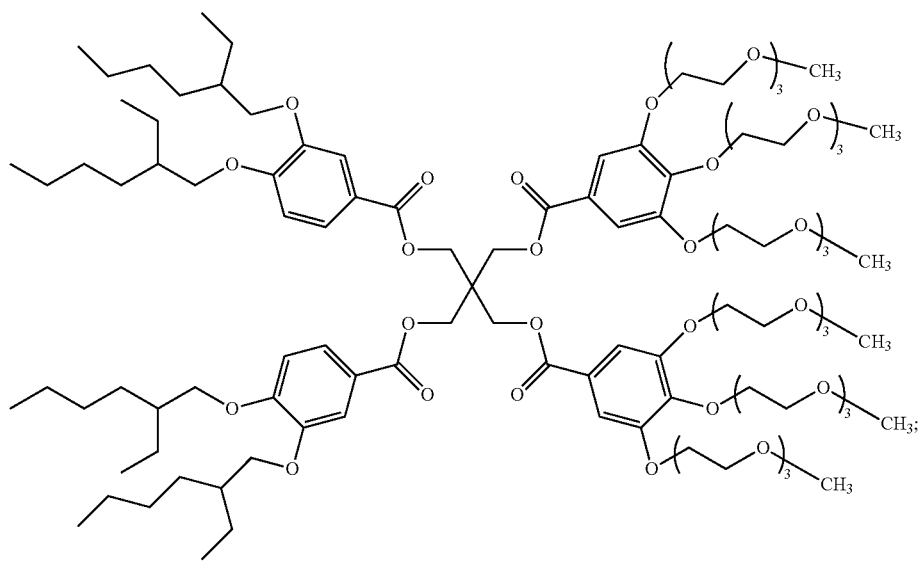
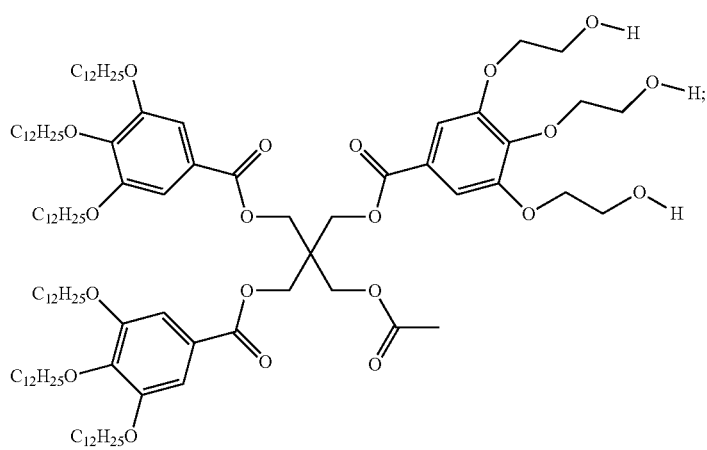

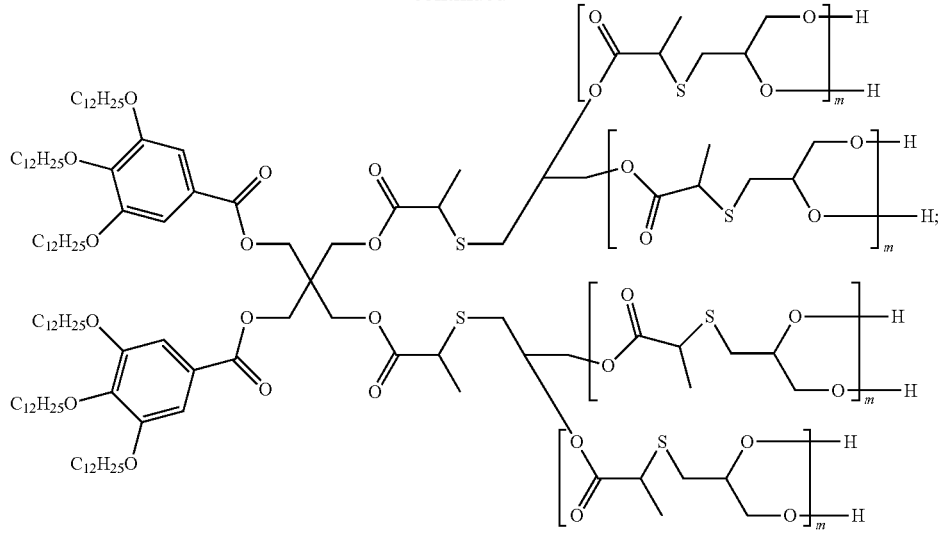

where, in some embodiments, m is an integer from 1 to 6;

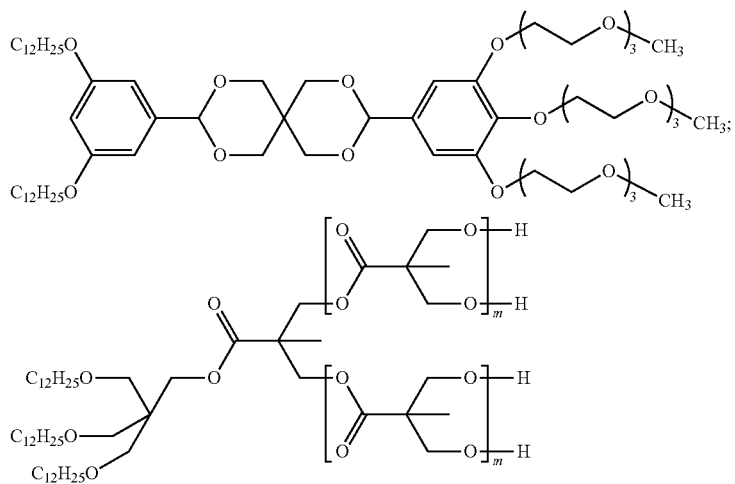

where, in some embodiments, m is an integer from 1 to 6;

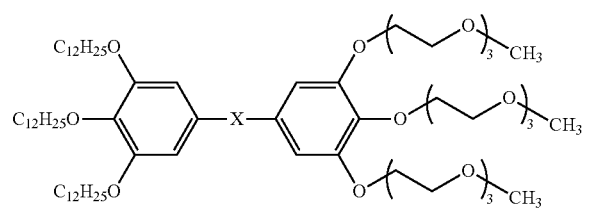

wherein X is —CH$_2$—NH—CO— or —NH—CO—;

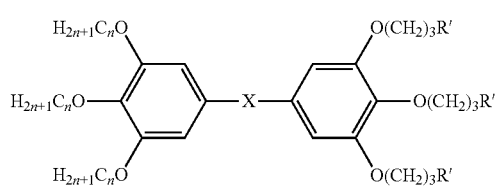

wherein X is —CH$_2$—NH—CO— or —NH—CO—; R' is —NHBoc or —NH$_3^+$Cl$^-$, and where, in some embodiments, n is 4 or 12; and

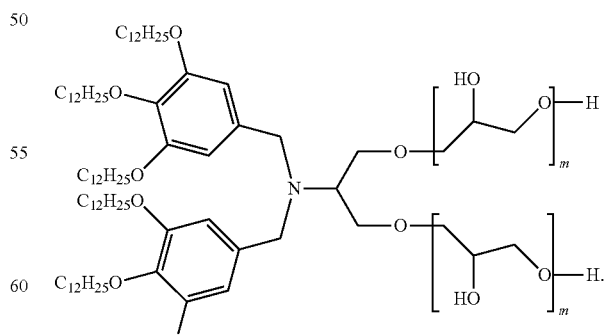

Figure 1:
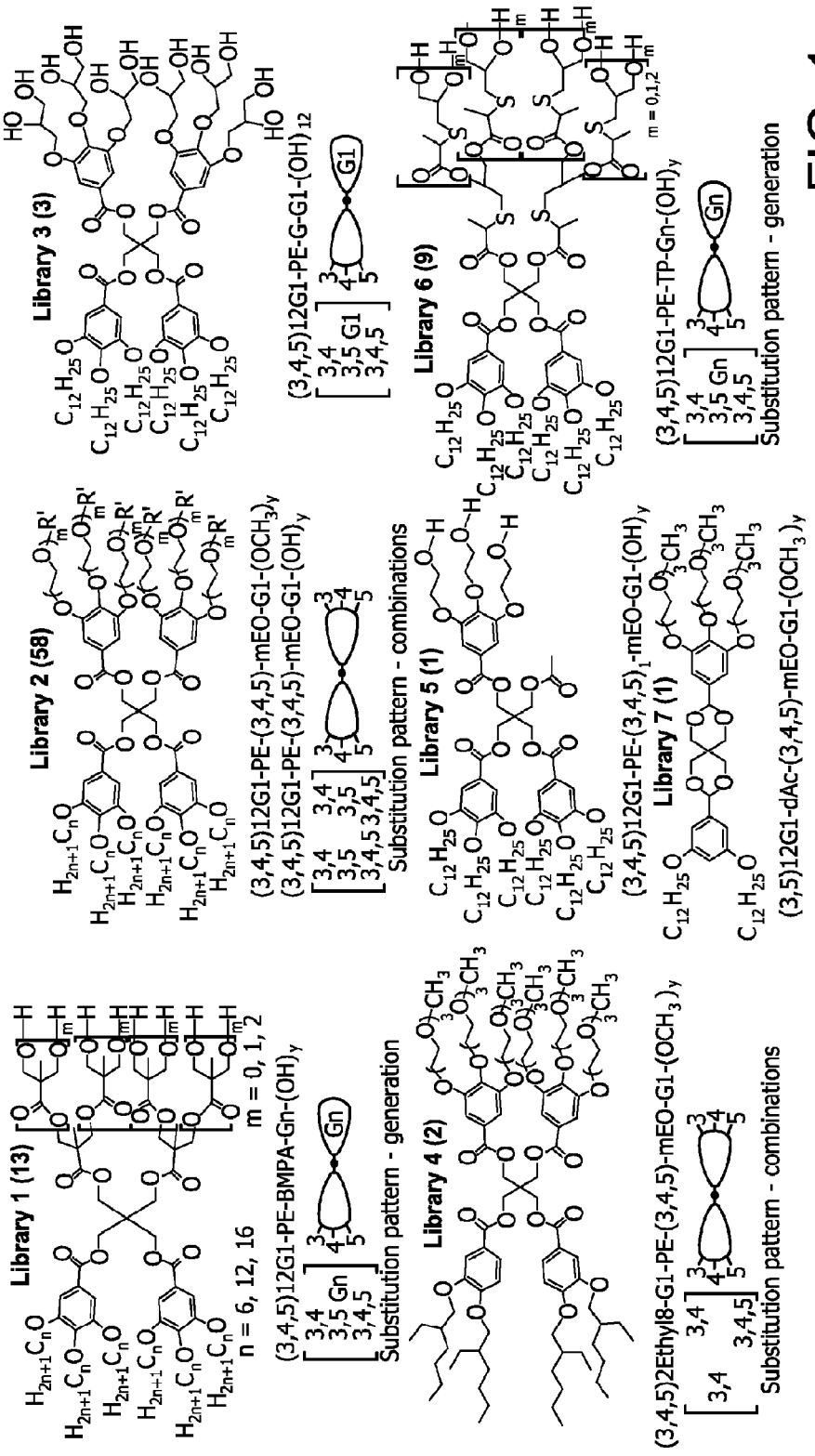
FIG. 1 depicts eleven libraries containing over 100 uncharged and positively charged amphiphilic Janus-dendrimers
Figure 1A:
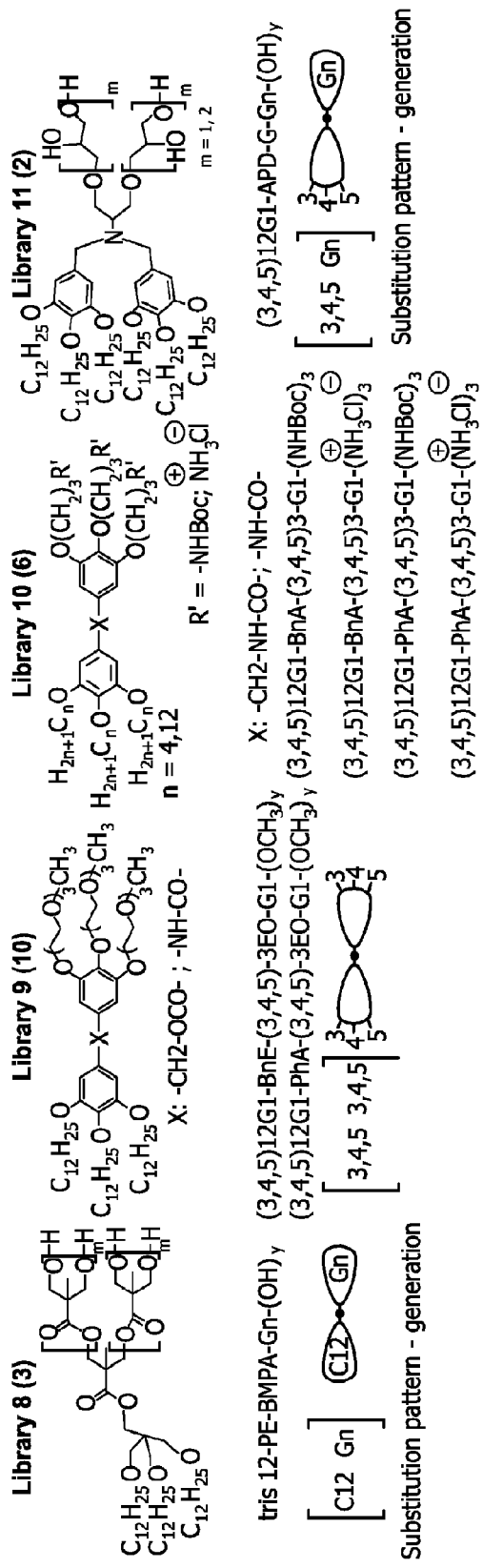

We have designed eleven libraries containing over 100 uncharged and positively charged amphiphilic Janus-dendrimers (FIG. 1). Dendrimers differ from polymers and block copolymers by their precise and monodisperse primary structure. These Janus-dendrimers were designed from natural $AB_3$ and constitutional isomeric $AB_2$ building blocks containing both hydrophilic and hydrophobic segments that can be rapidly combined to produce a large diversity of exact and monodisperse primary structures. These compositions were synthesized by a combination of convergent, for the hydrophobic part, and divergent or convergent methods for the hydrophilic part. Two hydrophobic segments, one aliphatic and one mixed aliphatic-aromatic, and six hydrophilic segments derived from oligoethylene oxide, dimethylolpropionic acid, glycerol, thioglycerol, tert-butylcarbamate and quaternary ammonium salts were synthesized (FIG. 1). This modular concept allowed the weight fraction of hydrophilic to hydrophobic blocks to be systematically varied. Block copolymers forming polymersomes are polydisperse and have limited scope for additional functionalization since they contain only two chain ends. The design of amphiphilic Janus-dendrimers allows a higher concentration and larger diversity of functionalities to be incorporated at both the hydrophilic and hydrophobic regions of the molecule.

The compositions of the instant invention are advantageous over the (3,4,5)12G1-PE-BMPA-Gn-(OH)y compositions of Library 1 due to their superior stability in buffered solutions.

All amphiphilic Janus-dendrimers depicted in FIG. 1 self-assemble in bulk and in water. Injection of ethanol solutions of Janus-dendrimers into water was monitored by dynamic light scattering as a function of concentration, temperature and time. Formation of vesicles by injection of ethanol and a variety of other protic and polar aprotic solutions into water was investigated as a function of temperature at a concentration of 0.5 mg/mL. Assemblies with sizes from 38 nm to 1188 nm with polydispersity ranging from 0.021 to 0.79 were observed. They are stable up to at least 250 days from 22 to 80° C. Surprisingly, most of the assemblies have low polydispersities of 0.021 to 0.200. For liposomes, these extremely low values are considered monodisperse. Dendrosomes from Library 1 show a dependence of both their size and polydispersity on concentration. (3,5)12G1-PE-BMPA-G2(OH)$_8$ (FIG. 1) exhibited polydispersity of 0.17 and Z-average size of 330 nm to polydispersity of 0.04 and Z-average size 94 nm for concentration ranging from 10 mg/mL to 0.5 mg/mL. Libraries containing oligoethyleneoxide in the hydrophilic part show very little dependence of polydispersity and size with concentration.

Figure 2:
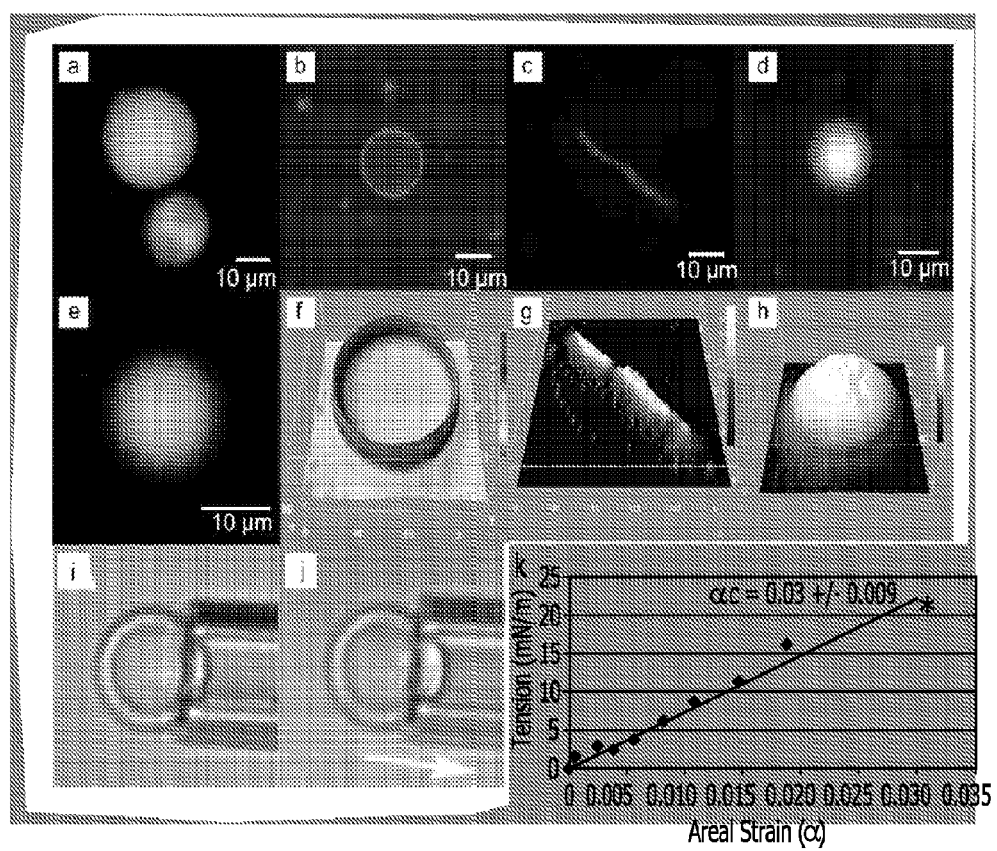
FIG. 2 presents Optical Microscopy of giant dendrosomes, their 3-D intensity profiles and micropipette aspiration experiments. a, Fluorescence microscopy image of dendrosome from (3,5)12G1-PE-(3,4)3EO—(OH)$_4$ encapsulating both hydrophobic Nile Red and hydrophilic Calcein dyes. b, f, Dendrosome from (3,4)12G1-PE-BMPA-G2-(OH)$_8$ visualized with Nile Red. c, g, Worm-like micelle from (3,4,5)12G1-PE-BMPA-G2-(OH)$_8$ encapsulating Nile Red. d, h, Spherical micelle from (3,4)12G1-PE-(3,4,5)3EO—(OH)$_6$ encapsulating Nile Red. e, Dendrosome from (3,4,5)12G1-PE-(3,4,5)3EO-G1-(OH)$_6$ visualized with Nile Red and Calcein. i, Micropipette aspiration assessment of mechanical strength by micro deformation under negative pressure of (3,5)12G1-PE-BMPA-G2(OH)$_8$. f, The same dendrosome under negative pressure showing small deformation of membrane. k, Areal strain ($\alpha_c$) determined from micropipette aspiration upon rupture.

Hydration experiments were performed on films drop cast onto a roughened Teflon® surface at a concentration of 2 mg (in 200 μL solvent) per 1 cm². Samples were dried under vacuum prior to hydration with 2 mL of ultra pure water or phosphate buffered saline at 50° C. This method was used to generate giant dendrosomes of 2 to 50 μm diameter, which were analyzed by either phase contrast or bright field microscopy. Visualization of both vesicle wall and cavity was carried out using fluorescence microscopy and a combination of hydrophobic (Nile Red) and hydrophilic dyes (Calcein). The hydrophobic dye was mixed with the Janus-dendrimer by adding 10 μM Nile Red to a solution of amphiphile in dichloromethane or diethyl ether. Films were prepared as described above and hydrated with 10 μM Calcein solution in saturated sucrose. Following hydration, Calcein containing dendrosomes were isolated by repeated centrifugation washing cycles. Giant unilamellar dendrosomes were visualized by fluorescence microscopy when the hydrophobic dye was observed to concentrate exclusively in the wall whereas the hydrophilic dye was observed only in the aqueous interior (FIG. 2). Micromanipulation experiments revealed that dendrosomes are more mechanically stable than phospholipid liposomes. They exhibit higher areal expansion moduli, $K_a$, display lipid-like critical areal strains and are impermeable (FIG. 2). Dendrosomes show better mechanical properties than the toughest polymersomes showing lower critical areal strain, $α_c$, and higher $K_a$. Dendrosomes have Ka of approximately 950 mN/m, well in excess of the 781 mN/m measured for liposomes generated from phospholipids containing 50% cholesterol.

Figure 3:
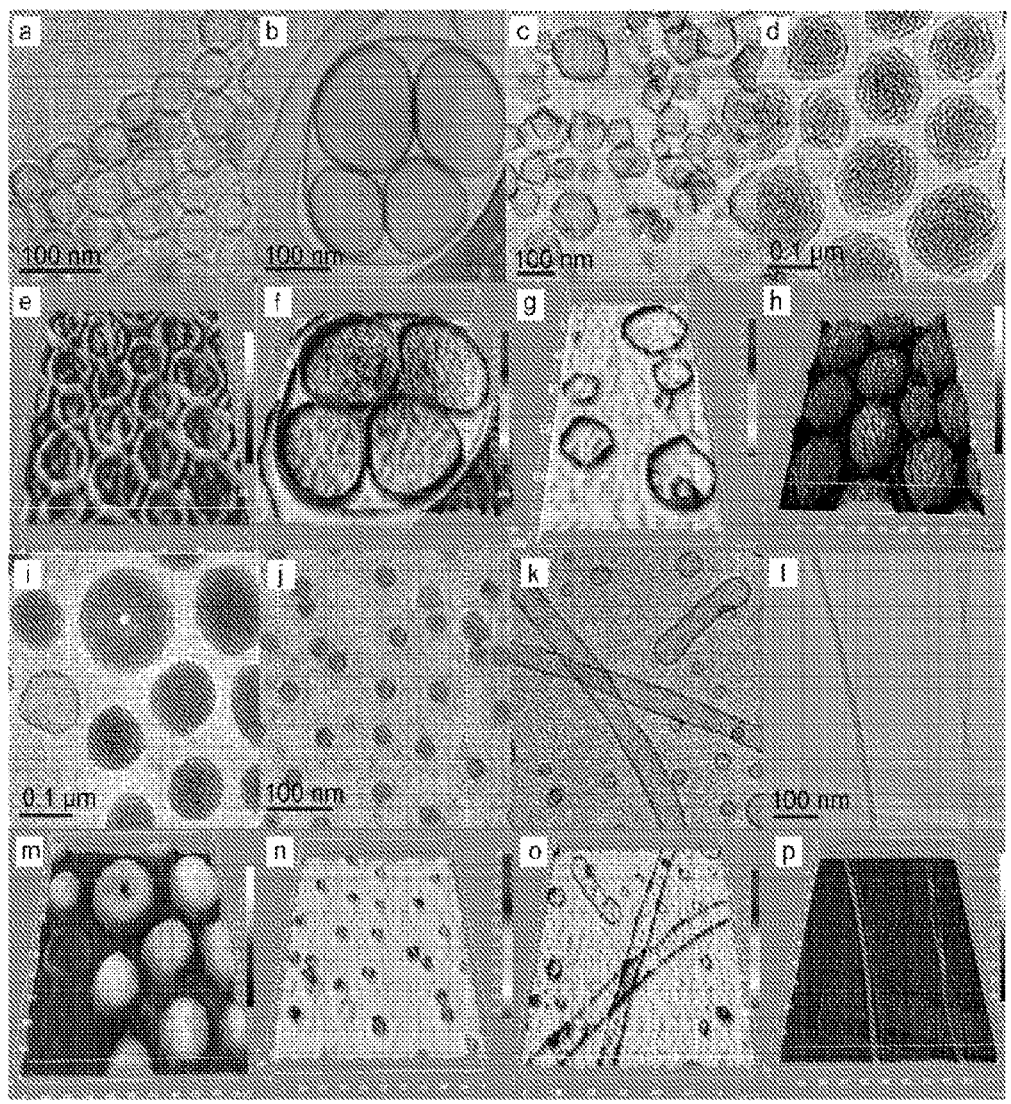
FIG. 3 presents Cryo-TEM of small assemblies and their 3-D intensity profile. a, e, Monodisperse dendrosomes from (3,4)12G1-PE-(3,5)-3EO-G1-(OCH$_3$)$_4$ in ultrapure water. b, f, Dendrosomes contained inside a dendrosome bag from (3,4,5)12G1-PE-(3,4,5)-3EO-G-(OH)$_6$ in PBS. c, g, Polygonal dendrosomes from (3,4)12G1-PE-(3,4)-3EO-G1-(OMe)$_4$. d, h, Bicontinuous cubic particles co-existing with low concentration of spherical dendrosomes from (3,5) 12G1-PE-(3,4,5)-2EO—(OMe)$_6$. i, m, Disc-like micelles and toroids from (3,4,5)12G1-PE-(3,5)-3EO—(OMe)$_4$. j, n, Micelles from (3,4,5)12G1-PE-BMPA-G2-(OH)$_8$. k, o, Dendrosomes from (3,5)12G1-PE-(3,4,5)-3EO—(OMe)$_6$. i, p, Rod-like, ribbon and helical micelles from tris12-PE-BMPA-G2-(OH)$_8$.
Figure 4:
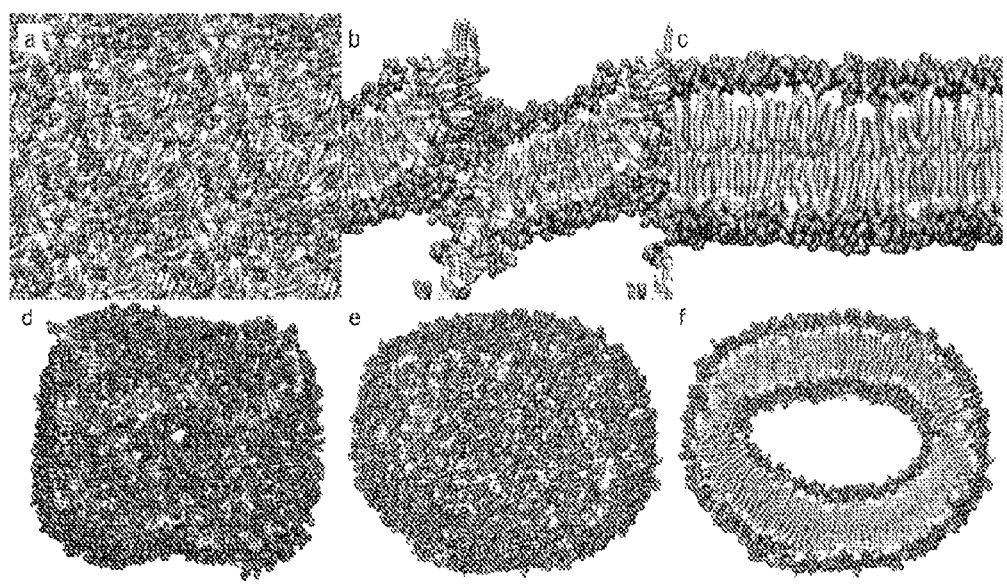
FIG. 4 presents computer simulation of self assembly of the amphiphilic dendron (3,5)12G1-PE-BMPA(OH)$_4$ using coarse grain (CG) molecular dynamics. The coarse grain interaction potentials were derived from fitting to all-atom of dendrimer bilayers. Spontaneous dendrosome formation occurs on a multinanosecond time scale. a, Small number of dendrons initial snapshot showing isotropic mixing of dendrons t=0 ns. b, Snapshot of simulation at t=20 ns showing spontaneous bilayer formation. c, Complete simulation showing spontaneously formation of bilayer t=40 ns. d, Large scale simulation of spontaneous vesicle formation snapshot at t=10 ns. e, complete simulation showing spontaneous vesicle formation at t=80 ns. f, Cut-away view of panel e, showing the hollow core of the vesicle.

Small assemblies fabricated by injection into water of ethanol solutions of the amphiphilic Janus-dendrimers were analyzed by cryo-TEM. Seventy nine of these assemblies are dendrosomes and dendromicelles and 62 have a polydispersity lower than 0.2 (FIG. 3a). In addition, dendrosomes within dendrosomes (Lasic, Nature 387, 26-27 (1997)), polygonal (Dubois, Nature 411, 672-675 (2001)) and tubular (Chiruvolu, Science 266, 1222-1225 (1994)) dendrosomes, bicontinuous cubic particles known as cubosomes (Almgren, Colloid Surf A: Phys. Eng. Asp. 174, 3-21 (2000)) and other complex architectures such as disc-like, toroidal, rod-like, polygonal, spherical, ribbon-like and helical ribbon-like micelles (Walter, Biophys J. 60, 1315-1325 (1991)) were also observed by the analysis of the 3-D intensity profiles of the optical micrographs and cryo-TEM images (FIGS. 2 and 3). To our knowledge this is the first example of dendrocubosome obtained in a two-phase non-ionic surfactant system. The bilayer thickness of the dendrosomes was measured from cryo-TEM and found to range from 5 to 8 nm. Liposomes from phospholipids exhibit thickness of 3 to 5 nm while the core thickness of a polymersome can be varied between 8 to 20 nm or greater. The mechanical properties in combination with the measured thicknesses indicate that dendrosomes are excellent candidates for models of biological membranes. Computer simulation using coarse grain molecular dynamics (Klein & Shinoda, Science 321, 798-800 (2008)) of (3,5)12G1-PE-BMPA-G1-OH)$_4$ (FIG. 1) demonstrated the self-assembly of dendrosomes of similar structure and dimensions with those observed by cryo-TEM (FIG. 4). The coarse grain interaction potentials were derived from fitting all-atom simulations of the Janus-dendrimer bilayers. Spontaneous dendrosome formation was observed on a multi-nanosecond timescale.

Additionally, the dendrosome membrane has an ideal thickness to be further engineered by incorporation of the pore forming protein Melittin (Yang, Biophys J. 81, 1475-1485 (2001)). This has proven difficult to achieve with polymersomes due the higher membrane thickness. Melittin incorporation into dendrosomes was investigated with Library 1 vesicles and a phospholipid SOPC control liposome formed by standard film hydration. Films were hydrated with a 25 mM solution of the fluorescent dye ANTS and the quencher DPX that is known to quench ANTS fluorescence at high concentrations. Following addition of Melittin, a dramatic increase in ANTS fluorescence was observed which is associated with the release of the dye due to pore formation. Lysis of the vesicles with Triton-X allowed a subsequent determination of 60% dye release following Melittin pore incorporation.

Figure 5:
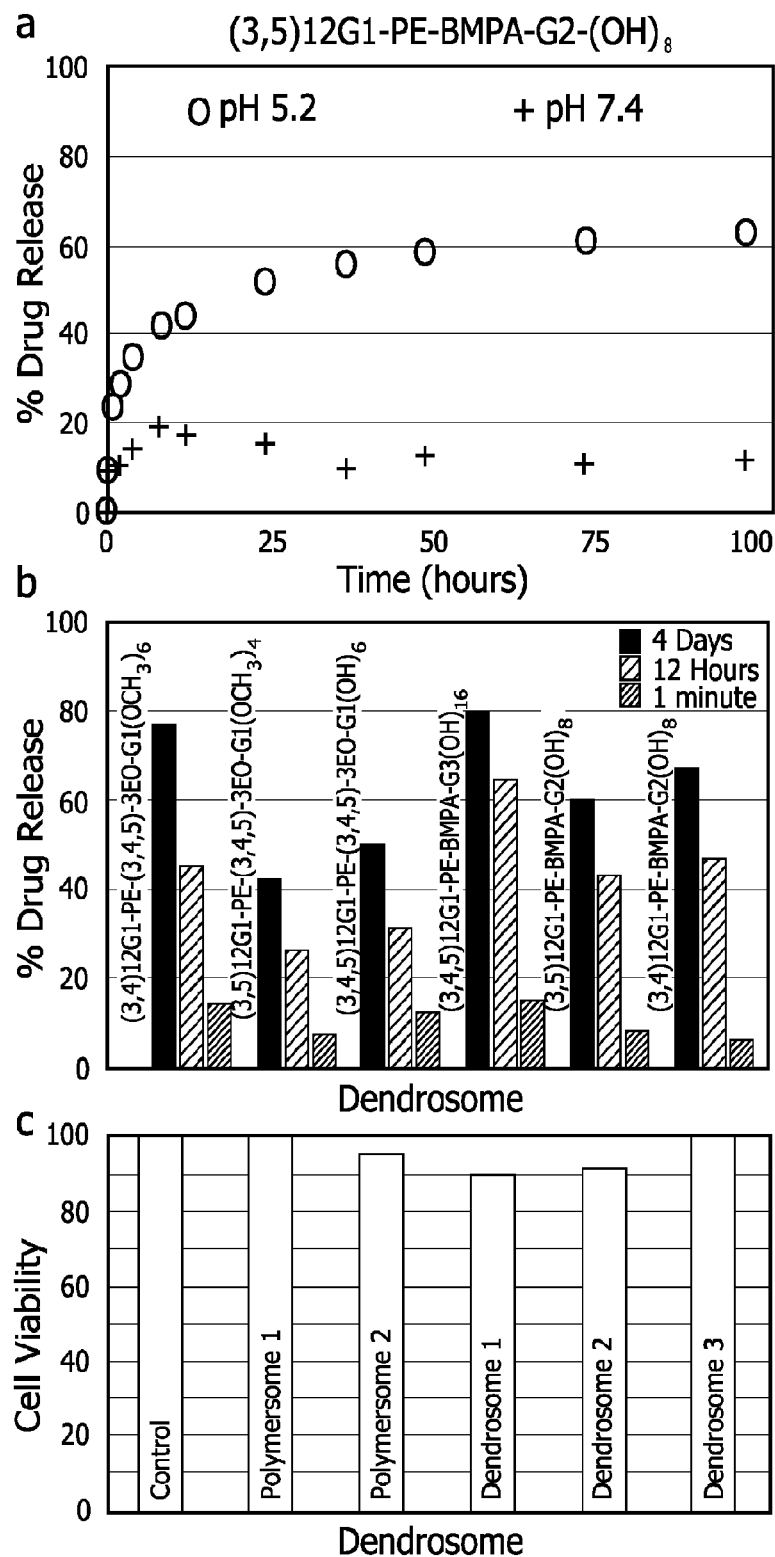
FIG. 5 illustrates drug release and cell viability. a, Release of Doxorubicin from dendrosomes assembled from (3,5) 12G1-PE-BMPA-G2-(OH)$_8$ showing excellent stability at physiological temperature and pH 7.4 and rapid release of the drug at physiological temperature and pH 5.2. b, Comparative release of Doxorubicin from dendrosomes from different libraries at pH 5.2 and 37° C., post addition of HCl. c, Cell viability study conducted on various dendrosomes from Library 2 with human umbilical vein endothelial cells (HUVECs) and CellTiter-Blue™ cell viability assay showing excellent biocompatibility of dendrosomes. Control: EGM Endothelial Growth Media (LONZA) Polymersome 1: hydrogenated polybutadiene-b-polyethyleneoxide; Polymersome 2: polycaprolactone-b-polyethyleneoxide; Dendrosome 1: (3,4)12G1-PE-(3,4,5)3EO-G1-(OMe)$_6$; Dendrosome 2: (3,5)12G1-PE-(3,4,5)3EO-G1-(OMe)$_6$; Dendrosome 3: (3,4,5)12G1-PE-(3,4,5)3EO-G1-(OH)$_6$.

The stability of dendrosomes was investigated in biologically relevant media by formation of membranes via ethanol injection into both phosphate buffered saline and citrate buffer. Dendrosomes from Library 1 showed poor stability in phosphate buffered saline. However, stability in citrate buffer was maintained over a period of two weeks. Dendrosomes from Library 2 exhibited excellent stability in ultrapure water as well as in phosphate and citrate buffers. Selected dendrosomes were loaded with the anthracyclin drug Doxorubicin that shows activity as a DNA intercalator that is used extensively in the treatment of Hodgkins lymphoma, stomach, lung and breast cancers. A significant side effect of Doxorubicin is its high cardiotoxicity at the therapeutic dosage. Cardiotoxicity is mitigated by encapsulation in the liposomal preparation trade named Doxil. However, synthetic liposomal drug formulations suffer from higher leakage and reduced in vivo stability when compared to their natural counterparts. Selected dendrosomes from libraries 1 and 2 were loaded by hydration of dendrimer films with a Doxorubicin/ammonium sulfate solution followed by sonication and dialysis to yield dendrosomes loaded with Doxorubicin. Doxorubicin release was monitored fluorometrically at 37° C. at physiological (~7.2~7.4)) and acidic pH (~5.2~5.4). FIG. 5 illustrates a significantly higher release of drug at acidic pH. Rapid growth and higher metabolic turnover exhibited by neoplastic cells results in both leaky vasculature and a lower than physiological pH (~5.2). As a consequence, dendrosomes will tend to target tumor cells rather than healthy tissue. Janus-amphiphiles contain cleavable bonds whose breakdown under acidic conditions destabilize vesicle structure. Without special design, NMR and MALDI-TOF analysis showed that the cleavable bond in the Janus-dendrimer structure under low pH conditions is the aromatic-aliphatic ester bond. Engineering the dendrosome with alternative pH-sensitive groups10 is in progress. Selected Janus-dendrimers tagged with Texas Red dye were shown to co-assemble into fluorescent giant unilamelar liposomes with unlabelled Janus-dendrimers, block-copolymers and phospholipids, which demonstrate the potential utility of tagged Janus-dendrimers in theranostics for detection and treatment of diseases.

In order to estimate the toxicity of these dendrosomes, cell viability experiments were carried out on human umbilical vein endothelial cells (HUVEC). Dendrosomes from Library 2 were incubated with HUVECs at varying concentrations for a period of four hours. Cell viability assays with Cell Titer-Blue™, a dye that becomes fluorescent in the presence of living cells were carried out at 1, 2 and 4 h intervals. Library 2 showed no discernable toxicity when compared to the control experiments (FIG. 5) indicating an excellent biocompatibility for dendrosomes. Several examples of liposomes assembled from positively charged polymer-dendrimer block copolymers (Vanhest, Science 268, 1592-1595 (1995)) and from charged amphiphilic dendrimers (Esfand, Drug Discov. Today 6, 427-436 (2001); Al-Jamal, J. Pharm. Sci. 94, 102-113, (2005)) are available. Nevertheless, the results reported here demonstrate a simple and general strategy to the design and synthesis of amphiphilic Janus-dendrimers that self-assemble into stable and monodisperse dendrosomes and other complex architectures. Therefore, dendrosomes expand the field of supramolecular dendrimer chemistry into new functions with possible technological applications.

The term "alkyl", as used herein, refers to a substituted or unsubstituted aliphatic hydrocarbon chain and includes, but is not limited to, straight and branched chains. In some embodiments, the alkyl group contains from 1 to 30 (1 to 12, in some embodiments) carbon atoms. For example, methyl, ethyl, propyl, isopropyl, butyl, i-butyl and t-butyl are encompassed by the term "alkyl." Specifically included within the definition of "alkyl" are those aliphatic hydrocarbon chains that are optionally substituted.

The term "Boc" refers to t-butyl carbamate.

As used herein, the term "rt" refers to room temperature.

The invention is illustrated by the following examples that are intended to be illustrative and not limiting.

Materials

Di-t-butyl dicarbonate (Boc anhydride, 99%), 3-chloro propylammonium chloride (98%), benzyl bromide (98%), 1-bromobutane (99%), 1-bromooctane (99%), 1-bromododecane (98%), 1-bromohexadecane (99%), citric acid (99%), N,N'-dicyclohexylcarbodiimide (99%), 4-dimethylaminiopyridine (99%), N-bromosuccinimide (NBS) (99%), Dowex resin, hydrazine monohydrate (99%), N-methyl morpholine (99%), methyl 3,4-dihydroxybenzoate (99%), 4-dimethylamino pyridine (99%), allyl bromide (99%), methyl 3,4,5-trihydroxybenzote (99%), methyl 3,5-dihydroxybenzoate (99%), DL-serine (99%), sodium azide (99%), 2,2-bis (hydroxymethyl) propionic acid (bis-MPA) (99%), tetrabutyl ammonium bromide (99+%), triethylene glycol (99%), triphenylphosphine ($PPh_3$) (99%) (all from Acros), 3,4-dihydro 2H-pyran (99%), 2-ethylhexyl bromide (95%), sodium azide (99%), benzene (all from Acros), 2-bromopropionyl bromide (97%), 1-thioglycerol (98%), diethylene glycol monomethyl ether (99.6%), thionyl chloride (99.5%), pentaerythritol (98%), azobisisobutyronitrile (AIBN), $LiAlH_4$ (95%), graphite, 2-methyl 2-propanol (99%), Palladium 10 wt. % on activate carbon, p-toluene sulfonic acid (98%), p-toluene sulfonyl chloride (98%), potassium osmate dihdrate, 4-methylmorpholine N-oxide (97%), anhydrous $K_2CO_3$, (all from Aldrich), triethylene glycol monomethyl ether (97%) from Fluka, ethylene glycol, ethylene glycol monomethyl ether, anhydrous $MgSO_4$, Celite 545®, NaOH, $NaHSO_4$ $NaHCO_3$, $NaNO_2$, KOH, NaCl, HCl, $HNO_3$, glacial acetic acid, dimethyl sulfoxide, acetonitrile, dioxane, ethanol, hexanes, ethyl acetate, chloroform, toluene, methanol, acetone, acetonitrile, pyridine, tetrahydrofuran (all from Fisher) were used as received. Triethylamine ($Et_3N$) (99%, Fisher) was distilled prior to use. Dichloromethane was dried over $CaH_2$ (from SIGMA-Aldrich) and freshly distilled before use. Tetrahydrofuran was refluxed over sodium (from SIGMA-Aldrich)/benzophenone (from Acros) and freshly distilled prior to use. Deuterated solvents for NMR analysis were purchased from Cambridge Isotope Laboratories, Inc. All other chemicals were commercially available and were used as received.

Instrumentation and Techniques

NMR $^1$H NMR (500 MHz) and $^{13}$C NMR (125 MHz) spectra were recorded on a Bruker DRX500 and Bruker DMX400 instruments.

Mass Spectrometry

Matrix-assisted laser desorption/ionization time-of-flight (MALDI-TOF) mass spectrometry was performed on a PerSeptive Biosystems-Voyager-DE (Framingham, Mass.) mass spectrometer equipped with a nitrogen laser (337 µm) and operating in linear mode. Internal calibration was performed using Angiotensin II and Bombesin as standards. The analytical sample was obtained by mixing a THF solution of analyte (5-10 mg/mL) with a THF solution of matrix (3,5-dimethoxy-4-hydroxy-transS3 cinnamic acid or 4-hydroxybenzylidenemalononitrile, 10 mg/mL) in a 1/5 v/v ratio. The prepared solution of the analyte and matrix (0.5 µL) was loaded on the MALDI plate and allowed to dry at 23° C. before the plate was inserted into the vacuum chamber of the MALDI instrument. The laser steps and voltages applied were adjusted depending on both the molecular weight and the nature of analyte.

Purity Analysis

The purity of the products was determined by a combination of thin-layer chromatography (TLC) on silica gel coated aluminum plates (with $F_{254}$ indicator; layer thickness, 200 μm; particle size, 2-25 μm; pore size 60 Å, SIGMA-Aldrich) and high pressure liquid chromatography (HPLC) using THF as mobile phase at 1 mL/min, on a Shimadzu LC-10AT high pressure liquid chromatograph equipped with a Perkin Elmer LC-100 oven (40° C.), containing two Perkin-Elmer PL gel columns of $5\times10^2$ and $1\times10^4$ Å, a Shimadzu SPD-10A UV detector (λ=254 nm), a Shimadzu RID-10A RI-detector, and a PE Nelson Analytical 900 Series integrator data station.

Thermal Analysis by Differential Scanning Calorimetry

Thermal transitions were determined on a TA Instruments Q100 differential scanning calorimeter (DSC) equipped with a refrigerated cooling system with 10° C. $min^{-1}$ heating and cooling rates. Indium was used as calibration standard. The transition temperatures were calculated as the maxima and minima of their endothermic and exothermic peaks. An Olympus BX51 optical microscope (100× magnifications) equipped with a Mettler FP82HT hot stage and a Mettler Toledo FP90 Central Processor was used to verify thermal transitions and to characterize anisotropic textures.

Dynamic Light Scattering

Dynamic light scattering measurements (DLS) were performed with a Malvern Instruments particle sizer (Zetasizer® Nano S, Malvern Instruments, UK).

Circular Dichroism

Circular dichroism (CD) and UV/vis spectra were recorded on a Jasco J-720 spectrophotometer equipped with a NESLAB RTE-111 variable temperature circulator. The samples were dissolved at 22° C. in a mixture of cyclohexane/tetrahydrofuran 98.7/1.3 v/v ($2.5\times10^{-5}$ M). CD measurements were performed using a 1 mL quartz cuvette of 0.1 cm path length and the following parameters: scanned optical range, 210-320 nm; scan band width, 1 nm; scanning speed, 100 nm/min; response, 1 sec; accumulations, 5; 3 scanned thermal ranges: 8-72° C., 72-8° C., and 8-72° C. (data pitch: 2° C.; temperature slope: 1° C./min). Before starting the experiment the samples were allowed to reach the 8° C. starting temperature (~10-15 min) but once started the 3 thermal cycles were performed successively. Data were processed using Jasco Spectra Manager V.1.51 software.

Cryo-TEM

All samples for cryo-TEM were prepared within a controlled environment vitrification system (CEVS)1 in a saturated water vapor environment at 25° C. A droplet (10-20 μL) of solution was placed on a carbon coated copper TEM grid (Ted Pella) held by non-magnetic tweezers. Filter paper was used to blot excess sample away, resulting in a thin film of solution spanning the grid. Due to the low concentration of organic material in these samples (and lower viscosity than dispersions of block copolymer micelles), it was sometimes necessary to repeat the droplet placement and blotting process in order to obtain suitable specimens for imaging. The sample was allowed to relax for approximately 30 seconds to remove any residual stresses imparted by blotting, then quickly plunged into liquefied ethane (~90 K) cooled by a reservoir of liquid nitrogen to ensure the vitrification of water. Prepared grids were stored under liquid nitrogen until imaging. Specimen imaging was executed at −178° C. using a Gatan 626 cryogenic sample holder in a JEOL 1210 TEM operating at 120 kV. A cooled Gatan 724 multiscan CCD camera was used to record the images. Image processing, including background subtraction, and image analysis was completed with Gatan Digital Micrograph 3.9.1 software. Intensity profiles were created by using a subroutine in Digital Micrograph, which averages the image intensity over a specified width. These profiles were used to measure length scales within the images, and were only produced over a uniform region of the image with a width of at least 10 pixels to avoid pixel fluctuation artifacts.

Osmolarity

Osmotic strengths were measured using a Model 3300 osmometer from Advanced Instruments (Norwood, Mass.). Sonication was performed using a sonicator bath (Branson; Model 3510).

Fluorescence Spectra

Fluorescence was measured fluorometrically (using a SPEX Fluorolog-3 Model FL3-11 fluorimeter) at various intervals.

Synthetic Methods

Janus-dendrimers are amphiphilic molecules containing two dissimilar hydrophilic and hydrophobic segments. The synthetic strategy for the synthesis of Janus-dendrimers allowed easy connection of the two segments via ester or amide connectivity facilitating subsequent generation of a large variety of amphiphilic molecules. Substitution pattern for the hydrophobic unit coupled with substitution pattern and generational approach for the hydrophilic segment were used. The hydrophobic unit was synthesized by a convergent approach via direct etherification of the 3,4-, 3,5-, 3,4,5-hydroxybenzoates with linear or branched alkyl bromides. The hydrophobic segment contains alkyl phenyl ethers for Libraries 1-7,9-11 or alkyl ethers for Library 8. Six hydrophilic segments containing dimethyl propionic acid (Libraries 1, 8, 11)), oligoethylene oxide (Libraries 2, 4, 5, 7, 9 and 10), glycerol (Library 3, 11), thioglycerol (Library 6), t-butyl carbamate and quaternary ammonium salts (Library 10) were used.

Building from a previous procedure (Ropponen, Org. Lett. 6, 2495-2497 (2004)), the orthogonal benzylidene and isopropylidene protecting groups allow the pentaerythritol core to be differentially substituted yielding the amphiphilic Janus-dendrimers in Library 1 (Scheme S1). In the previous publication the benzylidene protected compound 2 was deprotected from the pentaerythritol core via hydrogenolysis at 35° C. under Pd/C and 100 psi in tetrahydrofuran (61% yield). The benzilidene protecting groups from the third generation Janus-dendrimers were removed under milder conditions in dichloromethane-MeOH mixture at 23° C., Pd/C and atmospheric $H_2$ pressure (Ihre, J. Am. Chem. Soc. 123, 5908-5917 (2001)). The same procedure was used for the deprotection of benzylidene protected pentaeritrytol (compounds 16a-16c) during the synthesis of tryethylene glycol Janus-dendrimers (Scheme S2). Janus-dendrimers from Library 1 up to the second generation were synthesized by iterative addition of isopropylidene protected bis-MPA fragments via DCC/DPTS coupling (Moore, Macromolecules 23, 65-70 (1990)), and deprotection with either 6M HCl in THF or ion-exchange resin (DOWEX) in MeOH-DCM. Slow reaction rates and significant cleavage of the ester groups in the deprotection step of third generation Janus-dendrimers from Library 1 were eliminated by replacing the isopropylidene protecting group with the corresponding benzylidene. The benzylidene protected Janus-dendrimer could be cleaved in up to 88% yield under mild conditions using Pd/C at 23° C. and atmospheric pressure (Scheme S1).

The benzylidene protected penthaerythritol was again employed in the synthesis of Library 2 containing oligoethylene oxide type Janus-dendrimers (Schemes S2-S6). For the synthesis of alcohol terminated hydrophilic blocks of Library 2, both benzyl ether (Mamdouh, Langmuir, 20, 7678-7685 (2004)) (Scheme S4) and tetrahydropyran protecting groups (Scheme S5) were used. Significantly higher yields were obtained with benzylethers compared to the tetrahydropyran protected analogues. This is due to the mild deprotection conditions yielding toluene as the only side product that results in facile purification of the Janus-dendrimer by simple filtration of the catalyst and evaporation of the solvent. In contrast, tetrahyropyran deprotection requires an aqueous work up, which often results in the formation of stable emulsions. The same procedures were used in the synthesis of Library 4 containing branched tail hydrophobic segments. Janus-dendrimer from Library 5 was obtained as a side product of the esterification reaction arising from incomplete removal of acetic acid from the saponification the methylester to form benzoic acid (Hillmayer, Science 271, 976-978 (1996)).

The synthesis of glycerol functionalized Janus-dendrimers of Library 3 was inspired from the work of Sindhu, et al (J. Magn. Magn. Mater. 296, 104-113 (2006).) (Scheme S7). It employed the same protection coupling deprotection procedure as for Library 2 to synthesize the first generation allyl substituted dendrimer. Oxidation of the double bond to form the diol was carried out in up to 67% yield (Haag, J. Am. Chem. Soc. 122, 2954-2955 (2000)). Only a limited number of compounds were synthesized from this library due to the high cost of osmium tetraoxide and its associated toxicity in dendrosome formulations.

The synthesis of Library 11 replaced the pentaerythrytol core with 2-(dibenzylamino)propane-1,3-diol (Scheme S8) (Haag, J. Am. Chem. Soc. 122, 2954-2955 (2000)). The hydrophilic block was comprised of glycerol dendron subunits. However, allylation of the 2-(dibenzylamino)propane-1,3-diol core proved challenging since it results in slow and incomplete allylation when allyl bromide was used as both reactant and solvent with an aqueous solution of sodium hydroxide in the presence of the phase transfer catalyst tetrabutylammonium iodide. Changing the solvent system to a mixture of dimethylsulfoxide and THF and the catalyst to tetrabutylammonium bromide44 resulted in 94% yield of the fully allylated compound in 12 h. Transformation of the double bond to the corresponding diol with osmium tetroxide resulted in significant cleavage of the benzyl arms yielding only 23% of Janus-dendrimer. Library 6 was synthesized via a previously reported procedure from our lab using the divergent "click chemistry" methodology (Scheme S10) (Rosen, J. Polym. Sci. Part A: Polym. Chem. 47: 3931-3939, 2009). The diol was acylated with bromopropionyl bromide to the corresponding bromide in the presence of pyridine to give dibromo (Wagner, Eur. J. Pharm. Biopharm 54, 213-219 (2002)) in very good yield (94-100%). Subsequent nucleophilic substitution of the bromide with thioglycerol in DCM-MeCN resulted in the first generation thioglycerol Janus-dendrimers in 86-93% yield. The hydrophobic nature of the lower generation Janus-dendrimers required addition of dichloromethane in order to increase the solubility in the polar solvent. At higher generation the bromide displacement exhibited significant side reactions and cleavage of the ester bonds over extended periods of time.

Janus-dendrimers of Library 7 incorporate 2 acid labile acetal moieties. The formation of the diacetal resulted in significant "scrambling" resulting in formation of statistical amounts of the homo diacetal side products and the amphiphilic diacetal (Scheme S11).

Library 8 consisting of trisdodecyloxy substituted pentaerythritol bis-MPA Janus-dendrimers followed a literature procedure (Dumoulin, Chem. Eur. J. 13, 5585-5600, (2007)). However, the product of the tris alkylation of pentaerythritol could only be obtained in 19% yield (Scheme S12).

The esters from Library 9 were synthesized via standard DCC couplings. Amines were synthesized from the corresponding dodecyloxy benzoic acid via nitro-Hunsdiecker reaction according to the procedure of Das et at (Org. Lett. 4, 3055-3058 (2002)). Subsequent coupling to form the amide was carried out under standard DCC/DPTS condition (Schemes S13-S14).

Janus-dendrimers of Library 10 functionalized with tert-butyl carbamate in the hydrophilic block were synthesized by using a methodology elaborated by Mulders et al. (Tetrahedron Lett. 38, 631-634 (1997)). In this case the amine was synthesized by the procedure of Percec et al (Chem. Eur. J. 5, 1070-1083 (1999)) and coupled via CDMT/NMM coupling to yield the Janus-dendrimer in 40-70% yield. The corresponding quaternary ammonium salt was obtained via deprotection with 2M HCl in diethylether. The benzylamines were synthesized by transformation of the benzyl chloride to the corresponding amine via the azide (Schemes S15-S16).

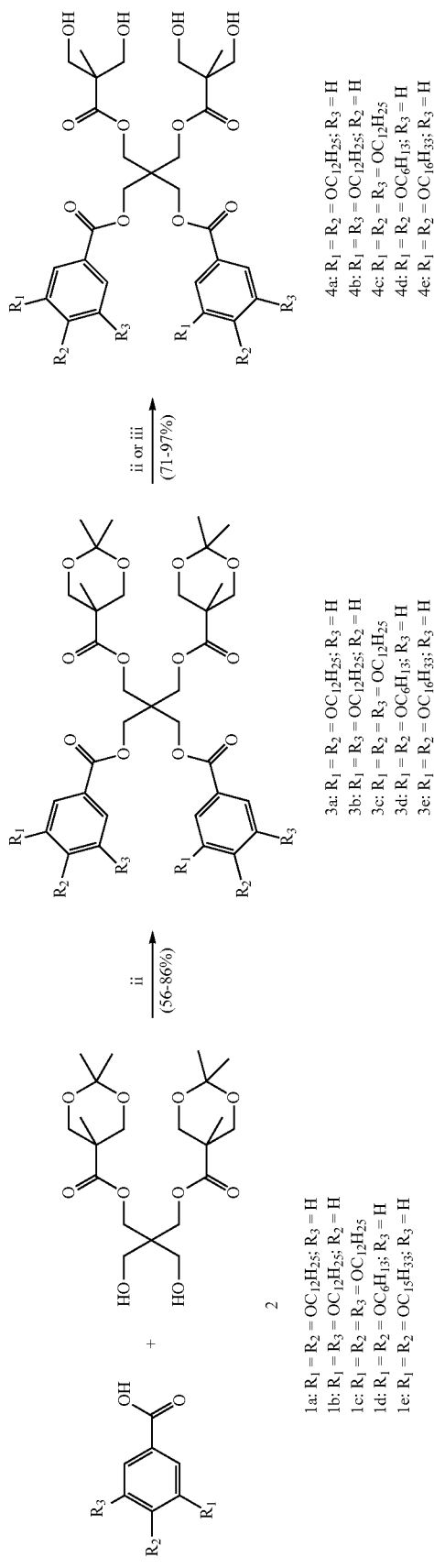

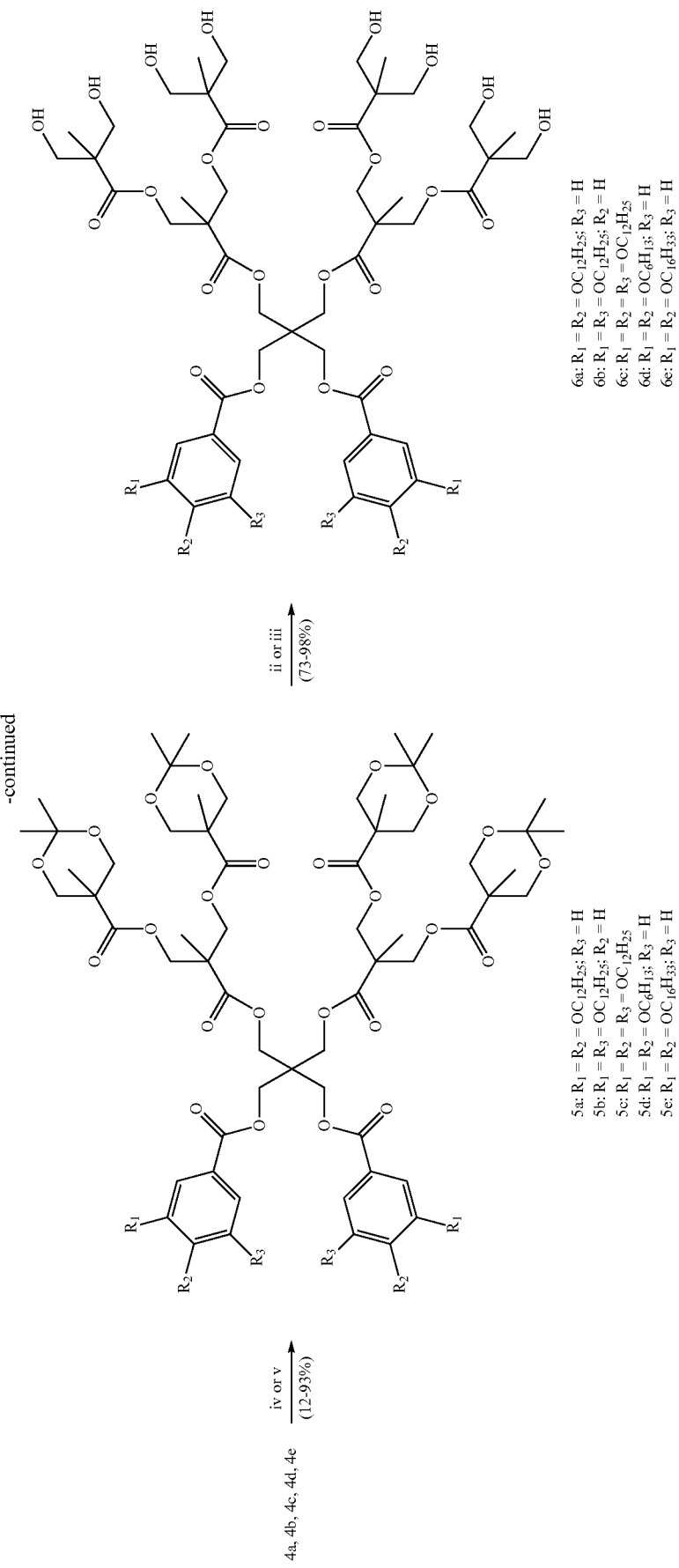

-continued
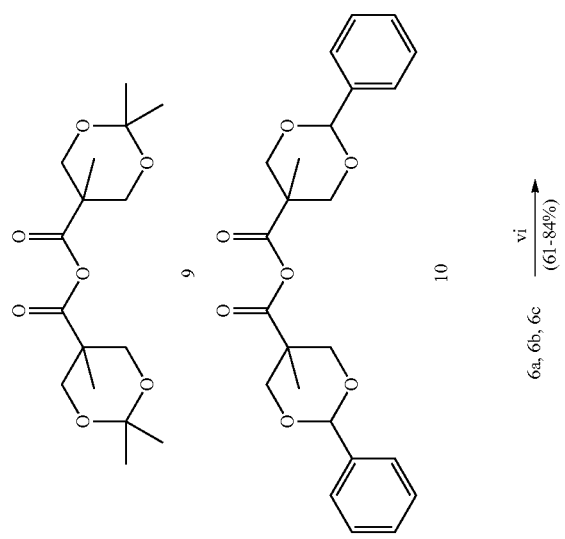

-continued
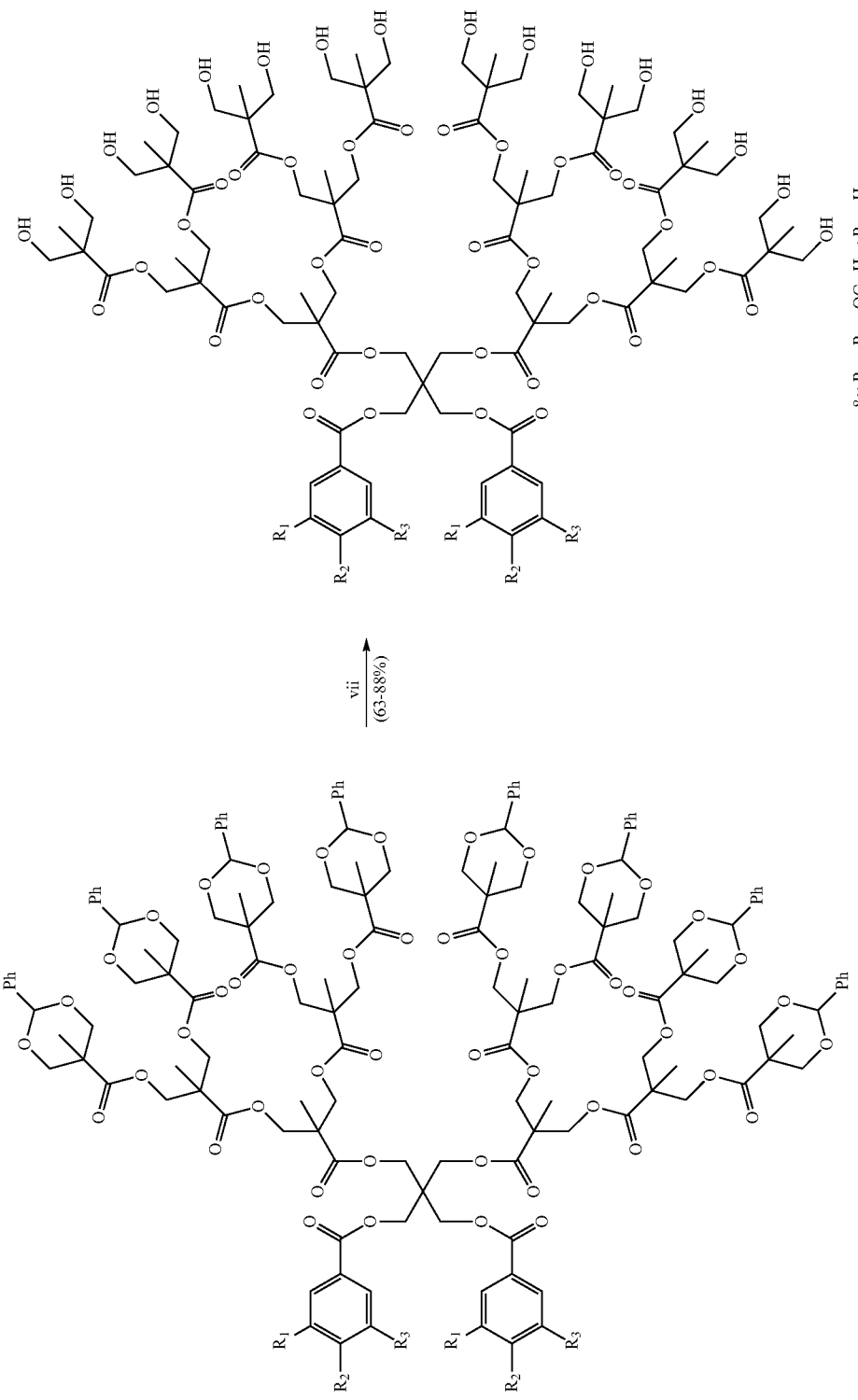
7a: $R_1 = R_2 = OC_{12}H_{25}$; $R_3 = H$
7b: $R_1 = OC_{12}H_{25}$; $R_2 = H$
7c: $R_1 = R_2 = R_3 = OC_{12}H_{25}$
8a: $R_1 = R_2 = OC_{12}H_{25}$; $R_3 = H$
8b: $R_1 = OC_{12}H_{25}$; $R_2 = H$
8c: $R_1 = R_2 = R_3 = OC_{12}H_{25}$
[a]Reagents and conditions: (i) DCC, DPTS, $CH_2Cl_2$; (ii) HCl, THF (25° C.); (iii) Dowex, $CH_2Cl_2$—MeOH; (iv) 9, DMAP, py- $CH_2Cl_2$ (25° C.); (v) bis-MPA, DCC, DPTS, $CH_2Cl_2$ (25° C.); (vi) 10, DMAP, py- $CH_2Cl_2$ (25° C.); (vii) $H_2$,Pd/C, MeOH-DCM (25° C.)

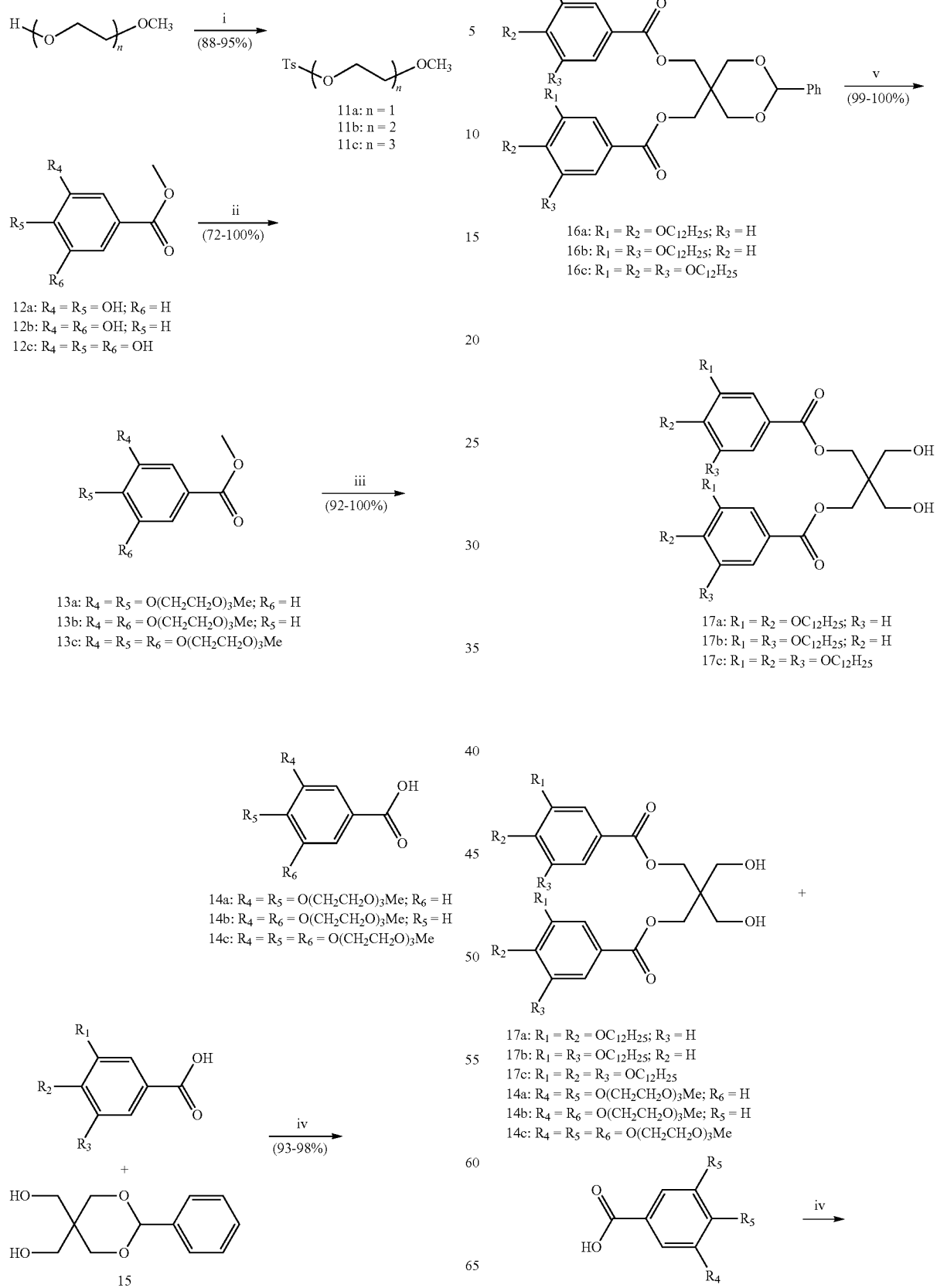

-continued

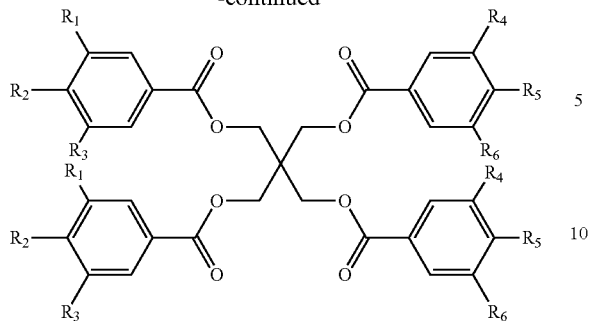

18a: $R_1 = R_2 = OC_{12}H_{25}$; $R_3 = H$; $R_4 = R_5 = O(CH_2CH_2O)_3Me$; $R_6 = H$; 50%
18b: $R_1 = R_2 = OC_{12}H_{25}$; $R_3 = H$; $R_4 = R_6 = O(CH_2CH_2O)_3Me$; $R_5 = H$; 36%
18c: $R_1 = R_2 = OC_{12}H_{25}$; $R_3 = H$; $R_4 = R_5 = R_6 = O(CH_2CH_2O)_3Me$; 50%
18d: $R_1 = R_3 = OC_{12}CH_{25}$; $R_2 = H$; $R_4 = R_5 = O(CH_2CH_2O)_3Me$; $R_6 = H$; 72%
18e: $R_1 = R_3 = OC_{12}H_{25}$; $R_2 = H$; $R_4 = R_6 = O(CH_2CH_2O)_3Me$; $R_5 = H$; 25%
18f: $R_1 = R_3 = OC_{12}H_{25}$; $R_2 = H$; $R_4 = R_5 = R_6 = O(CH_2CH_2O)_3Me$; 79%
18g: $R_1 = R_2 = R_3 = OC_{12}H_{25}$; $R_4 = R_5 = O(CH_2CH_2O)_3Me$; $R_6 = H$; 59%
18h: $R_1 = R_2 = R_3 = OC_{12}H_{25}$; $R_4 = R_6 = O(CH_2CH_2O)_3Me$; $R_5 = H$; 43%
18i: $R_1 = R_2 = R_3 = OC_{12}H_{25}$; $R_4 = R_5 = R_6 = O(CH_2CH_2O)_3Me$; 82%

[a]Reagents and Conditions: (i) TsCl, NaOH, THF-water; (ii) 11c. $K_2CO_3$, DMF 70° C.); (iii) KOH, water (100° C.), (vi) DCC, DTPS, DCM (25° C.); (v) $H_2$, Pd/C, MeOH/DCM (25° C.).

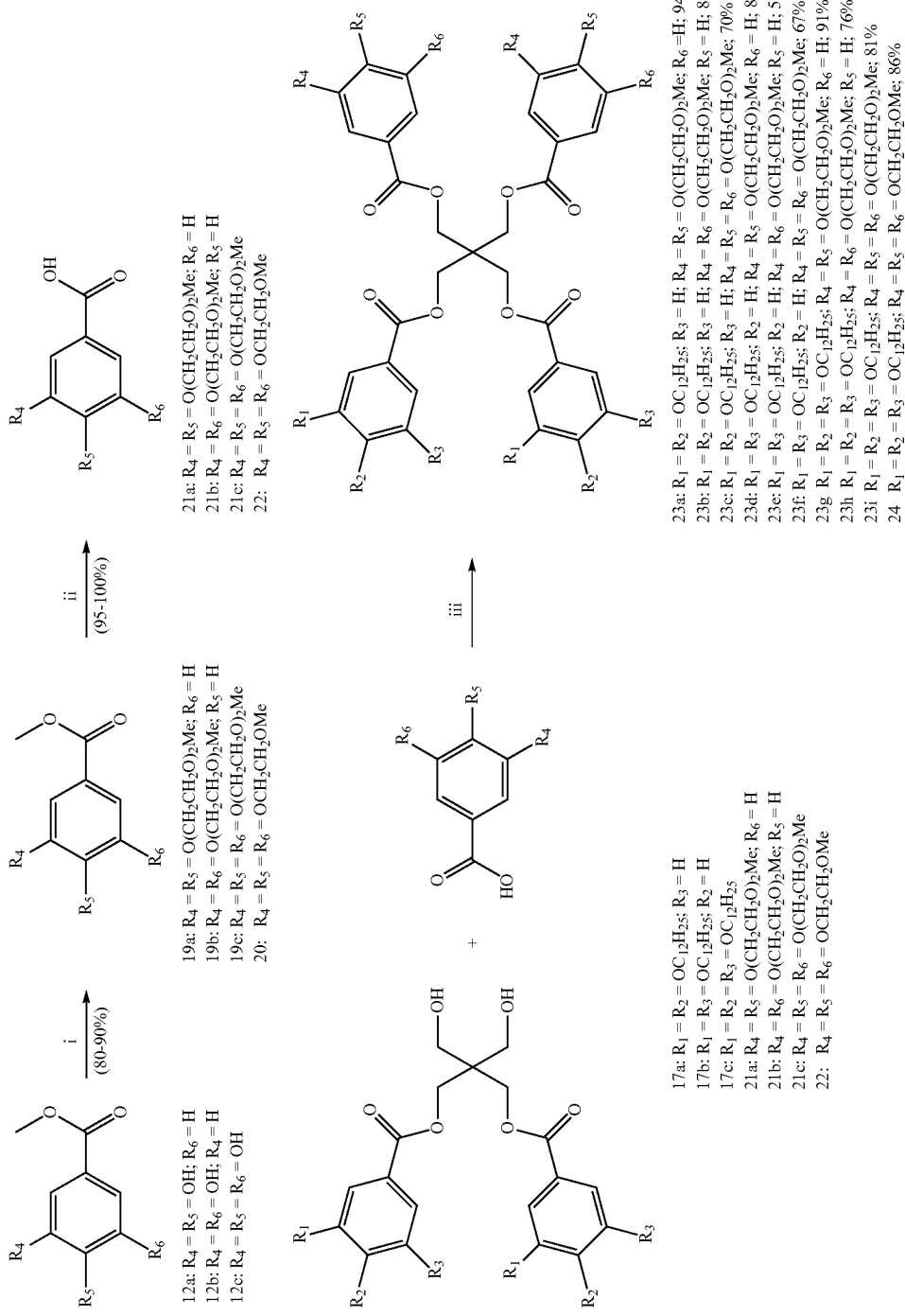

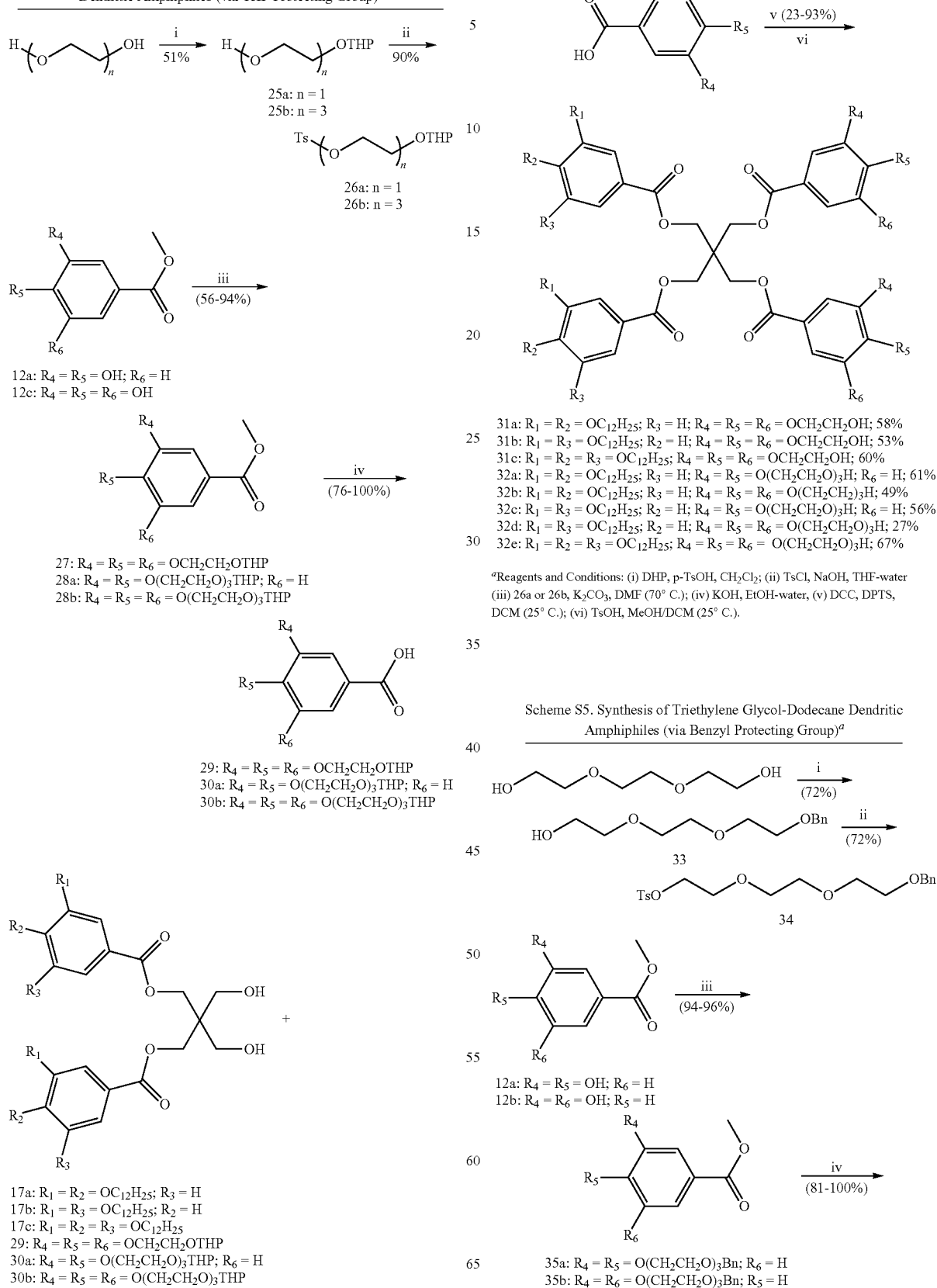

33

-continued

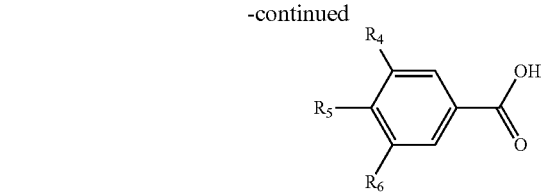

36a: $R_4 = R_5 = O(CH_2CH_2O)_3Bn$; $R_6 = H$
36b: $R_4 = R_6 = O(CH_2CH_2O)_3Bn$; $R_5 = H$

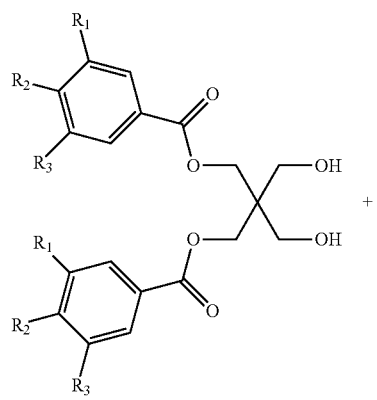

17a: $R_1 = R_2 = OC_{12}H_{25}$; $R_3 = H$
17b: $R_1 = R_3 = OC_{12}H_{25}$; $R_2 = H$
17c: $R_1 = R_2 = R_3 = OC_{12}H_{25}$
36a: $R_4 = R_5 = O(CH_2CH_2O)_3Bn$; $R_6 = H$
36b: $R_4 = R_6 = O(CH_2CH_2O)_3Bn$; $R_5 = H$

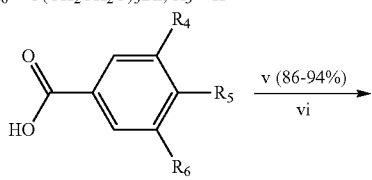

v (86-94%)
vi

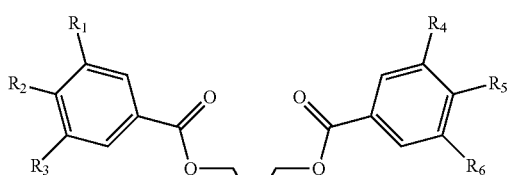

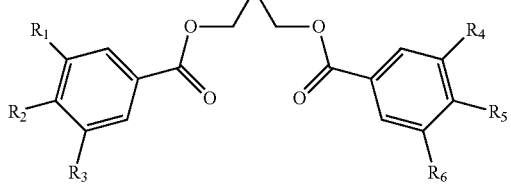

37a: $R_1 = R_2 = OC_{12}H_{25}$; $R_3 = H$; $R_4 = R_6 = O(CH_2CH_2O)_3H$; $R_5 = H$; 91%
37b: $R_1 = R_3 = OC_{12}H_{25}$; $R_2 = H$; $R_4 = R_6 = O(CH_2CH_2O)_3H$; $R_5 = H$; 93%
37c: $R_1 = R_2 = R_3 = OC_{12}H_{25}$; $R_4 = R_5 = O(CH_2CH_2O)_3H$; $R_6 = H$; 83%
37d: $R_1 = R_2 = R_3 = OC_{12}H_{25}$; $R_4 = R_6 = O(CH_2CH_2O)_3H$; $R_5 = H$; 75%

[a]Reagents and Conditions: (i) 50% NaOH, BnBr (100° C.); (ii) TsCl, NaOH, THF-water; (iii) 34, $K_2CO_3$, DMF (80° C.); (iv) KOH, EtOH-water (80° C.), (v) DCC, DPTS, DCM (25° C.); (vi) $H_2$, Pd/C, MeOH/DCM (25° C.).

34

Scheme S6: Synthesis of Triethylene Glycol-Butane/Hexane/Octane/2-Ethyl Hexane Dendritic Amphiphiles[a]

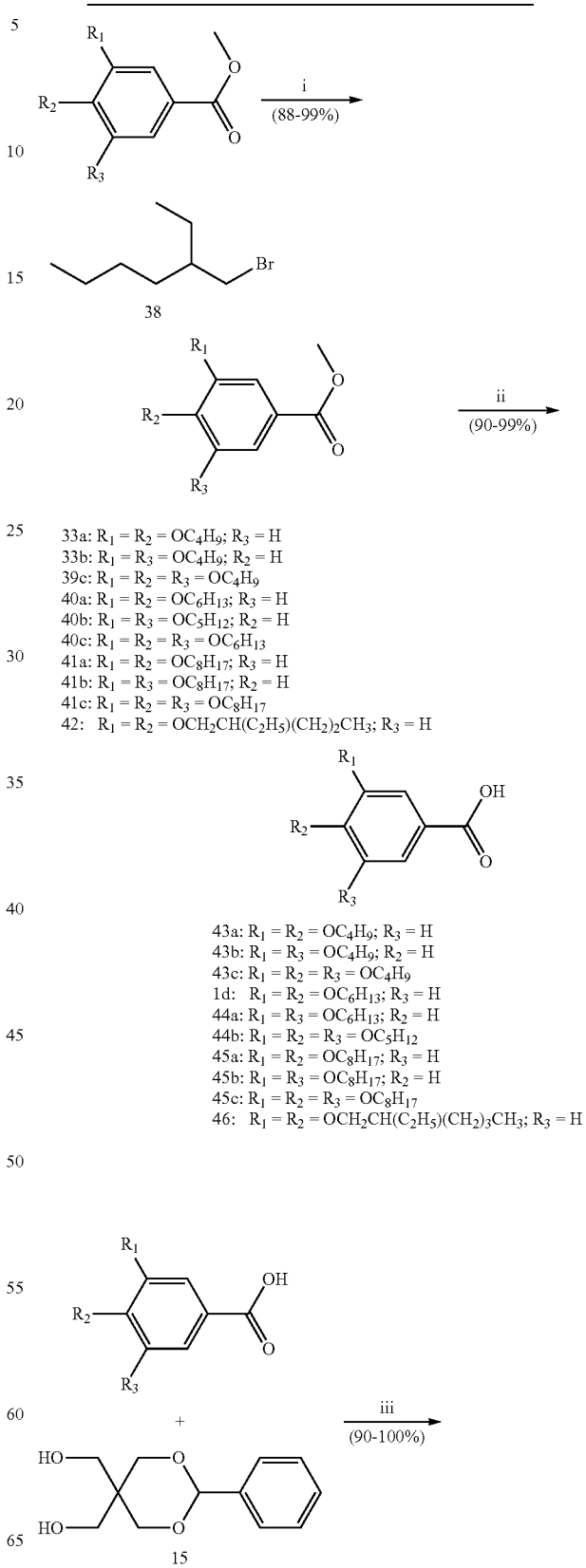

33a: $R_1 = R_2 = OC_4H_9$; $R_3 = H$
33b: $R_1 = R_3 = OC_4H_9$; $R_2 = H$
39c: $R_1 = R_2 = R_3 = OC_4H_9$
40a: $R_1 = R_2 = OC_6H_{13}$; $R_3 = H$
40b: $R_1 = R_3 = OC_5H_{12}$; $R_2 = H$
40c: $R_1 = R_2 = R_3 = OC_6H_{13}$
41a: $R_1 = R_2 = OC_8H_{17}$; $R_3 = H$
41b: $R_1 = R_3 = OC_8H_{17}$; $R_2 = H$
41c: $R_1 = R_2 = R_3 = OC_8H_{17}$
42: $R_1 = R_2 = OCH_2CH(C_2H_5)(CH_2)_2CH_3$; $R_3 = H$

43a: $R_1 = R_2 = OC_4H_9$; $R_3 = H$
43b: $R_1 = R_3 = OC_4H_9$; $R_2 = H$
43c: $R_1 = R_2 = R_3 = OC_4H_9$
1d: $R_1 = R_2 = OC_6H_{13}$; $R_3 = H$
44a: $R_1 = R_3 = OC_6H_{13}$; $R_2 = H$
44b: $R_1 = R_2 = R_3 = OC_5H_{12}$
45a: $R_1 = R_2 = OC_8H_{17}$; $R_3 = H$
45b: $R_1 = R_3 = OC_8H_{17}$; $R_2 = H$
45c: $R_1 = R_2 = R_3 = OC_8H_{17}$
46: $R_1 = R_2 = OCH_2CH(C_2H_5)(CH_2)_3CH_3$; $R_3 = H$

15

35
-continued

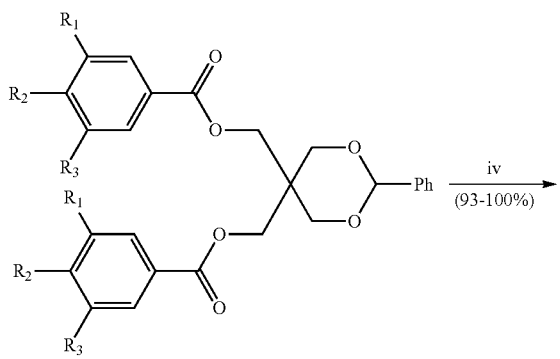

47a: $R_1 = R_2 = OC_4H_9$; $R_3 = H$
47b: $R_1 = R_3 = OC_4H_9$; $R_2 = H$
47c: $R_1 = R_2 = R_3 = OC_4H_9$
48a: $R_1 = R_2 = OC_5H_{12}$; $R_3 = H$
48b: $R_1 = R_3 = OC_6H_{13}$; $R_2 = H$
48c: $R_1 = R_2 = R_3 = OC_5H_{12}$
49a: $R_1 = R_2 = OC_8H_{17}$; $R_3 = H$
49b: $R_1 = R_3 = OC_8H_{17}$; $R_2 = H$
49c: $R_1 = R_2 = R_3 = OC_8H_{17}$
50:  $R_1 = R_2 = OCH_2CH(C_2H_5)(CH_2)_3CH_3$; $R_3 = H$

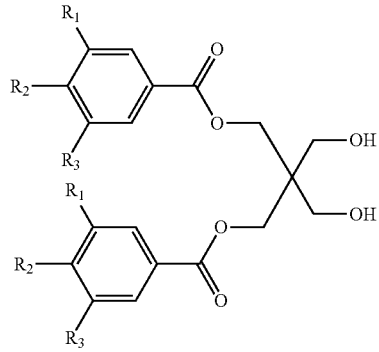

51a: $R_1 = R_2 = OC_4H_9$; $R_3 = H$
51b: $R_1 = R_3 = OC_4H_9$; $R_2 = H$
51c: $R_1 = R_2 = R_3 = OC_4H_9$
52a: $R_1 = R_2 = OC_6H_{13}$; $R_3 = H$
52b: $R_1 = R_3 = OC_5H_{13}$; $R_2 = H$
52c: $R_1 = R_2 = R_3 = OC_6H_{13}$
53a: $R_1 = R_2 = OC_8H_{17}$; $R_3 = H$
53b: $R_1 = R_3 = OC_8H_{17}$; $R_2 = H$
53c: $R_1 = R_2 = R_3 = OC_8H_{17}$
54:  $R_1 = R_2 = OCH_2CH(C_2H_5)(CH_2)_3CH_3$; $R_3 = H$

36
-continued

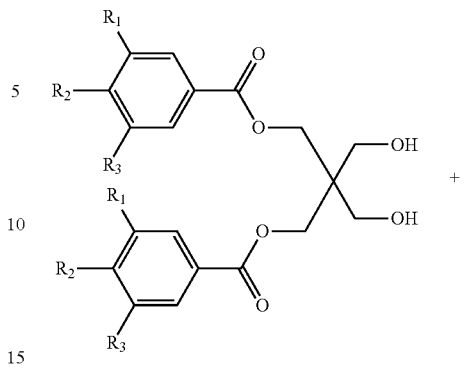

51a: $R_1 = R_2 = OC_4H_9$; $R_3 = H$
51b: $R_1 = R_3 = OC_4H_9$; $R_2 = H$
51c: $R_1 = R_2 = R_3 = OC_4H_9$
52a: $R_1 = R_2 = OC_6H_{13}$; $R_3 = H$
52b: $R_1 = R_3 = OC_5H_{13}$; $R_2 = H$
52c: $R_1 = R_2 = R_3 = OC_6H_{13}$
53a: $R_1 = R_2 = OC_8H_{17}$; $R_3 = H$
53b: $R_1 = R_3 = OC_8H_{17}$; $R_2 = H$
53c: $R_1 = R_2 = R_3 = OC_8H_{17}$
54:  $R_1 = R_2 = OCH_2CH(C_2H_5)(CH_2)_3CH_3$; $R_3 = H$
14a: $R_4 = R_5 = O(CH_2CH_2O)_3Me$; $R_6 = H$
14b: $R_4 = R_6 = O(CH_2CH_2O)_3Me$; $R_5 = H$
14c: $R_4 = R_5 = R_6 = O(CH_2CH_2O)_3Me$

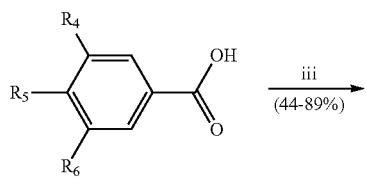

55a: $R_1 = R_2 = OC_4H_9$; $R_3 = H$; $R_4 = R_5 = O(CH_2CH_2O)_3Me$; $R_6 = H$; 86%
55b: $R_1 = R_3 = OC_4H_9$; $R_2 = H$; $R_4 = R_6 = O(CH_2CH_2O)_3Me$; $R_5 = H$; 89%
55c: $R_1 = R_2 = OC_4H_9$; $R_3 = H$; $R_4 = R_5 = R_6 = O(CH_2CH_2O)_2Me$; 85%
55d: $R_1 = R_3 = OC_4H_9$; $R_2 = H$; $R_4 = R_5 = O(CH_2CH_2O)_3Me$; $R_6 = H$; 80%
55e: $R_1 = R_3 = OC_4H_9$; $R_2 = H$; $R_4 = R_6 = O(CH_2CH_2O)_3Me$; $R_5 = H$; 75%
55f: $R_1 = R_3 = OC_4H_9$; $R_2 = H$; $R_4 = R_5 = R_6 = O(CH_2CH_2O)_3Me$; 53%
55g: $R_1 = R_2 = R_3 = OC_4H_9$; $R_4 = R_5 = O(CH_2CH_2O)_3Me$; $R_6 = H$; 81%
55h: $R_1 = R_2 = R_3 = OC_4H_9$; $R_4 = R_6 = O(CH_2CH_2O)_3Me$; $R_5 = H$; 89%
55i: $R_1 = R_2 = R_3 = OC_4H_9$; $R_4 = R_5 = R_6 = O(CH_2CH_2O)_3Me$; 91%
56a: $R_1 = R_2 = OC_6H_{13}$; $R_3 = H$; $R_4 = R_5 = O(CH_2CH_2O)_3Me$; $R_6 = H$; 69%
56b: $R_1 = R_3 = OC_6H_{13}$; $R_2 = H$; $R_4 = R_6 = O(CH_2CH_2O)_3Me$; $R_5 = H$; 73%
56c: $R_1 = R_2 = OC_6H_{13}$; $R_3 = H$; $R_4 = R_5 = R_6 = O(CH_2CH_2O)_2Me$; 64%
56d: $R_1 = R_3 = OC_6H_{13}$; $R_2 = H$; $R_4 = R_5 = O(CH_2CH_2O)_3Me$; $R_6 = H$; 75%
56e: $R_1 = R_3 = OC_6H_{13}$; $R_2 = H$; $R_4 = R_6 = O(CH_2CH_2O)_3Me$; $R_5 = H$; 83%
56f: $R_1 = R_3 = OC_6H_{13}$; $R_2 = H$; $R_4 = R_5 = R_6 = O(CH_2CH_2O)_3Me$; 47%
56g: $R_1 = R_2 = R_3 = OC_6H_{13}$; $R_4 = R_5 = O(CH_2CH_2O)_3Me$; $R_6 = H$; 44%
56h: $R_1 = R_2 = R_3 = OC_6H_{13}$; $R_4 = R_6 = O(CH_2CH_2O)_3Me$; $R_5 = H$; 67%
56i: $R_1 = R_2 = R_3 = OC_6H_{13}$; $R_4 = R_5 = R_6 = O(CH_2CH_2O)_3Me$; 30%

-continued

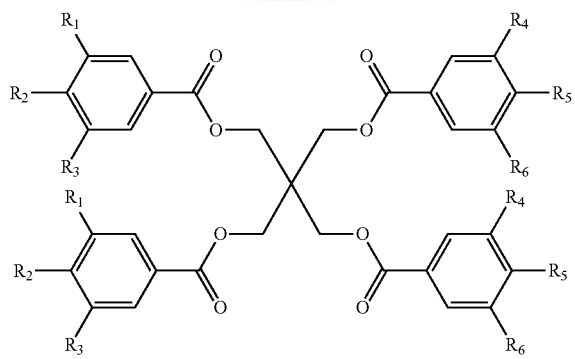

57a: $R_1 = R_2 = OC_8H_{17}$; $R_3 = H$; $R_4 = R_5 = O(CH_2CH_2O)_3Me$; $R_6 = H$; 69%
57b: $R_1 = R_2 = OC_8H_{17}$; $R_3 = H$; $R_4 = R_6 = O(CH_2CH_2O)_3Me$; $R_5 = H$; 88%
57c: $R_1 = R_2 = OC_8H_{17}$; $R_3 = H$; $R_4 = R_5 = R_6 = O(CH_2CH_2O)_3Me$; 88%
57d: $R_1 = R_3 = OC_8H_{17}$; $R_2 = H$; $R_4 = R_5 = O(CH_2CH_2O)_3Me$; $R_6 = H$; 85%
57e: $R_1 = R_3 = OC_8H_{17}$; $R_2 = H$; $R_4 = R_5 = O(CH_2CH_2O)_3Me$; $R_6 = H$; 82%
57f: $R_1 = R_3 = OC_8H_{17}$; $R_2 = H$; $R_4 = R_5 = R_6 = O(CH_2CH_2O)_3Me$; 67%
57g: $R_1 = R_2 = R_3 = OC_8H_{17}$; $R_4 = R_5 = O(CH_2CH_2O)_3Me$; $R_6 = H$; 87%
57h: $R_1 = R_2 = R_3 = OC_8H_{17}$; $R_4 = R_6 = O(CH_2CH_2O)_3Me$; $R_5 = H$; 63%
57i: $R_1 = R_2 = R_3 = OC_8H_{17}$; $R_4 = R_5 = R_6 = O(CH_2CH_2O)_3Me$; 73%
58a: $R_1 = R_2 = OCH_2CH(C_2H_5)(CH_2)_3CH_3$; $R_4 = H$; $R_4 = R_5 = O(CH_2CH_2O)_3Me$; $R_6 = H$; 81%
58b: $R_1 = R_2 = OCH_2CH(C_3H_6)(CH_2)_3CH_3$; $R_3 = H$; $R_4 = R_5 = R_6 = O(CH_2CH_2O)_3Me$; 59%

[a]Reagents and Conditions: (i) $C_4H_9Br$, $C_6H_{13}Br$, $C_8H_{17}Br$, or 38, $K_2CO_3$, DMF (75° C.); (ii) KOH, EtOH-Water (60° C.); (iii) DCC, DTPS, DCM (25° C.); (iv) $H_2$, Pd/C, MeOH/DCM (25° C.).

Scheme S7: Synthesis of Glycerol-Dodecane Dendritic Amphiphiles[a]

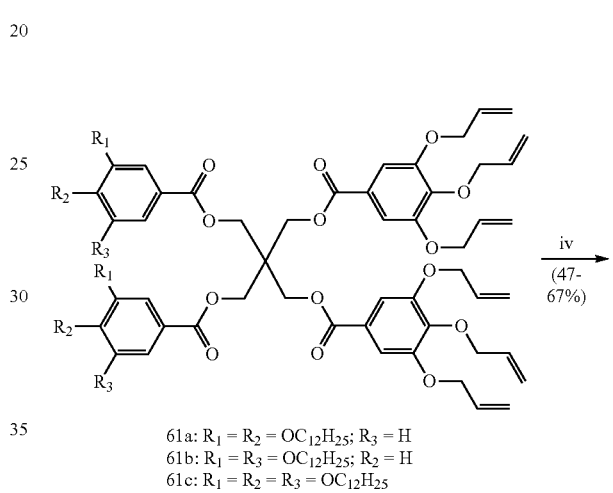

-continued

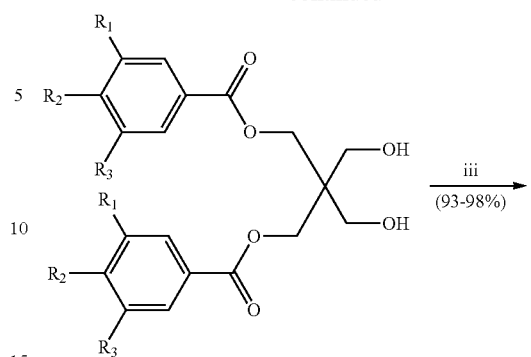

17a: $R_1 = R_2 = OC_{12}H_{25}$; $R_3 = H$
17b: $R_1 = R_3 = OC_{12}H_{25}$; $R_2 = H$
17c: $R_1 = R_2 = R_3 = OC_{12}H_{25}$

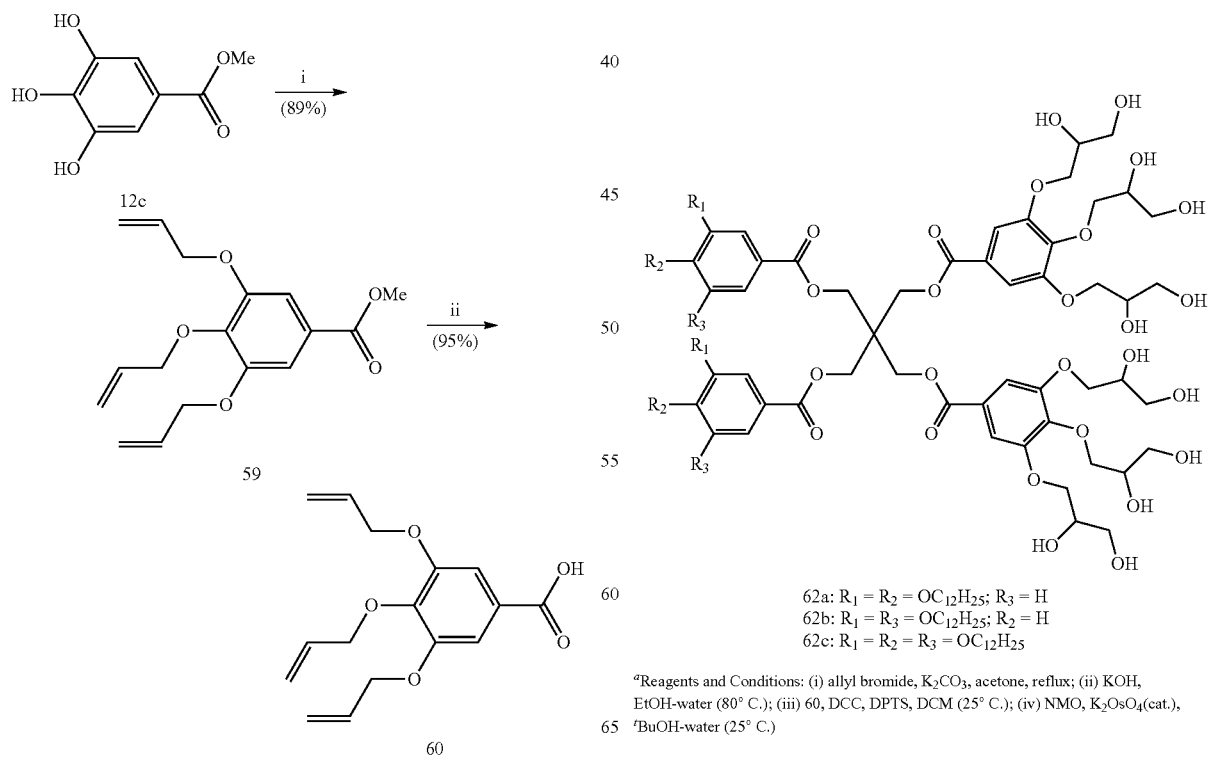

61a: $R_1 = R_2 = OC_{12}H_{25}$; $R_3 = H$
61b: $R_1 = R_3 = OC_{12}H_{25}$; $R_2 = H$
61c: $R_1 = R_2 = R_3 = OC_{12}H_{25}$

62a: $R_1 = R_2 = OC_{12}H_{25}$; $R_3 = H$
62b: $R_1 = R_3 = OC_{12}H_{25}$; $R_2 = H$
62c: $R_1 = R_2 = R_3 = OC_{12}H_{25}$

[a]Reagents and Conditions: (i) allyl bromide, $K_2CO_3$, acetone, reflux; (ii) KOH, EtOH-water (80° C.); (iii) 60, DCC, DPTS, DCM (25° C.); (iv) NMO, $K_2OsO_4$(cat.), [t]BuOH-water (25° C.)

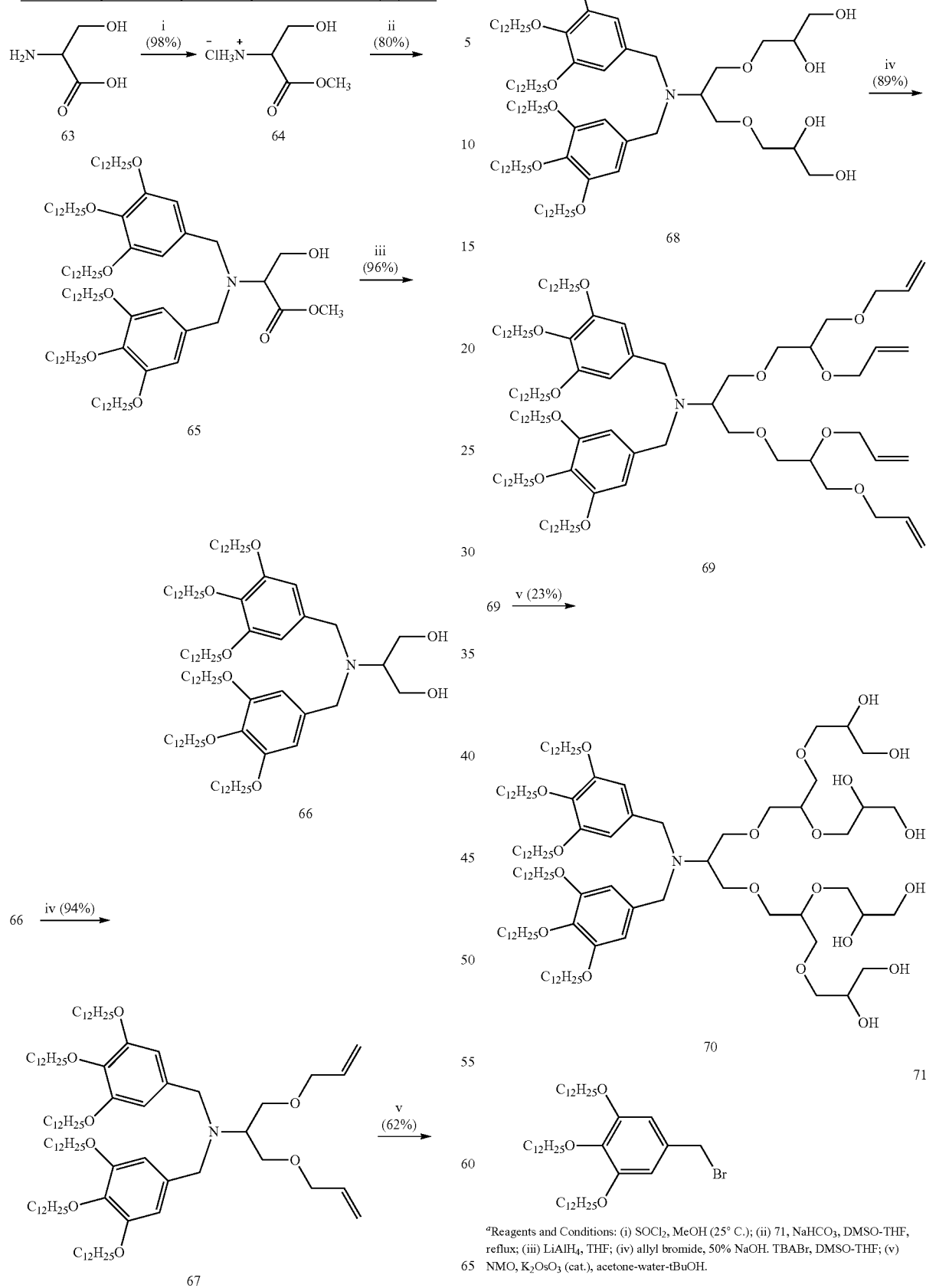
Scheme S8. Synthesis of Glycerol-Benzylamine Dendritic Amphiphiles[a]
[a]Reagents and Conditions: (i) SOCl$_2$, MeOH (25° C.); (ii) 71, NaHCO$_3$, DMSO-THF, reflux; (iii) LiAlH$_4$, THF; (iv) allyl bromide, 50% NaOH. TBABr, DMSO-THF; (v) NMO, K$_2$OsO$_3$ (cat.), acetone-water-tBuOH.

Scheme S9. Synthesis of (3,4,5)12G1-PE-(3,4,5)-1EO-G1-(OH)$_3$.

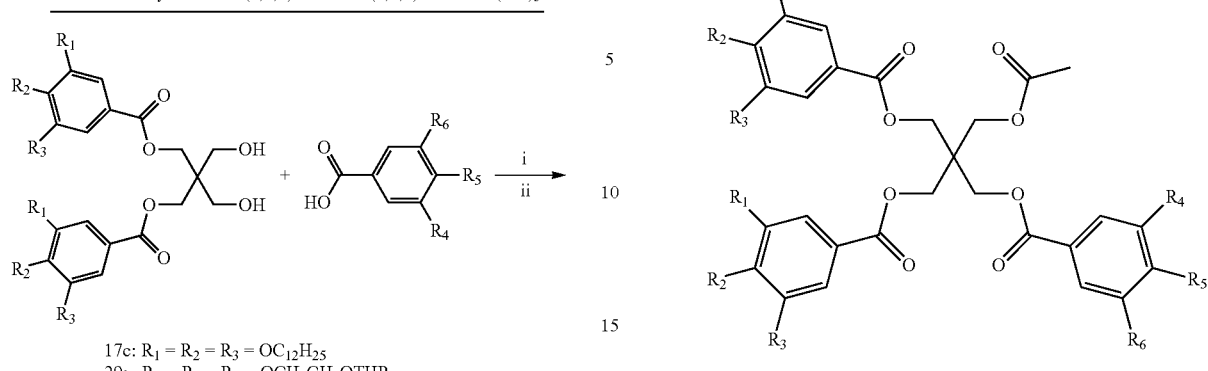

17c: $R_1 = R_2 = R_3 = OC_{12}H_{25}$
29: $R_4 = R_5 = R_6 = OCH_2CH_2OTHP$

72: $R_1 = R_2 = R_3 = OC_{12}H_{25}$; $R_4 = R_5 = R_6 = OCH_2CH_2OH$; 70%

[a]Reagents and Conditions: (i) DCC, DPTS, AcOH, DCM (25° C.); (ii) TSOH, MeOH/DCM (25° C.).

Scheme S10. Synthesis of Thioglycerol-Benzylether Dendritic Amphiphiles[a]

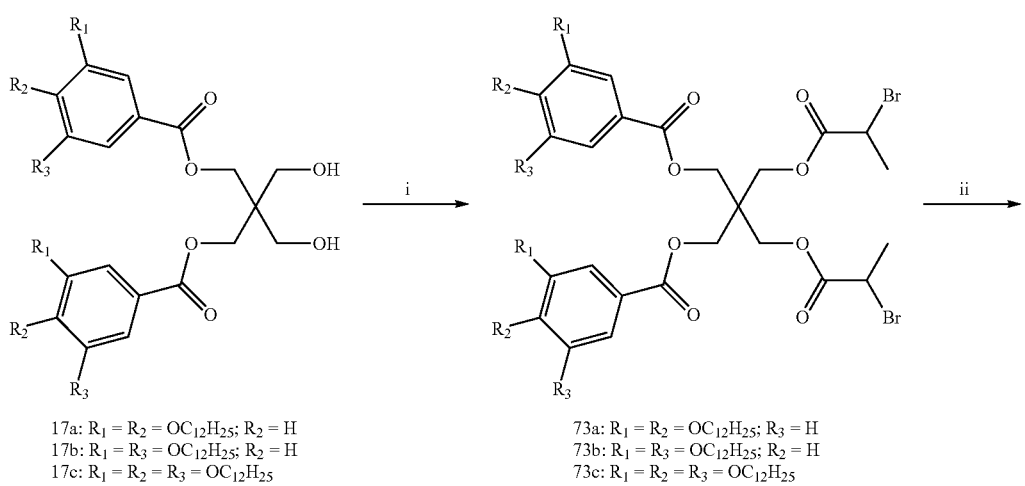

17a: $R_1 = R_2 = OC_{12}H_{25}$; $R_3 = H$
17b: $R_1 = R_3 = OC_{12}H_{25}$; $R_2 = H$
17c: $R_1 = R_2 = R_3 = OC_{12}H_{25}$

73a: $R_1 = R_2 = OC_{12}H_{25}$; $R_3 = H$
73b: $R_1 = R_3 = OC_{12}H_{25}$; $R_2 = H$
73c: $R_1 = R_2 = R_3 = OC_{12}H_{25}$

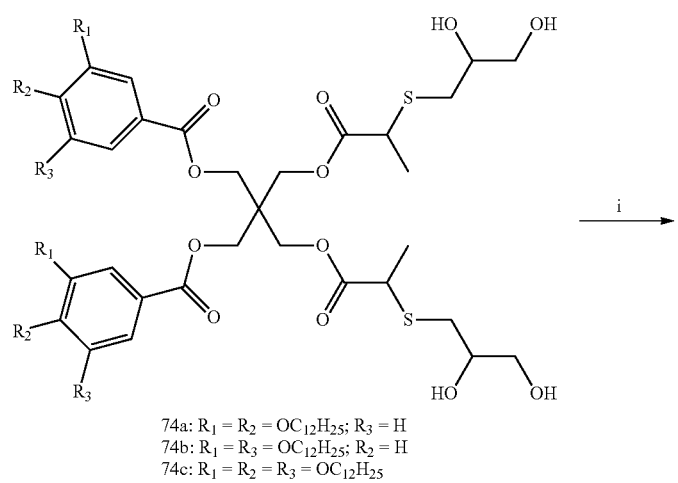

74a: $R_1 = R_2 = OC_{12}H_{25}$; $R_3 = H$
74b: $R_1 = R_3 = OC_{12}H_{25}$; $R_2 = H$
74c: $R_1 = R_2 = R_3 = OC_{12}H_{25}$

-continued
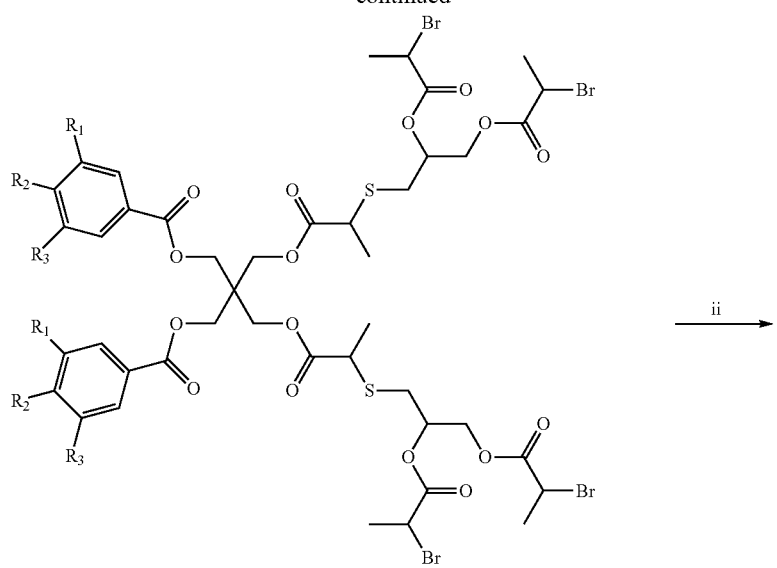
75a: R₁ = R₂ = OC₁₂H₂₅; R₃ = H
75b: R₁ = R₃ = OC₁₂H₂₅; R₂ = H
75c: R₁ = R₂ = R₃ = OC₁₂H₂₅
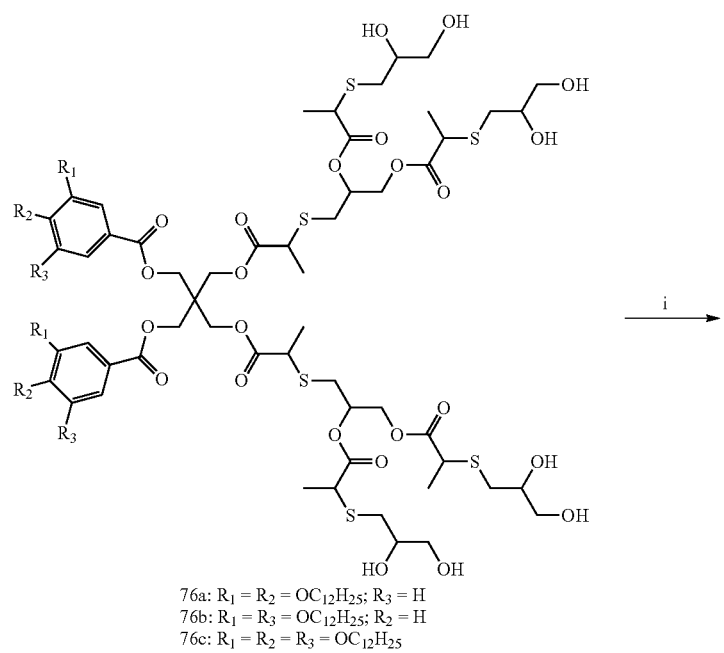
76a: R₁ = R₂ = OC₁₂H₂₅; R₃ = H
76b: R₁ = R₃ = OC₁₂H₂₅; R₂ = H
76c: R₁ = R₂ = R₃ = OC₁₂H₂₅
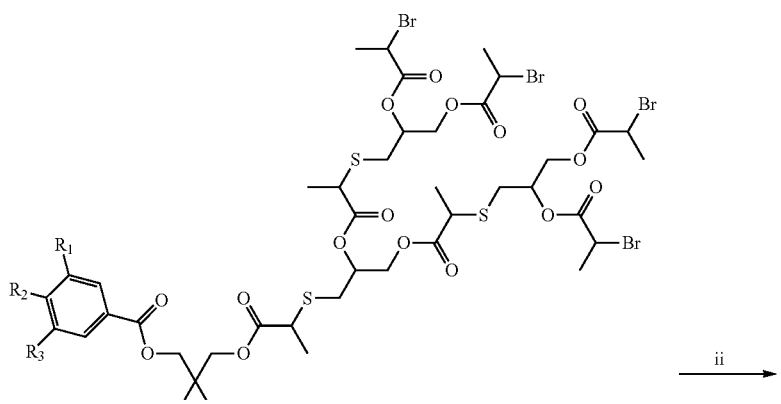

-continued
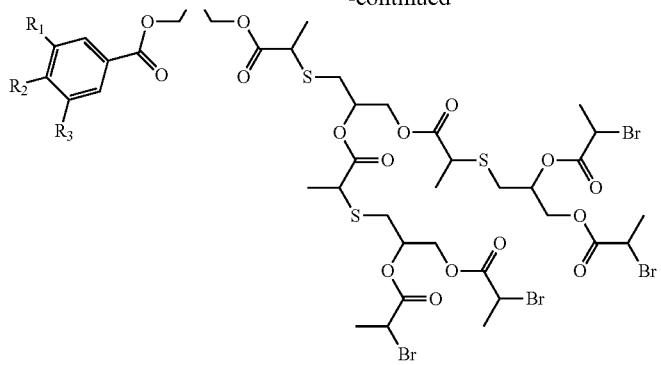
77a: $R_1 = R_2 = OC_{12}H_{25}$; $R_3 = H$
77b: $R_1 = R_3 = OC_{12}H_{25}$; $R_2 = H$
77c: $R_1 = R_2 = R_3 = OC_{12}H_{25}$
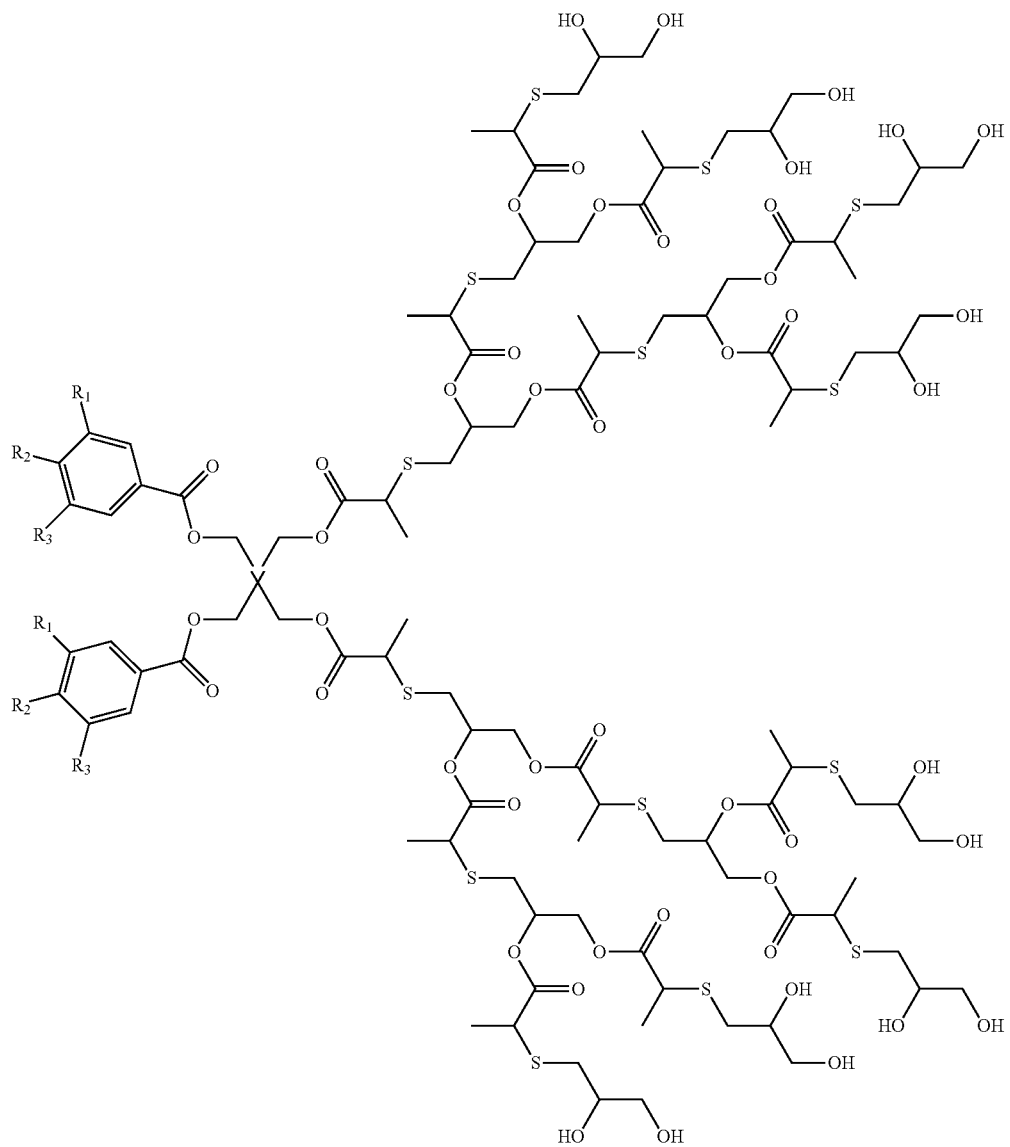
78a: $R_1 = R_2 = OC_{12}H_{25}$; $R_3 = H$
78b: $R_1 = R_3 = OC_{12}H_{25}$; $R_2 = H$
78c: $R_1 = R_2 = R_3 = OC_{12}H_{25}$
[a]Reagents and Conditions: (i) Bromopropionyl bromide, pyridine, $CH_2Cl_2$; (ii) -Thioglycerol, $Et_3N$, MeCN—$CH_2Cl_2$.

Scheme S11. Synthesis of diacetal (3,5)12G1-dAc-(3,4,5)-3EO-G1-(OCH3)3[a]
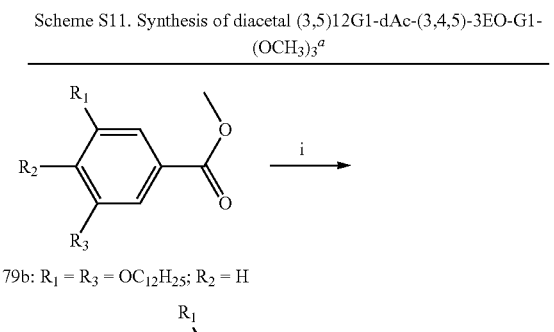
[a]Reagents and Conditions: (i) LiAlH4, THF; (ii) Dess-Martin Periodinane, DCM; (iii) pentaerythritol, TsOH, benzene/DMF, reflux; (iv) TsOH, benzene/DMF, reflux.
Scheme S12. Synthesis of Polyester-Alkyl Tail Dendritic Amphiphiles[a]
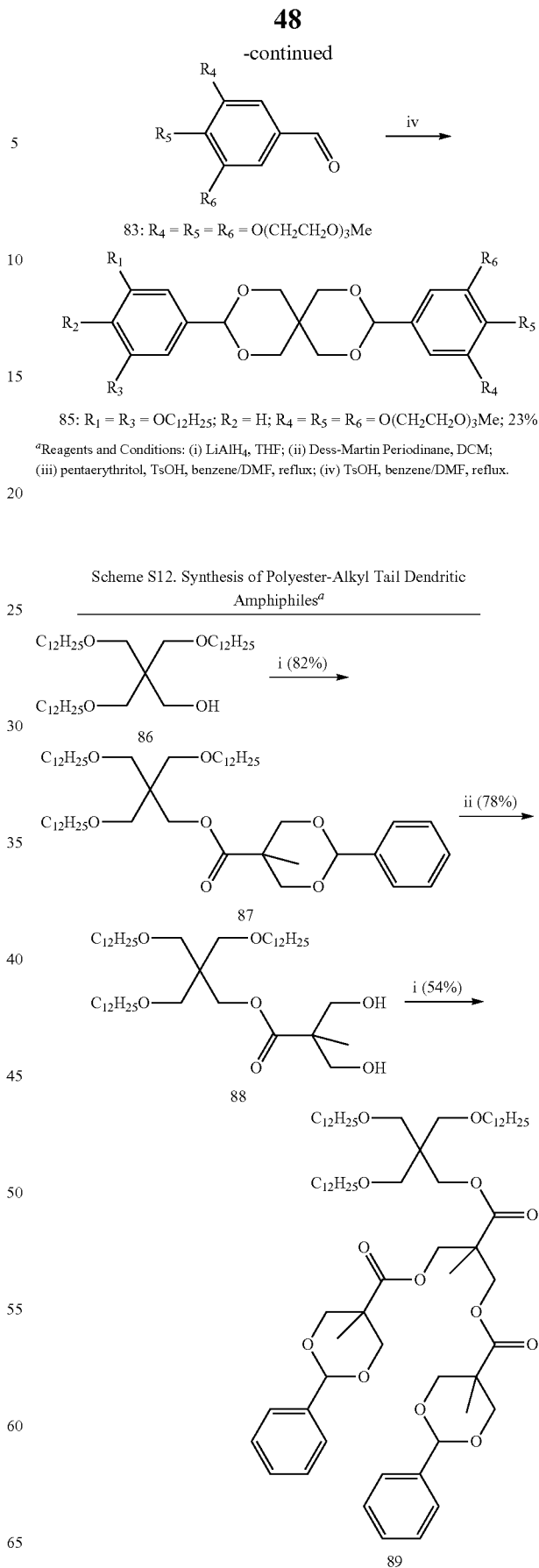

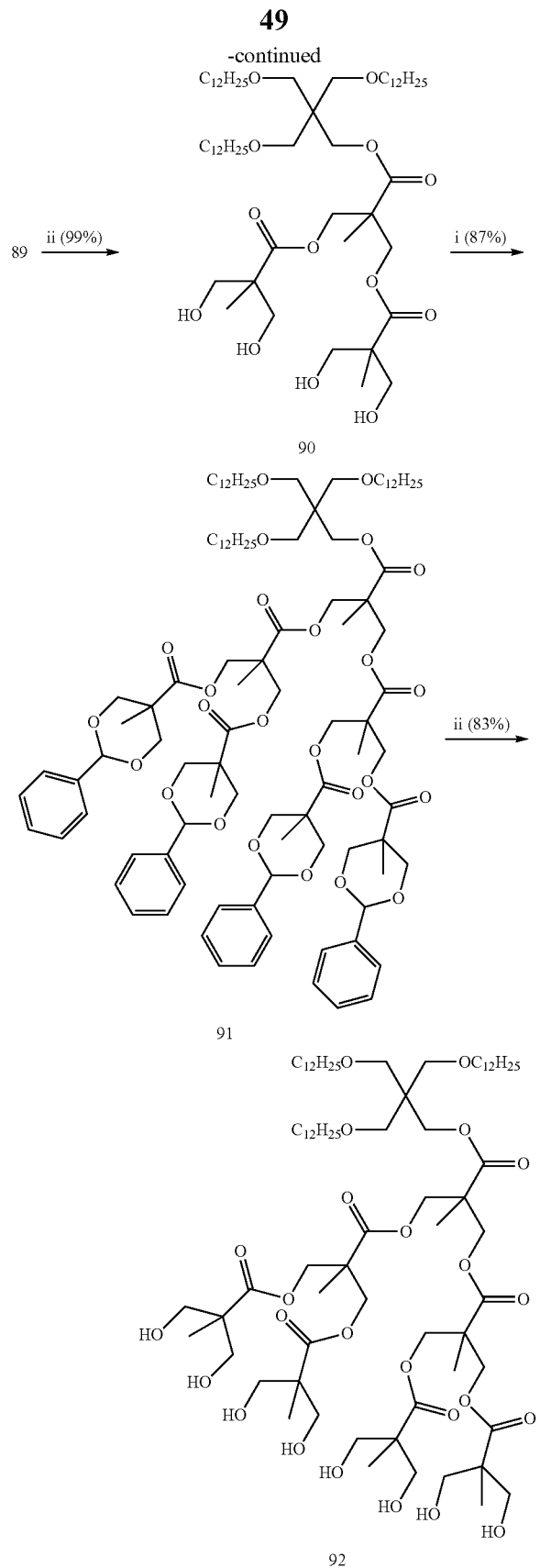

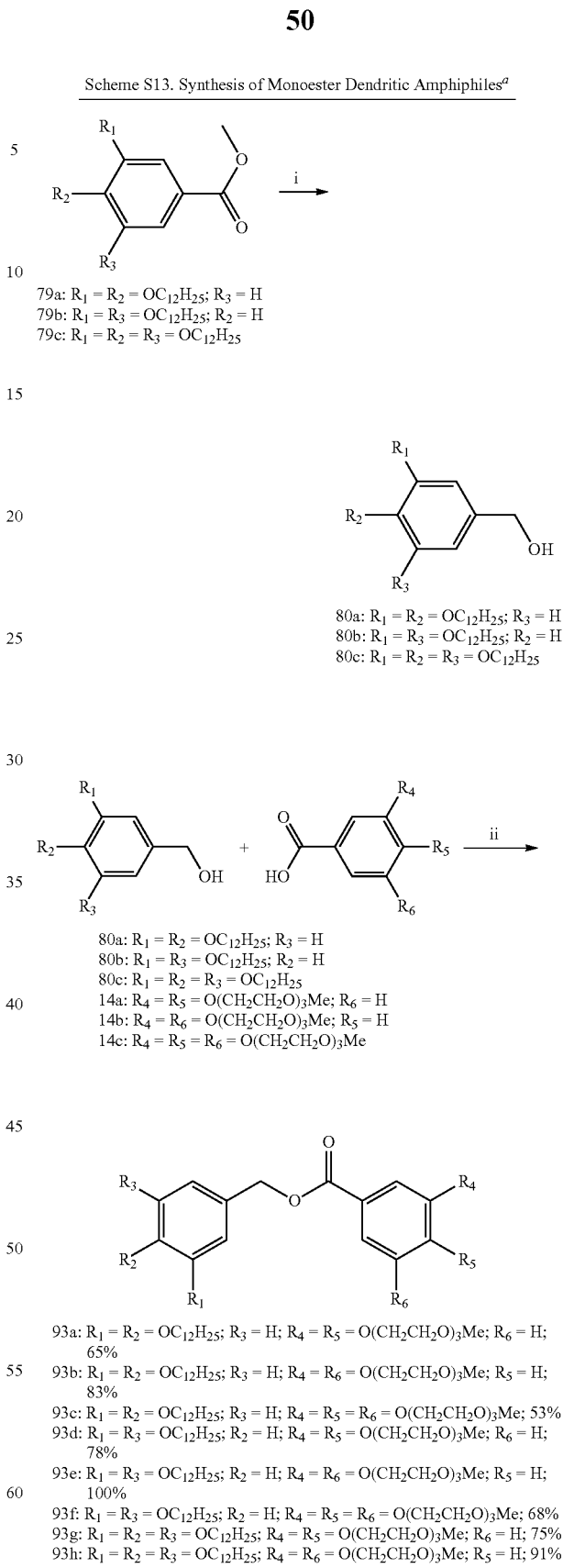

Scheme S13. Synthesis of Monoester Dendritic Amphiphiles[a]

79a: $R_1 = R_2 = OC_{12}H_{25}$; $R_3 = H$
79b: $R_1 = R_3 = OC_{12}H_{25}$; $R_2 = H$
79c: $R_1 = R_2 = R_3 = OC_{12}H_{25}$

80a: $R_1 = R_2 = OC_{12}H_{25}$; $R_3 = H$
80b: $R_1 = R_3 = OC_{12}H_{25}$; $R_2 = H$
80c: $R_1 = R_2 = R_3 = OC_{12}H_{25}$

80a: $R_1 = R_2 = OC_{12}H_{25}$; $R_3 = H$
80b: $R_1 = R_3 = OC_{12}H_{25}$; $R_2 = H$
80c: $R_1 = R_2 = R_3 = OC_{12}H_{25}$
14a: $R_4 = R_5 = O(CH_2CH_2O)_3Me$; $R_6 = H$
14b: $R_4 = R_6 = O(CH_2CH_2O)_3Me$; $R_5 = H$
14c: $R_4 = R_5 = R_6 = O(CH_2CH_2O)_3Me$

93a: $R_1 = R_2 = OC_{12}H_{25}$; $R_3 = H$; $R_4 = R_5 = O(CH_2CH_2O)_3Me$; $R_6 = H$; 65%
93b: $R_1 = R_2 = OC_{12}H_{25}$; $R_3 = H$; $R_4 = R_6 = O(CH_2CH_2O)_3Me$; $R_5 = H$; 83%
93c: $R_1 = R_2 = OC_{12}H_{25}$; $R_3 = H$; $R_4 = R_5 = R_6 = O(CH_2CH_2O)_3Me$; 53%
93d: $R_1 = R_3 = OC_{12}H_{25}$; $R_2 = H$; $R_4 = R_5 = O(CH_2CH_2O)_3Me$; $R_6 = H$; 78%
93e: $R_1 = R_3 = OC_{12}H_{25}$; $R_2 = H$; $R_4 = R_6 = O(CH_2CH_2O)_3Me$; $R_5 = H$; 100%
93f: $R_1 = R_3 = OC_{12}H_{25}$; $R_2 = H$; $R_4 = R_5 = R_6 = O(CH_2CH_2O)_3Me$; 68%
93g: $R_1 = R_2 = R_3 = OC_{12}H_{25}$; $R_4 = R_5 = O(CH_2CH_2O)_3Me$; $R_6 = H$; 75%
93h: $R_1 = R_2 = R_3 = OC_{12}H_{25}$; $R_4 = R_6 = O(CH_2CH_2O)_3Me$; $R_5 = H$; 91%
93i: $R_1 = R_2 = R_3 = OC_{12}H_{25}$; $R_4 = R_5 = R_6 = O(CH_2CH_2O)_3Me$; 88%

[a]Reagents and Conditions: (i)₁₀, DMAP, py-DCM (25° C.); (ii) H₂, Pd/C, MeOH-DCM (25° C.)

[a]Reagents and Conditions: (i) LiAlH₄, THF; (ii) DCC, DPTS, DCM (25° C.).

Scheme S14. Synthesis of Phenylamide Dendritic Amphiphiles with Monomethylated Triethylene Glycol Tails[a]
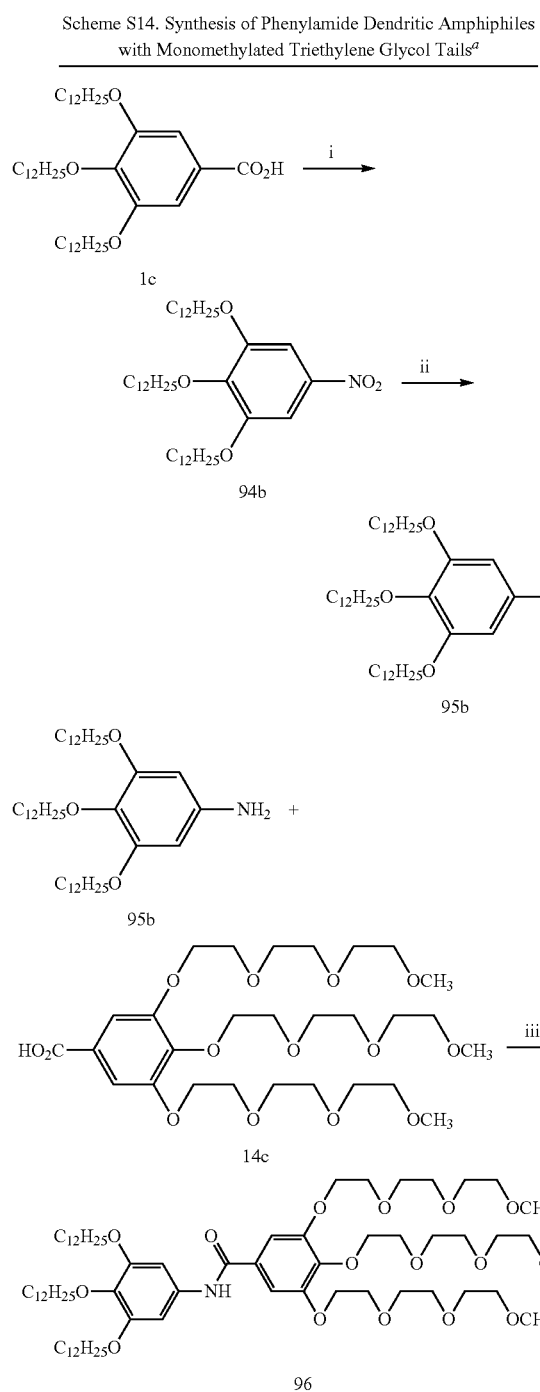
[a]Reagents and Conditions: HNO₃, AIBN(cat.), CH₃CN, 50° C.; (ii)NH₂—NH₂, graphite, EtOH, reflux; (iii) DCC, DPTS, CH₂Cl₂
Scheme S15. Synthesis of Phenylamide Dendritic Amphiphiles with Ammonium Salt Tails[a]
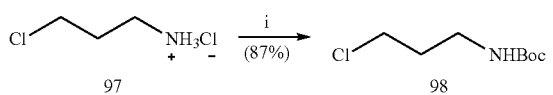
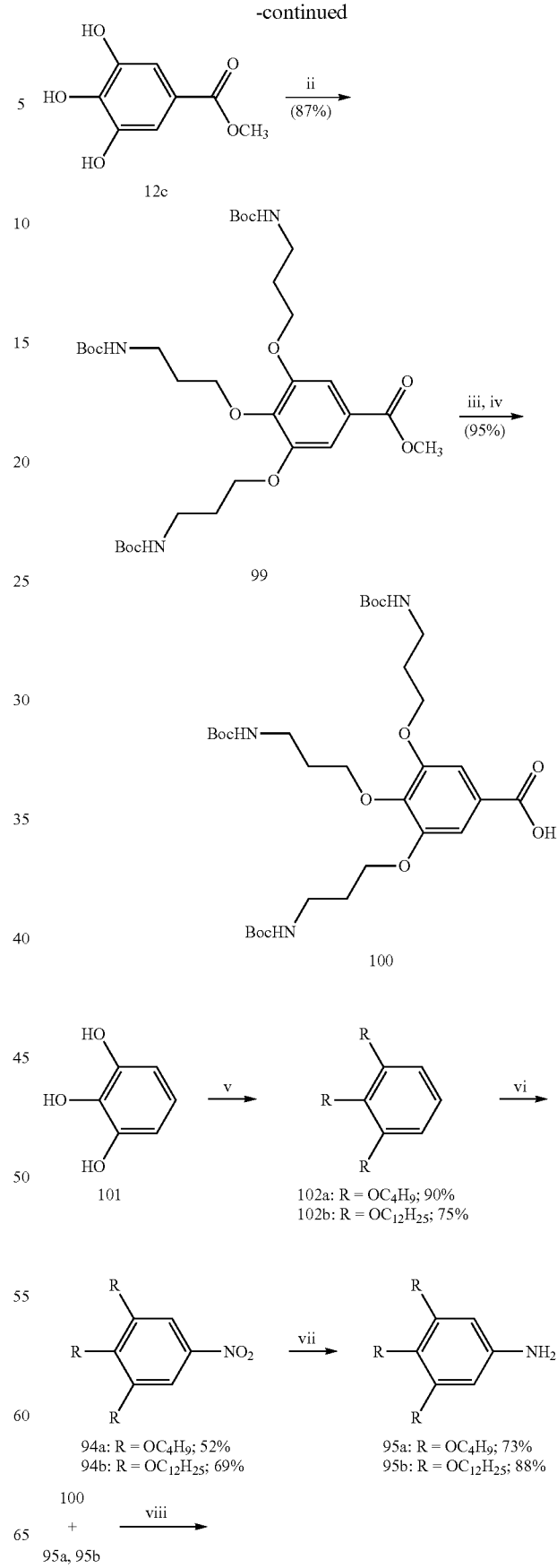

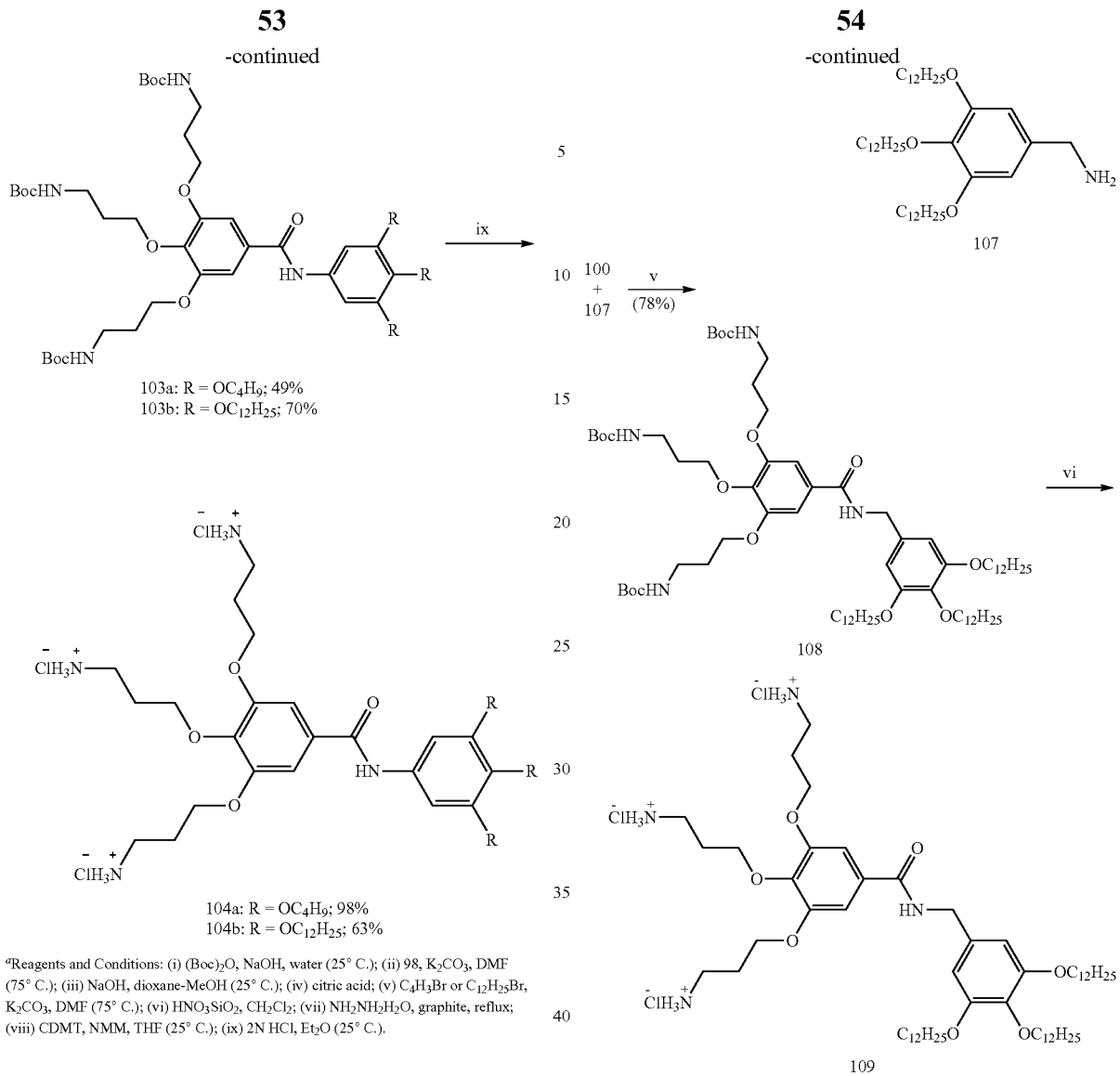

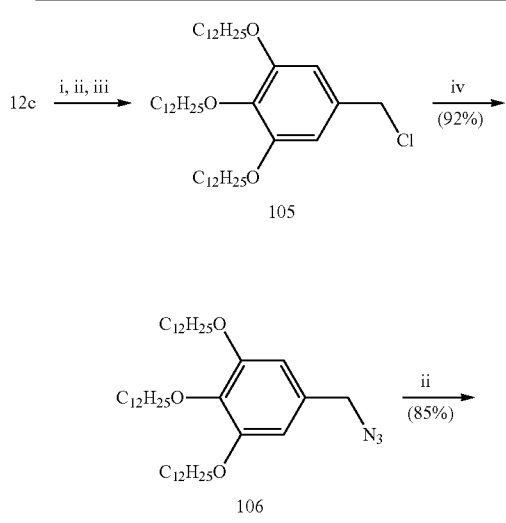

Scheme S16. Synthesis of Benzylamide Dendritic Amphiphiles with Ammonium Salt Tails[a]

Synthesis of Janus-Dendrimers

The synthesis and characterization of (3,4)-bis-dodecylbenzoic acid (1a), (3,5)-Bis-dodecylbenzoic acid (1b), (3,4,5)-tris-dodecylbenzoic acid (1c), $(OH)_2$—PE-(acetonide)$_2$ (2), (3,4)12G1-PE-BMPA-G1-$(OH)_4$ (4a), (3,5)12G1-PE-BMPA-G1-$(OH)_4$ (4b), (3,4,5)12G1-PE-BMPA-G1-$(OH)_4$ (4c), (3,4)12G1-PE-BMPA-G2-$(OH)_8$ (6a), (3,5)12G1-PE-BMPA-G2-$(OH)_8$ (6b), (3,4,5)12G1-PE-BMPA-G2-$(OH)_8$ (6c) were prepared according to literature procedures (Percec, Chem. Eur. J. 5, 1070-1083 (1999)). The synthesis of 4-(dimethylamino) pyridinium p-toluenesulfonate (DPTS) has been described previously. Dess-Martin periodinane, and 2-chloro-4,6-dimethoxy-1,3,5-triazine (CDMT)50 have been described previously. Isopropylidene-2,2-bis(methoxy) propionic anhydride (9) and benzylidene-2,2-bis(oxymethyl) propionic anhydride (10) were synthesized according to literature procedures. Monobenzylidene pentaerythritol (15) was prepared according to a literature procedure. The synthesis of ethyleneglycol monotetrahydropyran monotosylate (26a) was described previously. Tri-O-dodecyl pentaerythritol (86) was prepared according to literature procedure46. The syntheses of (3,4-bis(dodecyloxy)phenyl) methanol (80a), and (3,4,5-tris(dodecyloxy)phenyl) methanol (80c) were described previously. The synthesis of diethylene glycol monotosylate was performed according to literature procedure. (D/L) Serine methyl ester HCl salt (64) was prepared according to literature procedure54. The synthesis of Ethylene glycol monomethylether monotosylate (11a), Diethylene glycol monomethylether monotosylate (11 b), and Triethylene glycol monomethylether monotosylate (11c) were performed according to the literature procedure (Ouchi, Bull. Chem. Soc. Jpn. 63, 1260-1262 (1990)).

(3,4)6G1-$CO_2$H (id): (3,4)6G1-$CO_2CH_3$ (40a) (9 g, 26.7 mmol) was dissolved in 95% EtOH (125 mL). KOH (7.5 g, 133.7 mmol) in water (75 mL) was added and the reaction mixture was stirred at reflux for 10 min. The reaction mixture was then cooled to rt, poured into water (200 mL) and acidified to pH=1 with 2 M HCl. The aqueous solution was extracted with ethyl acetate (4×75 mL). The ethyl acetate solution was washed with water (5×100 mL), brine (100 mL) and dried over $MgSO_4$ then filtered. Solvent was removed under reduce pressure, and the sample was dried under high vacuum overnight to afford a colorless oil: 8.61 g (97% yield). No further purification was necessary.

(3,4)16G1-CO2H (1e): (3,4)16G1-$CO2CH_3$ (1.65 g, 2.67 mmol) was suspended in 95% EtOH (35 mL mL). KOH (0.75 g, 13.4 mmol) in water (8 mL) was added and the reaction mixture stirred at reflux for 1 hour. The reaction mixture was then cooled to rt, poured into water (200 mL) and acidified to pH 1 with 2 M HCl. The aqueous solution was extracted with DCM (2×100 mL). The DCM solution was washed with water (3×100 mL) and dried over copious $MgSO_4$ then filtered. The solvent was removed using a rotary evaporator, and the sample was dried under high vacuum. The sample was purified by recrystallization from 2-propanol to afford a white solid: 0.6 g (42% yield).

(3,4)6G1-PE-BMPA-G1-(acetonide)$_2$ (3d):36 DCC (1.38 g, 6.69 mmole) was added into the solution of $(OH)_2$—PE-(acetonide)$_2$ (1.50 g, 3.34 mmole), (3,4)6G1-$CO_2$H (1d) (2.37 g, 7.36 mmole), and DPTS (0.98 g, 3.34 mmole) in dry $CH_2Cl_2$ (60 mL) and dry THF (15 mL). The reaction mixture was stirred at room temperature under $N_2$ atmosphere for 48 h. The urea was filtered off and washed with small amount of $CH_2Cl_2$ then the filtrate was concentrated and purified by column chromatography (silica gel; EtOAc:Hexane=20:80) to give (3,4)6G1-PE-(acetonide)$_2$ (3d) as a viscous oil: 1.97 (56%).

(3,4)16G1-PE-BMPA-(acetonide)$_2$ (3e): DCC (1.20 g, 5.80 mmole) was added into the solution of $(OH)_2$—PE-(acetonide)$_2$ (1.00 g, 2.23 mmole), (3,4)16G1-$CO_2$H (1e) (2.96 g, 4.91 mmole), and DPTS (0.66 g, 2.23 mmole) in dry $CH_2Cl_2$ (90 mL). The reaction mixture was stirred at room temperature under $N_2$ atmosphere for 48 h. The urea was filtered off and washed with a small amount of $CH_2Cl_2$ then the filtrate was concentrated and purified by column chromatography (silica gel; EtOAc:Hexane=20:80) to give (3,4) 16G1-PE-BMPA-(acetonide)$_2$ (3e) as a white solid: 2.23 (62%).

(3,4)6G1-PE-BMPA-G1-(OH)$_4$ (4d): (3,4)6G1-PE-BMPA-G1-(acetonide)$_2$ (3d) (1.75 g, 1.65 mmol) was dissolved in $CH_2Cl_2$ (15 mL) and diluted with MeOH (15 mL). 2 Teaspoons of Dowex 50W resin were added and the mixture was stirred at 50° C. for 19 h. The resin was filtered off, and washed with small amount of $CH_2Cl_2$. Filtrate was concentrated to give 1.55 g (96%) of white solid.

(3,4)16G1-PE-BMPA-G1-(OH)$_4$ (4e): (3,4)16G1-PE-BMPA-G1-(acetonide)$_2$ (3e) (2.03 g, 1.25 mmol) was dissolved in $CH_2Cl_2$ (15 mL) and diluted with MeOH (15 mL). 2 Teaspoons of Dowex 50W resin were added and the mixture was stirred at 50° C. for 19 h. The resin was filtered off, and washed with small amount of $CH_2Cl_2$. Filtrate was concentrated to give 1.86 g (97%) of white solid.

(3,4)6G1-PE-BMPA-G2-(acetonide)$_4$ (5d): (3,4)6G1-PE-BMPA-G1-(OH)$_4$ (4d) (0.93 g, 0.95 mmol), isopropylidene-2,2-bis(methoxy)propionic anhydride (1.63 g, 4.92 mmol) and 4-(dimethylamino) pyridine (DMAP) (69 mg, 0.75 mmol) were dissolved in dry pyridine (1.5 mL) and dry $CH_2Cl_2$ (6 mL) and stirred at room temperature for 68 h. Water was added with vigorous stirring for 2 h to quench the anhydride. The mixture was then diluted with 100 mL of $CH_2Cl_2$, and washed with 10% $NaHSO_4$, 10% $Na_2SO_4$, and brine succeedingly. The organic layer was dried over $MgSO_4$, and the solvent evaporated. The product was further purified by column chromatography (silica gel, EtOAc:Hexane=40:60) to give (3,4)6G1-PE-BMPA-G2-(acetonide)$_4$ (5d) as a glassy solid: 1.16 g (76%).

(3,4)16G1-PE-BMPA-G2-(acetonide)$_4$ (5e): (3,4)16G1-PE-BMPA-G1-(OH)$_4$ (4e) (1.23 g, 0.80 mmol), isopropylidene-2,2-bis(methoxy)propionic anhydride (1.38 g, 4.17 mmol) and 4-(dimethylamino) pyridine (DMAP) (59 mg, 0.48 mmol) were dissolved in dry pyridine (1.5 mL) and dry $CH_2Cl_2$ (6 mL) and stirred at room temperature for 68 h. Water was added with vigorous stirring for 2 h to quench the anhydride. The mixture was then diluted with 100 mL of $CH_2Cl_2$, and washed with 10% $NaHSO_4$, 10% $Na_2SO_4$, and brine succeedingly. The organic layer was dried over $MgSO_4$, and the solvent evaporated. The product was further purified by column chromatography (silica gel, EtOAc:Hexane=1:2) to give (3,4)16G1-PE-BMPA-G2-(acetonide)$_4$ (5e) as a white solid: 1.53 g (89%).

(3,4)6G1-PE-BMPA-G2-(OH)$_8$ (6d): (3,4)6G1-PE-BMPA-G2-(acetonide)$_4$ (5d) (0.99 g, 0.62 mmol) was dissolved in $CH_2Cl_2$ (15 mL) and diluted with MeOH (15 mL)). 2 Teaspoons of Dowex 50W resin were added and the mixture was stirred at 50° C. for 19 h. The resin was filtered off, and washed with small amount of $CH_2Cl_2$. The filtrate was concentrated to give 0.89 g (98%) of white solid.

(3,4)16G1-PE-BMPA-G2-(OH)$_8$ (6e): (3,4)16G1-PE-BMPA-G2-(acetonide)$_4$ (5e) (1.13 g, 0.52 mmol) was dissolved in $CH_2Cl_2$ (15 mL) and diluted with MeOH (15 mL).). 2 Teaspoons of Dowex 50W resin were added and the mixture was stirred at 50° C. for 19 h. The resin was filtered off, and washed with small amount of $CH_2Cl_2$. The filtrate was concentrated to give 0.76 g (73%) of white solid.

(3,4)12G1-PE-BMPA-G3-(benzylidene)$_8$ (7a): (3,4) 12G1-PE-BMPA-G2-(OH)$_8$ (6a) (0.20 g, 0.112 mmol) and 4-(dimethylamino) pyridine (DMAP) (40 mg, 0.29 mmol) were dissolved in dry pyridine (2 mL) and then diluted with dry $CH_2Cl_2$ (1 mL). Benzylidene-2,2-bis(oxymethyl)propionic anhydride (0.56 g, 1.69 mmol) in $CH_2Cl_2$ (5 mL) was added dropwise into the reaction mixture and stirred at room temperature overnight. After completion by monitoring from MALDI-TOF, the excess of anhydride was quenched by adding 5 mL of pyridine:water (1:1). The mixture was extracted with $CH_2Cl_2$, washed with $NaHSO_4$ (1M), $NaHCO_3$ (10%), and brine. The combined organic phase was dried over $MgSO_4$, concentrated, and purified by chromatography (silica gel, EtOAc/hexane=3:7) to give (3,4)-12-(acetonide)$_8$ as a white solid: 0.32 g, (84%).

(3,5)12G1-PE-BMPA-G3-(benzylidene)$_8$ (7b): (3,5) 12G1-PE-BMPA-G2-(OH)$_8$ (6b) (0.20 g, 0.11 mmol) and 4-(dimethylamino) pyridine (DMAP) (100 mg, 0.82 mmol) were dissolved in dry pyridine (2 mL) and then diluted with dry $CH_2Cl_2$ (2 mL). Benzylidene-2,2-bis(oxymethyl)propionic anhydride (0.50 g, 1.17 mmol) in CH$_2$Cl$_2$ (2 mL) was added dropwise into the reaction mixture and stirred at room temperature overnight. After completion by monitoring from MALDI-TOF, the excess of anhydride was quenched by adding pyridine:water (1:1). The mixture was extracted with CH$_2$Cl$_2$, washed with NaHSO$_4$ (1M), NaHCO$_3$ (10%), and brine. The combined organic phase was dried over MgSO$_4$, and concentrated to give (3,5)12G1-PE-BMPA-G3-(benzylidene)$_8$ (7b) as a white solid: 0.23 g, (61%).

(3,4,5)12G1-PE-BMPA-G3-(benzylidene)$_8$ (7c): (3,4,5) 12G1-PE-BMPA-G2-(OH)$_8$ (6c) (0.50 g, 0.23 mmol) and 4-(dimethylamino) pyridine (DMAP) (10 mg, 0.82 mmol) were dissolved in dry pyridine (2 mL) and then diluted with dry CH$_2$Cl$_2$ (2 mL). Benzylidene-2,2-bis(oxymethyl)propionic anhydride (1.03 g, 2.4 mmol) in CH$_2$Cl$_2$ (4 mL) was added dropwise into the reaction mixture and stirred at room temperature overnight under N$_2$. After completion by monitoring from MALDI-TOF, the excess anhydride was quenched by adding pyridine:water (1:1). The mixture was extracted with CH$_2$Cl$_2$, washed with NaHSO$_4$ (1M), NaHCO$_3$ (10%), and brine. The combined organic phase was dried over MgSO$_4$, concentrated, and purified by column chromatography (silica gel, EtOAc:Hexane=40:60) to give (3,4,5)12G1-PEBMPA-G3-(benzylidene)$_8$ (7c) as a white solid: 0.60 g, (68%).

(3,4)12G1-PE-BMPA-G3-(OH)$_{16}$ (8a): (3,4)12G1-PE-BMPA-G3-(benzylidene)$_8$ (7a) (0.30 g, 0.088 mmol) was dissolved in CH$_2$Cl$_2$ (20 mL) and diluted with MeOH (20 mL). 10% Pd/C (30 mg) was added into the solution and then the reaction flask was evacuated and filled three times with H$_2$. After stirring at room temperature overnight in H$_2$ atmosphere, the Pd/C was filtered off using celite pad and washed with THF. The solvent was evaporated off to give (3,4)12G1-PE-BMPA-G3-(OH)$_{16}$ (8a) as a white solid: 0.15 g (63%).

(3,5)12G1-PE-BMPA-G3-(OH)$_{16}$ (8b): (3,5)12G1-PE-BMPA-G3-(benzylidene)$_8$ (7b) (0.23 g, 0.067 mmol) was dissolved in CH$_2$Cl$_2$ (20 mL) and diluted with MeOH (10 mL). 10% Pd/C (100 mg) was added into the solution and then the reaction flask was evacuated and filled three times with H$_2$. After stirring at room temperature overnight in H$_2$ atmosphere, the Pd/C was filtered off using celite pad and washed with THF. The solvent was evaporated off to give (3,5)12G1-PE-BMPA-G3-(OH)$_{16}$ (8b) as a white solid: 0.15 g (88%).

(3,4,5)12G1-PE-BMPA-G3-(OH)$_{16}$ (8c): (3,4,5)12G1-PE-BMPA-G3-(benzylidene)$_8$ (7c) (0.30 g, 0.079 mmol) was dissolved in CH$_2$Cl$_2$ (20 mL) and diluted with MeOH (10 mL). 10% Pd/C (100 mg) was added into the solution and then the reaction flask was evacuated and filled three times with H$_2$. After stirring at room temperature overnight in H$_2$ atmosphere, the Pd/C was filtered off using celite pad and washed with THF. The solvent was evaporated off to give (3,4,5)12G1-PE-BMPA-G3-(OH)$_{16}$ (8c) as a white solid: 0.16 g (67%).

(3,4)-3EO-G1-(OCH$_3$)$_2$—CO$_2$CH$_3$ (13a): 3,4-Dihydroxymethylbenzoate (5.25 g, 31.22 mmol) was dissolved in DMF (250 mL) that was previously degassed by bubbling nitrogen for 0.5 h. TsTEGMe (11c) (21.87 g, 68.7 mmol), KI (1 g, 15.6 mmol), and K$_2$CO$_3$ (30 g, 217 mmol) were added, and the suspension was stirred overnight at 70° C. The reaction mixture was then cooled to rt, diluted with H$_2$O (300 mL) and extracted with DCM (5×75 mL). The DCM solution was washed with brine (100 mL), dried over MgSO$_4$ then filtered. The solvent was removed under vacuum at low and then high vacuum to remove DCM and DMF respectively. The crude product was purified by silica gel flash column chromatography using a gradient elution of DCM to methanol up 10%. The sample was dried under high vacuum overnight to afford a slightly yellow oil: 11.40 (82% yield).

(3,5)-3EO-G1-(OCH$_3$)$_2$—CO$_2$CH$_3$ (13b): 3,5-Dihydroxymethylbenzoate (1 g, 5.9 mmol) was dissolved in DMF (50 mL) that was previously degassed by bubbling nitrogen for 0.5 h. TsTEGMe (11c) (5.64 g, 17.7 mmol), KI (0.78 g, 4.7 mmol), and K$_2$CO$_3$ (8.15 g, 59 mmol) were added, and the suspension was stirred overnight at 70° C. The reaction mixture was reduced to a slurry under vacuum then diluted with DCM (150 mL). The DCM solution was washed with sat. NaHCO$_3$ (100 mL) and brine (100 mL), dried over MgSO$_4$ then filtered. The solvent was removed under vacuum to remove DCM and DMF respectively. The crude product was purified by silica gel flash column chromatography using a gradient elution of DCM to methanol up 10%. The sample was dried under high vacuum overnight to afford a slightly yellow oil: 2.44 g (93% yield).

(3,4,5)-3EO-G1-(OCH$_3$)$_3$—CO$_2$CH$_3$ (13c): 3,4,5-Trihydroxymethylbenzoate (2.96 g, 16.06 mmol) was dissolved in DMF (160 mL) that was previously degassed by bubbling nitrogen for 0.5 h. TsTEGMe (11c) (18 g, 52.99 mmol), KI (1.33 g, 8.03 mmol), and K$_2$CO$_3$ (22.2 g, 160.6 mmol) were added, and the suspension was stirred for 4 h at 70° C. The reaction mixture was then cooled to rt, diluted with H$_2$O (300 mL) and extracted with DCM (5×100 mL). The DCM solution was washed with brine (100 mL), dried over MgSO$_4$ then filtered. The solvent was removed under vacuum to remove DCM and DMF respectively. The crude product was purified by silica gel flash column chromatography using a gradient elution of DCM to methanol up 10%. The sample was dried under high vacuum overnight to afford a slightly yellow oil: 7.90 g (79% yield).

(3,4)-3EO-G1-(OCH$_3$)$_2$—CO$_2$H (14a): (3,4)-3EO-G1-(OCH$_3$)$_2$—CO$_2$CH$_3$ (13a) (6 g, 13.44 mmol) was dissolved in 95% EtOH (125 mL). KOH (3.77 g, 67.2 mmol) in water (38 mL) was added and the reaction mixture was stirred at reflux for 2 h. The reaction mixture was then cooled to rt, acidified with 6 N HCl (pH 1.5) then poured into water (250 mL) and extracted with DCM (3×100 mL). The DCM solution was washed with brine (100 mL), dried over MgSO$_4$ then filtered. The solvent was removed under vacuum. The crude product was purified by silica gel flash column chromatography using a gradient elution of DCM to methanol up 10%. The sample was dried under high vacuum overnight to afford a waxy white solid: 3.51 g (60% yield).

(3,5)-3EO-G1-(OCH$_3$)$_2$—CO$_2$H (14b): (3,5)-3EO-G1-(OCH$_3$)$_2$—CO$_2$CH$_3$ (13b) (1 g, 2.17 mmol) was dissolved in 95% EtOH (20 mL). KOH (0.61 g, 10.9 mmol) in water (6 mL) was added and the reaction mixture was stirred at reflux for 2 h. The reaction mixture was then cooled to rt, acidified with 6 N HCl (pH 1.5) then poured into water (100 mL) and extracted with DCM (3×33 mL). The DCM solution was washed with brine (50 mL), dried over MgSO$_4$ then filtered. The solvent was removed under vacuum. The crude product was purified by silica gel flash column chromatography using a gradient elution of DCM to methanol up 10%. The sample was dried under high vacuum overnight to afford a slightly yellow oil: 0.75 g (77% yield).

(3,4,5)-3EO-G1-(OCH$_3$)$_3$—CO$_2$H (14c): (3,4,5)-3EO-G1-(OCH$_3$)$_3$—CO$_2$CH$_3$ (13c) (5.00 g, 8.03 mmol) was dissolved in water (20 ml). KOH (2.25 g, 40.15 mmol) in water (10 ml) was added and the reaction mixture was stirred at reflux for 2 h. The reaction mixture was then cooled to room temperature, poured into water, and acidified to pH=1 with 6M HCl. The solution was extracted with EtOAc, washed with water, brine, and dried over MgSO$_4$. The solvent was evaporated and the crude oil was purified by column chromatography to give (3,4,5)-3EO-G1-(OCH$_3$)$_3$—CO$_2$H (14c) as a viscous liquid: 1.15 g (97%).

(3,4)12G1-PE-(benzylidene) (16a): The monobenzacetal of pentaerythritol (4.16 g, 18.5 mmol), (3,4)12G1-CO$_2$H (1a) (20.00 g, 40.75 mmol), and DPTS (5.45 g, 18.5 mmol) were dissolved in anhydrous CH$_2$Cl$_2$ (100 mL). DCC (9.94 g, 48.2 mmol) dissolved in anhydrous CH$_2$Cl$_2$ (10 mL) was added, and the reaction mixture was stirred for 12 h at room temperature. After the reaction was complete, the mixture was diluted, filtered, and rinsed with Et$_2$O. The solvent was removed under vacuum. The residue was purified by column chromatography (silica gel; Et$_2$O/hexane=10:90) and precipitated in MeOH to give (3,4)12G1-PE-(benzylidene) (16a) as a white solid: 21.18 g (98%).

(3,5)12G1-PE-(benzylidene) (16b): The monobenzacetal of pentaerythritol (5.00 g, 22.3 mmol), (3,5)12G1-CO$_2$H (1b) (24.07 g, 49.05 mmol), and DPTS (5.90 g, 22.3 mmol) were dissolved in anhydrous CH$_2$Cl$_2$ (120 mL). DCC (11.96 g, 57.97 mmol) dissolved in anhydrous CH$_2$Cl$_2$ (20 mL) was added, and the reaction mixture was stirred for 12 h at room temperature. After the reaction was complete by TLC, the mixture was diluted, filtered, and rinsed with Et$_2$O. The solvent was removed under vacuum. The residue was purified by column chromatography (silica gel; Et$_2$O/hexane=5:95) and precipitated in MeOH to give (3,5)12G1-PE-(benzylidene) (16b) as a white solid: 25.29 g (97%).

(3,4,5)12G1-PE-(benzylidene) (16c): The monobenzacetal of pentaerythritol (3.64 g, 16.3 mmol), (3,4,5)12G1-CO$_2$H (1c) (24.14 g, 35.75 mmol), and DPTS (4.78 g, 16.3 mmol) were dissolved in anhydrous CH$_2$Cl$_2$ (60 mL). DCC (8.72 g, 42.3 mmol) dissolved in anhydrous CH$_2$Cl$_2$ (10 mL) was added, and the reaction mixture was stirred for 12 h at room temperature. After the reaction was complete by TLC, the mixture was diluted, filtered, and rinsed with Et$_2$O. The solvent was removed under vacuum and the residue was purified by column chromatography (silica gel; Et$_2$O/hexane=10:90) and precipitated in MeOH to give (3,4,5)12G1-PE-(benzylidene) (16c) as a white solid: 23.35 g (93%).

(3,4)12G1-PE-(OH)$_2$ (17a): (3,4)12G1-PE-(benzylidene) (16a) (20.00 g, 17.10 mmol) was dissolved in 1:2 MeOH:CH$_2$Cl$_2$ (150 mL), Pd/C (0.60 g) was added and the flask was evacuated and filled with hydrogen three times. The reaction mixture was then stirred overnight under a hydrogen atmosphere. The reaction mixture was filtered through celite and the filtrate was concentrated, and precipitated in MeOH to give (3,4)12G1-PE-(OH)$_2$ (17a) as a white solid: 18.34 g (99%).

(3,5)12G1-PE-(OH)$_2$ (17b): (3,5)12G1-PE-(benzylidene) (16b) (24.00 g, 20.52 mmol) was dissolved in 1:2 MeOH:CH$_2$Cl$_2$ (150 mL), Pd/C (0.72 g) was added and the flask was evacuated and filled with hydrogen three times. The reaction mixture was then stirred overnight under a hydrogen atmosphere. The reaction mixture was filtered through celite and the solvent was evaporated to give (3,5)12G1-PE-(OH)$_2$ (17b) as a white solid: 22.19 g (100%).

(3,4,5)12G1-PE-(OH)$_2$ (17c): (3,4,5)12G1-PE-(benzylidene) (16c) (22.48 g, 14.61 mmol) was dissolved in 1:2 MeOH:CH$_2$Cl$_2$ (150 mL), Pd/C (0.65 g) was added and the flask was evacuated and filled with hydrogen three times. The reaction mixture was then stirred overnight under a hydrogen atmosphere. The reaction mixture was filtered through celite and the filtrate was concentrated, and precipitated in MeOH to give (3,4,5)12G1-PE-(OH)$_2$ (17c) as a white solid: 20.94 g (99%).

(3,4)12G1-PE-(3,4)-3EO-G1-(OCH$_3$)$_4$ (18a): (3,4)12G1-PE-(OH)$_2$ (17a) (1.11 g, 1.03 mmol), (3,4)-3EO-G1-(OCH$_3$)$_2$—CO$_2$H (14a) (1.01 g, 2.27 mmol) and DPTS (0.303 g, 1.03 mmol) were dissolved in anhydrous DCM (7 mL). DCC (0.553 g, 2.68 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was removed under vacuum and the residue was purified by silica gel flash column chromatography using a gradient elution of ethyl acetate to methanol up 10% to afford a colorless oil: 1.00 g (50% yield).

(3,4)12G1-PE-(3,5)-3EO-G1-(OCH$_3$)$_4$ (18b): (3,4)12G1-PE-(OH)$_2$ (17a) (1.11 g, 1.03 mmol), (3,5)-3EO-G1-(OCH$_3$)$_2$—CO$_2$H (14b) (1.01 g, 2.27 mmol) and DPTS (2.68 g, 1.03 mmol) were dissolved in anhydrous DCM (7 mL). DCC (0.553 g, 2.68 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was removed under vacuum and the residue was purified by silica gel flash column chromatography using a gradient elution of ethyl acetate to methanol up 10% to afford a colorless oil: 0.72 g (36% yield).

(3,4)12G1-PE-(3,4,5)-3EO-G1-(OCH$_3$)$_6$ (18c): (3,4)12G1-PE-(OH)$_2$ (17a) (0.952 g, 0.88 mmol), (3,4,5)-3EO-G1-(OCH$_3$)$_3$—CO$_2$H (14c) (1.18 g, 1.94 mmol) and DPTS (0.259 g, 0.88 mmol) were dissolved in anhydrous DCM (7 mL). DCC (0.472 g, 2.288 mmol) dissolved in anhydrous DCM (3 mL) was added, and the reaction mixture was stirred for 24 h at rt. After the reaction was complete, the mixture the mixture was diluted with hexanes, filtered through celite and rinsed with hexanes. The solvent was removed under vacuum and the residue was purified by silica gel flash column chromatography using a gradient elution of ethyl acetate to methanol up 10% to afford a colorless oil: 1.00 g (50% yield).

(3,5)12G1-PE-(3,4)-3EO-G1-(OCH$_3$)$_4$ (18d): (3,5)12G1-PE-(OH)$_2$ (17b) (0.80 g, 0.74 mmol), (3,4)-3EO-G1-(OCH$_3$)$_2$—CO$_2$H (14a) (0.72 g, 1.62 mmol), and DPTS (0.22 g, 0.75 mmol) were dissolved in anhydrous CH$_2$Cl$_2$ (7 mL). DCC (0.40 g, 1.91 mmol) dissolved in anhydrous CH$_2$Cl$_2$ (3 mL) was added, and the reaction mixture was stirred for 12 h at room temperature. After the reaction was complete, the mixture was diluted, filtered, and rinsed with Et$_2$O. The solvent was removed under vacuum. The residue was purified by column chromatography (silica gel; MeOH/EtOAc=5:95) to give (3,5)12G1-PE-(3,4)-3EO-G1-(OCH$_3$)$_4$ (18d) as a colorless liquid: 1.03 g (72%).

(3,5)12G1-PE-(3,5)-3EO-G1-(OCH$_3$)$_4$ (18e): (3,5)12G1-PE-(OH)$_2$ (17b) (0.95 g, 0.88 mmol), (3,5)-3EO-G1-(OCH$_3$)$_2$—CO$_2$H (14b) (0.88 g, 1.97 mmol) and DPTS (0.265 g, 0.9 mmol) were dissolved in anhydrous DCM (7 mL). DCC (0.483 g, 2.34 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was removed under vacuum. The residue was purified using column chromatography on silica gel with a mobile phase of ethyl acetate to afford a colorless oil: 0.4 g (23% yield).

(3,5)12G1-PE-(3,4,5)-3EO-G1-(OCH$_3$)$_6$ (18f): (3,5)12G1-PE-(OH)$_2$ (17b) (0.70 g, 0.65 mmol), (3,4,5)-3EO-G1-(OCH$_3$)$_3$—CO$_2$H (14c) (0.86 g, 1.42 mmol), and DPTS (0.19 g, 0.65 mmol) were dissolved in anhydrous CH$_2$Cl$_2$ (7 mL). DCC (0.35 g, 1.68 mmol) dissolved in anhydrous CH$_2$Cl$_2$ (3 mL) was added, and the reaction mixture was stirred for 12 h at room temperature. After the reaction was complete, the mixture was diluted, filtered, and rinsed with Et$_2$O. The solvent was removed under vacuum and the residue was purified by column chromatography (silica gel; MeOH/EtOAc=10:90) to give (3,5)12G1-PE-(3,4,5)-3EO-G1-(OCH$_3$)$_6$ (18f) as a colorless liquid: 1.16 g (79%).

(3,4,5)12G1-PE-(3,4)-3EO-G1-(OCH$_3$)$_4$ (18g): (3,4,5) 12G1-PE-(OH)$_2$ (17c) (1.02 g, 0.70 mmol), (3,4)-3EO-G1-(OCH$_3$)$_2$—CO$_2$H (14a) (0.69 g, 1.55 mmol), and DPTS (0.21 g, 0.70 mmol) were dissolved in anhydrous CH$_2$Cl$_2$ (7 mL). DCC (0.38 g, 1.83 mmol) dissolved in anhydrous CH$_2$Cl$_2$ (3 mL) was added, and the reaction mixture was stirred for 12 h at room temperature. After the reaction was complete, the mixture was diluted, filtered, and rinsed with Et$_2$O. The solvent was removed under vacuum and the residue was purified by column chromatography (silica gel; MeOH/CH$_2$Cl$_2$=2:98) to give (3,4,5)12G1-PE-(3,4)-3EO-G1-(OCH$_3$)$_4$ (18g) as a white solid: 0.96 g (59%).

(3,4,5)12G1-PE-(3,5)-3EO-G1-(OCH$_3$)$_4$ (18h): (3,4,5) 12G1-PE-(OH)$_2$ (17c) (1.11 g, 0.76 mmol), (3,5)-3EO-G1-(OCH$_3$)$_2$—CO$_2$H (14b) (0.75 g, 1.68 mmol), and DPTS (0.22 g, 0.76 mmol) were dissolved in anhydrous CH$_2$Cl$_2$ (7 mL). DCC (0.41 g, 1.99 mmol) dissolved in anhydrous CH$_2$Cl$_2$ (3 mL) was added, and the reaction mixture was stirred for 12 h at room temperature. After the reaction was complete, the mixture was diluted, filtered, and rinsed with Et2O. The solvent was removed under vacuum and the residue was purified by column chromatography (silica gel; EtOAc) to give (3,4,5)12G1-PE-(3,5)-3EO-G1-(OCH$_3$)$_4$ (18h) as a white solid: 0.76 g (43%).

(3,4,5)12G1-PE-(3,4,5)-3EO-G1-(OCH$_3$)$_6$ (18i): (3,4,5) 12G1-PE-(OH)$_2$ (17c) (1.11 g, 0.76 mmol), (3,4,5)-3EO-G1-(OCH$_3$)$_3$—CO$_2$H (14c) (1.02 g, 1.68 mmol), and DPTS (0.23 g, 0.762 mmol) were dissolved in anhydrous CH$_2$Cl$_2$ (7 mL). DCC (0.41 g, 1.98 mmol) dissolved in anhydrous CH$_2$Cl$_2$ (3 mL) was added, and the reaction mixture was stirred for 12 h at room temperature. After the reaction was complete, the mixture was diluted, filtered, and rinsed with Et$_2$O. The solvent was removed under vacuum and the residue was purified by column chromatography (silica gel; MeOH/EtOAc=5:95) and recrystallized in MeOH to give (3,4,5)12G1-PE-(3,4,5)-3EO-G1-(OCH$_3$)$_6$ (18i) as a white solid: 1.77 g (82%).

(3,4)-2EO-G1-(OCH$_3$)$_2$—CO$_2$CH$_3$ (19a): 3,4-dihydroxymethyl benzoate (3.50 g, 20.8 mmol) was dissolved in DMF (90 mL) that was degassed by bubbling nitrogen for 0.5 h. Diethylene glycol monomethyl ether tosylate (12.00 g, 43.7 mmol) in DMF (10 mL), and K$_2$CO$_3$ (11.52 g, 83.3 mmol) were added, and the suspension was stirred overnight at 70° C. The reaction mixture was then cooled to room temperature and poured into water. The mixture was extracted with EtOAc, washed with water and brine, and dried over MgSO$_4$. The solvent was removed under vacuum and the residue was purified by column chromatography (silica gel, EtOAc) to give (3,4)-2EO-G1-CO$_2$CH$_3$ (19a) as a colorless liquid: 6.24 g (80%).

(3,5)-2EO-G1-(OCH$_3$)$_2$—CO$_2$CH$_3$ (19b): 3,5-dihydroxymethyl benzoate (3.50 g, 20.8 mmol) was dissolved in DMF (60 mL) that was degassed previously by bubbling nitrogen for 0.5 h. Diethylene glycol monomethyl ether tosylate (12.00 g, 43.7 mmol) in DMF (15 mL), and K$_2$CO$_3$ (11.52 g, 83.3 mmol) were added, and the suspension was stirred overnight at 70° C. The reaction mixture was then cooled to room temperature and poured into water. The mixture was extracted with EtOAc, washed with water and brine, and dried over MgSO$_4$. The solvent was removed under vacuum and the residue was purified by column chromatography (silica gel, EtOAc/hexane=50:50) to give (3,5)-2EO-G1-CO$_2$CH$_3$ (19b) as a colorless liquid: 6.43 g (83%).

(3,4,5)-2EO-G1-(OCH$_3$)$_3$—CO$_2$CH$_3$ (19c): 3,4,5-trihydroxymethyl benzoate (2.63 g, 14.3 mmol) was dissolved in DMF (35 mL) was previously degassed by bubbling nitrogen for 0.5 h. Diethylene glycol monomethylether tosylate (15.66 g, 57.1 mmol) in DMF (5 mL), and K$_2$CO$_3$ (11.89 g, 85.6 mmol) were added, and the suspension was stirred overnight at 70° C. The reaction mixture was then cooled to room temperature and poured into water. The mixture was extracted with EtOAc, washed with water and brine, and dried over MgSO$_4$. The solvent was removed under vacuum and the residue was purified by column chromatography (silica gel, EtOAc/hexane=50:50) to give (3,4,5)-2EO-G1-CO$_2$CH$_3$ (19c) as a colorless liquid: 6.27 g (90%).

(3,4,5)-1EO-G1-(OCH$_3$)$_3$—CO$_2$CH$_3$ (20): 3,4,5-trihydroxymethyl benzoate (1.28 g, 6.94 mmol) was dissolved in DMF (25 mL) that was previously degassed by bubbling nitrogen for 0.5 h. Ethylene glycol methylether tosylate (6.00 g, 26.1 mmol) in DMF (5 mL), and K$_2$CO$_3$ (9.59 g, 69.4 mmol) were added, and the suspension was stirred overnight at 70° C. The reaction mixture was then cooled to room temperature and poured into water. The mixture was extracted with EtOAc, washed with water and brine, and dried over MgSO$_4$. The solvent was removed under vacuum and the residue was purified by column chromatography (silica gel, EtOAc/hexane=50:50) to give (3,4,5)-1EO-G1-CO$_2$CH$_3$ (20) as a colorless liquid: 1.99 g (80%).

(3,4)-2EO-G1-(OCH$_3$)$_2$—CO$_2$H (21a): (3,4)-2EO-G1-CO$_2$CH$_3$ (19a) (5.20 g, 14.0 mmol) was dissolved in water (40 ml). KOH (4.70 g, 83.8 mmol) in water (10 ml) was added and the reaction mixture was stirred at reflux for 2 h. The reaction mixture was then cooled to room temperature, and acidified to pH=1 with 6M HCl. The solution was extracted with EtOAc, washed with water, brine, and dried over MgSO$_4$. The solvent was evaporated to give (3,4)-2EO-G$_1$-CO$_2$H (21a) as a white solid: 5.00 g (100%).

(3,5)-2EO-G1-(OCH$_3$)$_2$—CO$_2$H (21b): (3,5)-2EO-G1-CO$_2$CH$_3$ (19b) (4.16 g, 11.2 mmol) was dissolved in water (40 ml). KOH (3.76 g, 67.0 mmol) in water (10 ml) was added and the reaction mixture was stirred at reflux for 2 h. The reaction mixture was then cooled to room temperature, and acidified to pH=1 with 6M HCl. The solution was extracted with EtOAc, washed with water, brine, and dried over MgSO$_4$. The solvent was evaporated to give (3,5)$_2$E-CO$_2$H (21b) as a colorless liquid: 3.99 g (100%).

(3,4,5)-2EO-G1-(OCH$_3$)$_3$—CO$_2$H (21c): (3,4,5)-2EO-G1-CO$_2$CH$_3$ (19c) (1.57 g, 3.20 mmol) was dissolved in water (30 ml). KOH (1.10 g, 19.2 mmol) in water (10 ml) was added and the reaction mixture was stirred at reflux for 2 h. The reaction mixture was then cooled to room temperature, and acidified to pH=1 with 6M HCl. The solution was extracted with EtOAc, washed with water, brine, and dried over MgSO$_4$. The solvent was evaporated to give (3,4,5)$_2$EO-CO$_2$H (21c) as a colorless liquid: 1.45 g (95%).

(3,4,5)-1EO-G1-(OCH$_3$)$_3$—CO$_2$H (22): (3,4,5)-1EO-G1-CO$_2$CH$_3$ (20) (1.90 g, 5.30 mmol) was dissolved in water (20 ml) and 95% EtOH (10 mL). KOH (1.69 g, 30.0 mmol) in water (10 ml) was added and the reaction mixture was stirred at reflux for 2 h. The reaction mixture was then cooled to room temperature, and acidified to pH=1 with 6M HCl. The solution was extracted with EtOAc, washed with water, brine, and dried over $MgSO_4$. The solvent was evaporated to give (3,4,5)1EO-$CO_2$H (22) as a white solid: 1.80 g (98%).

(3,4)12G1-PE-(3,4)-2EO-G1-$(OCH_3)_4$ (23a): (3,4)12G1-PE-$(OH)_2$ (17a) (0.76 g, 0.70 mmol), (3,4)-2EO-G1-$(OCH_3)_2$—$CO_2$H (21a) (0.55 g, 1.55 mmol), and DPTS (0.21 g, 0.70 mmol) were dissolved in anhydrous $CH_2Cl_2$ (5 mL). DCC (0.38 g, 1.83 mmol) dissolved in anhydrous $CH_2Cl_2$ (2 mL) was added, and the reaction mixture was stirred for 12 h at room temperature. After the reaction was complete, the mixture was diluted with $Et_2O$, filtered, and rinsed with $Et_2O$. The solvent was removed under vacuum and the residue was purified by column chromatography (silica gel; EtOAc) and precipitated in MeOH to give (3,4)12G1-PE-(3,4)-2EO-G1-$(OCH_3)_4$ (23a) as a white solid: 1.16 g (94%).

(3,4)12G1-PE-(3,5)-2EO-G1-$(OCH_3)_4$ (23b): (3,4)12G1-PE-$(OH)_2$ (17a) (0.76 g, 0.70 mmol), (3,5)-2EO-G1-$(OCH_3)_2$—$CO_2$H (21b) (0.55 g, 1.55 mmol), and DPTS (0.21 g, 0.70 mmol) were dissolved in anhydrous $CH_2Cl_2$ (5 mL) DCC (0.38 g, 1.83 mmol) dissolved in anhydrous $CH_2Cl_2$ (2 mL) was added, and the reaction mixture was stirred for 12 h at room temperature. After the reaction was complete, the mixture was diluted with $Et_2O$, filtered, and rinsed with $Et_2O$. The solvent was removed under vacuum and the residue was purified by column chromatography (silica gel; EtOAc/hexane=70:30) to give (3,4)12G1-PE-(3,5)-2EO-G1-$(OCH_3)_4$ (23b) as a white solid: 1.04 g (84%).

(3,4)12G1-PE-(3,4,5)-2EO-G1-$(OCH_3)_6$ (23c): (3,4)12G1-PE-$(OH)_2$ (17a) (0.47 g, 0.43 mmol), (3,4,5)-2EO-G1-$(OCH_3)_3$—$CO_2$H (21c) (0.45 g, 0.94 mmol), and DPTS (0.13 g, 0.43 mmol) were dissolved in anhydrous $CH_2Cl_2$ (5 mL). DCC (0.23 g, 1.12 mmol) dissolved in anhydrous $CH_2Cl_2$ (2 mL) was added, and the reaction mixture was stirred for 12 h at room temperature. After the reaction was complete, the mixture was diluted with $Et_2O$, filtered, and rinsed with $Et_2O$. The solvent was removed under vacuum and the residue was purified by column chromatography (silica gel; MeOH/EtOAc=2:98) and precipitate in MeOH to give (3,4)12G1-PE-(3,4,5)-2EO-G1-$(OCH_3)_6$ (23c) as a white solid: 0.60 g (70%).

(3,5)12G1-PE-(3,4)-2EO-G1-$(OCH_3)_4$ (23d): (3,5)12G1-PE-$(OH)_2$ (17b) (0.76 g, 0.70 mmol), (3,4)-2EO-G1-$(OCH_3)_2$—$CO_2$H (21a) (0.55 g, 1.55 mmol), and DPTS (0.21 g, 0.70 mmol) were dissolved in anhydrous $CH_2Cl_2$ (5 mL). DCC (0.38 g, 1.83 mmol) dissolved in anhydrous $CH_2Cl_2$ (2 mL) was added, and the reaction mixture was stirred for 12 h at room temperature. After the reaction was complete, the mixture was diluted with $Et_2O$, filtered, and rinsed with $Et_2O$. The solvent was removed under vacuum and the residue was purified by column chromatography (silica gel; EtOAc/hexane=80:20) to give (3,5)12G1-PE-(3,4)-2EO-G1-$(OCH_3)_4$ (23d) as a colorless liquid: 1.10 g (89%).

(3,5)12G1-PE-(3,5)-2EO-G1-$(OCH_3)_4$ (23e): (3,5)12G1-PE-$(OH)_2$ (17b) (0.76 g, 0.70 mmol), (3,5)-2EO-G1-$(OCH_3)_2$—$CO_2$H (21b) (0.55 g, 1.55 mmol), and DPTS (0.21 g, 0.70 mmol) were dissolved in anhydrous $CH_2Cl_2$ (5 mL). DCC (0.38 g, 1.83 mmol) dissolved in anhydrous $CH_2Cl_2$ (2 mL) was added, and the reaction mixture was stirred for 12 h at room temperature. After the reaction was complete, the mixture was diluted with $Et_2O$, filtered, and rinsed with $Et_2O$. The solvent was removed under vacuum and the residue was purified by column chromatography (silica gel; EtOAc/hexane=60:40) to give (3,5)12G1-PE-(3,5)-2EO-G1-$(OCH_3)_4$ (23e) as a colorless liquid: 0.69 g (56%).

(3,5)12G1-PE-(3,4,5)-2EO-G1-$(OCH_3)_6$ (230: (3,5) 12G1-PE-$(OH)_2$ (17b) (0.47 g, 0.43 mmol), (3,4,5)-2EO-G1-$(OCH_3)_3$—$CO_2$H (21c) (0.45 g, 0.94 mmol), and DPTS (0.13 g, 0.43 mmol) were dissolved in anhydrous $CH_2Cl_2$ (5 mL). DCC (0.23 g, 1.12 mmol) dissolved in anhydrous $CH_2Cl_2$ (3 mL) was added, and the reaction mixture was stirred for 12 h at room temperature. After the reaction was complete, the mixture was diluted with $Et_2O$, filtered, and rinsed with $Et_2O$. The solvent was removed under vacuum and the residue was purified by column chromatography (silica gel; EtOAc) to give (3,5)12G1-PE-(3,4,5)-2EO-G1-$(OCH_3)_6$ (230 as a colorless liquid: 0.58 g (67%).

(3,4,5)12G1-PE-(3,4)-2EO-G1-$(OCH_3)_4$ (23g): (3,4,5)12G1-PE-$(OH)_2$ (17c) (0.82 g, 0.57 mmol), (3,4)-2EO-G1-$(OCH_3)_2$—$CO_2$H (21a) (0.45 g, 1.25 mmol), and DPTS (0.17 g, 0.67 mmol) were dissolved in anhydrous $CH_2Cl_2$ (5 mL). DCC (0.30 g, 1.47 mmol) dissolved in anhydrous $CH_2Cl_2$ (2 mL) was added, and the reaction mixture was stirred for 12 h at room temperature. After the reaction was complete, the mixture was diluted with $Et_2O$, filtered, and rinsed with $Et_2O$. The solvent was evaporated under vacuum and the residue was purified by column chromatography (silica gel; EtOAc) to give (3,4,5)12G1-PE-(3,4)-2EO-G1-$(OCH_3)_4$ (23g) as a colorless liquid: 1.09 g (91%).

(3,4,5)12G1-PE-(3,5)-2EO-G1-$(OCH_3)_4$ (23h): (3,4,5) 12G1-PE-$(OH)_2$ (17c) (0.82 g, 0.57 mmol), (3,5)-2EO-G1-$(OCH_3)_2$—$CO_2$H (21b) (0.45 g, 1.24 mmol), and DPTS (0.17 g, 0.57 mmol) were dissolved in anhydrous $CH_2Cl_2$ (5 mL). DCC (0.38 g, 1.83 mmol) dissolved in anhydrous $CH_2Cl_2$ (2 mL) was added, and the reaction mixture was stirred for 12 h at room temperature. After the reaction was complete, the mixture was diluted with $Et_2O$, filtered, and rinsed with $Et_2O$. The solvent was evaporated under vacuum and the residue was purified by column chromatography (silica gel; EtOAc/hexane=60:40) to give (3,4,5)12G1-PE-(3,5)-2EO-G1-$(OCH_3)_4$ (23h) as a white solid: 0.91 g (76%).

(3,4,5)12G1-PE-(3,4,5)-2EO-G1-$(OCH_3)_6$ (23i): (3,4,5) 12G1-PE-$(OH)_2$ (17c) (0.62 g, 0.43 mmol), (3,4,5)-2EO-G1-$(OCH_3)_3$—$CO_2$H (21c) (0.45 g, 0.94 mmol), and DPTS (0.13 g, 0.43 mmol) were dissolved in anhydrous $CH_2Cl_2$ (5 mL). DCC (0.23 g, 1.12 mmol) dissolved in anhydrous $CH_2Cl_2$ (3 mL) was added, and the reaction mixture was stirred for 12 h at room temperature. After the reaction was complete, the mixture was diluted with $Et_2O$, filtered, and rinsed with $Et_2O$. The solvent was evaporated under vacuum and the residue was purified by column chromatography (silica gel; EtOAc) to give (3,4,5)12G1-PE-(3,4,5)-2EO-G1-$(OCH_3)_6$ (23i) as a white solid: 0.87 g (81%).

(3,4,5)12G1-PE-(3,4,5)-1EO-G1-$(OCH_3)_6$ (24): (3,4,5) 12G1-PE-$(OH)_2$ (17c) (0.96 g, 0.66 mmol), (3,4,5)-1EO-G1-$(OCH_3)_3$—$CO_2$H (22) (0.50 g, 1.45 mmol), and DPTS (0.19 g, 0.66 mmol) were dissolved in anhydrous $CH_2Cl_2$ (5 mL). DCC (0.36 g, 1.72 mmol) dissolved in anhydrous $CH_2Cl_2$ (3 mL) was added, and the reaction mixture was stirred for 12 h at room temperature. After the reaction was complete, the mixture was diluted, filtered, and rinsed with $Et_2O$. The solvent was evaporated under vacuum and the residue was purified by column chromatography (silica gel; EtOAc/hexane=50:50) to give (3,4,5)12G1-PE-(3,4,5)-1EO-G1-$(OCH_3)_6$ (24) as a white solid: 1.20 g (86%).

8-(2H-Tetrahydropyran-2-yloxy)-$3n_6^3$-dioxaoctan-1-ol (25b): Triethylene glycol (25 g, 166 mmol), 3,4-dihydro-2H-pyran (3.53 mL, 41.5 mmol) and p-toluenesulfonic acid (1.43 g, 8.3 mmol) were dissolved in DCM at 0° C. The reaction was then removed from the ice bath and stirred for 2 h at rt. The reaction mixture was then treated with water (100 mL) and the organic layer removed. The aqueous layer was extracted with DCM (2×25) after which the organic layers were combined and washed with water (100 mL) and brine (100 mL), and dried over $MgSO_4$, then filtered. The solvent was removed using a rotary evaporator. The sample was purified using column chromatography (silica gel, EtOAc to MeOH:EtOAc=15:85) to afford a clear colorless oil: 5 g (51% yield).

1-(2H-Tetrahydropyran-2-yloxy)-8-tosyloxy-3n$_6^3$-dioxaoctane (26b): 8-(2H-Tetrahydropyran-2-yloxy)-3n$_6^3$-dioxaoctan-1-ol (25b) (6.07 g, 25.9 mmol), triethylamine (5.4 mL, 38.9 mmol) and dimethylaminopyridine (0.32 g, 2.6 mmol) were dissolved in DCM. 4-toluenesulfonyl chloride (5.43 g, 28.5 mmol) was added and the reaction mixture stirred overnight at room temperature (rt). The reaction mixture was then washed with water (100 mL), 2 M HCl (100 mL), water (100 mL) and brine (100 mL), and dried over MgSO$_4$, then filtered. The solvent was removed using a rotary evaporator. The sample was purified using column chromatography (silica gel, EtOAc) to afford a clear colorless oil: 8.68 g (86% yield).

(3,4,5)-1EO-G1-(OTHP)$_3$—CO$_2$CH$_3$ (27): 3,4,5-trihydroxymethylbenzoate (0.307 g, 1.66 mmol) was dissolved in DMF (17 mL) that was previously degassed by bubbling nitrogen for 0.5 h. Ethylene glycol monotosyl monotetrahydropyran (2 g, 6.66 mmol), KI (0.22 g, 1.33 mmol), and K$_2$CO$_3$ (2.3 g, 16.6 mmol) were added, and the suspension was stirred 3 h at 80° C. The reaction mixture was then cooled to rt and solvent volume reduced by half using high vacuum rotational evaporation. The slurry was diluted with DCM (100 mL) and washed with sat. NaHCO$_3$ (100 mL), water (100 mL), brine (100 mL), and dried over MgSO$_4$ then filtered. Solvent was removed under vacuum at low and then high vacuum to remove DCM and DMF respectively. The sample was purified using column chromatography on silica gel with a mobile phase of 1:2 ethyl acetate:hexanes, and the sample was dried under high vacuum overnight to afford a colorless oil: 0.92 g (97% yield).

(3,4)-3EO-G1-(OTHP)$_2$—CO$_2$CH$_3$ (28a): 3,4-dihydroxymethylbenzoate (0.86 g, 5.15 mmol) was dissolved in DMF (50 mL) that was previously degassed by bubbling nitrogen for 0.5 h. TsTEGMe (5 g, 12.87 mmol), KI (0.68 g, 4.12 mmol), and K$_2$CO$_3$ (7.1 g, 51.5 mmol) were added, and the suspension was stirred 2 h at 70° C. The reaction mixture was then cooled to rt and DMF was removed using high vacuum rotational evaporation. The sample was diluted with DCM (150 mL) and washed with sat. NaHCO$_3$ (100 mL), water (2×100 mL), and dried over MgSO$_4$ then filtered. Solvent was removed under vacuum. The sample was purified using column chromatography on silica gel with a mobile phase of ethyl acetate, and the sample was dried under high vacuum overnight to afford a colorless oil: 2.03 g (66% yield).

(3,4,5)-3EO-G1-(OTHP)$_3$—CO$_2$CH$_3$ (28b): 3,4,5-trihydroxymethylbenzoate (0.113 g, 0.62 mmol) was dissolved in DMF (10 mL) that was previously degassed by bubbling nitrogen for 0.5 h. TsTEGMe (0.79 g, 2.03 mmol), KI (0.08 g, 0.49 mmol), and K$_2$CO$_3$ (0.59 g, 4.3 mmol) were added, and the suspension was stirred overnight at 70° C. The reaction mixture was then cooled to rt and DMF was removed using under high vacuum. The sample was diluted with EtOAc (100 mL) and washed with water (100 mL), sat. NaHCO$_3$ (100 mL), water (100 mL), and dried over MgSO$_4$ then filtered. The solvent was removed under vacuum. The sample was purified using column chromatography on silica gel with a mobile phase of ethyl acetate, and the sample was dried under high vacuum overnight to afford a colorless oil: 0.32 g (62% yield).

(3,4,5)-1EO-G1-(OTHP)$_3$—CO$_2$H (29): (3,4,5)-1EO-G1-(OTHP)$_3$—CO$_2$CH$_3$ (27) (3.55 g, 6.24 mmol) was dissolved in 95% EtOH (70 mL). KOH (1.75 g, 31.2 mmol) in water (17.5 mL) was added and the reaction mixture was stirred at reflux for 10 min. The reaction mixture was then cooled to rt, acidified with 160 mM HCl (200 mL) and extracted with ethyl acetate (3×50 mL). The ethyl acetate solution was washed with water (2×100 mL) and brine (100 mL), and dried over MgSO$_4$ then filtered. The solvent was removed under vacuum, and the sample was dried under high vacuum overnight to afford a slightly green oil: 3.46 g (quant. yield). No further purification was necessary.

(3,4)-3EO-G1-(OTHP)$_2$—CO$_2$H (30a): (3,4)-3EO-G1-(OTHP)$_2$—CO$_2$CH$_3$ (28a) (2 g, 3.33 mmol) was dissolved in 95% EtOH (60 mL). KOH (0.93 g, 16.65 mmol) in water (9 mL) was added and the reaction mixture was stirred at reflux for 10 min. The reaction mixture was then cooled to rt, acidified with acetic acid (1.75 mL, 30.6 mmol) in water (150 mL) and extracted with ethyl acetate (4×200 mL). The ethyl acetate solution was washed with water (50 mL) and dried over MgSO$_4$ then filtered. The solvent was removed under vacuum. In order to azeotropically remove the residual acetic acid, the sample was dissolved in benzene, which was then removed under vacuum. This cycle was repeated twice. The crude product was purified by silica gel flash column chromatography using a gradient elution of DCM to methanol up 10% and the sample was dried under high vacuum overnight to afford a yellow oil: 1.48 g (76% yield).

(3,4,5)-3EO-G1-(OTHP)$_3$—CO$_2$CH$_3$ (30b): (3,4,5)-3EO-G1-(OTHP)$_3$—CO$_2$CH$_3$ (28b) (1.21 g, 1.45 mmol) was dissolved in 95% EtOH (20 mL). KOH (0.5 g, 8.72 mmol) in water (5 mL) was added and the reaction mixture was stirred at reflux for 10 min. The reaction mixture was then cooled to rt, acidified with acetic acid (0.55 mL, 9.57 mmol) in water (100 mL) and extracted with ethyl acetate (3×50 mL). The ethyl acetate solution was washed with brine (50 mL), dried over MgSO$_4$ then filtered. The solvent was removed under vacuum. In order to azeotropically remove the residual acetic acid, the sample was dissolved in benzene, which was then removed under vacuum. This cycle was repeated twice and the sample was dried under high vacuum overnight to afford a yellow oil: 1.09 g (92% yield). No further purification was necessary.

(3,4)12G1-PE-(3,4,5)-1EO-G1-(OTHP)$_3$ (31aTHP): (3,4) 12G1-PE-(OH)$_2$ (17a) (0.44 g, 0.41 mmol), (3,4,5)-1EOG1-(OTHP)$_3$—CO$_2$H (29) (0.55 g, 0.99 mmol) and DPTS (0.121 g, 0.41 mmol) were dissolved in anhydrous DCM (7 mL). DCC (0.221 g, 1.07 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the crude product was purified by silica gel flash column chromatography using a gradient elution of hexane to ethyl acetate up to 100%. The sample was dried under high vacuum overnight to afford a colorless oil: 1.90 g (90% yield).

(3,4)12G1-PE-(3,4,5)-1EO-G1-(OH)$_6$ (31a): (3,4)12G1-PE-(3,4,5)-1EO-G1-(OTHP)$_3$ (31aTHP) (0.45 g, 0.21 mmol) was dissolved in 1:1 DCM:MeOH (10 mL). TsOH (0.05 g, 0.31 mmol) was added and the reaction mixture was stirred for 1 h at rt. After the reaction was complete, the reaction mixture was concentrated under vacuum and then dissolved in DCM (100 mL). The organic layer was washed with sat. NaHCO$_3$ and sat. NaCl, and then dried over MgSO$_4$. The solution was filtered and the solvent was evaporated under reduced pressure. The crude product was purified by silica gel flash column chromatography using a gradient elution of DCM to methanol up to 10%. The solvent was evaporated to afford a white solid: 0.20 g (58% yield).

(3,5)12G1-PE-(3,4,5)-1EO-G1-(OTHP)$_6$ (31bTHP): (3,5)12G1-PE-(OH)$_2$ (17b) (0.54 g, 0.50 mmol), (3,4,5)-1EOG1-(OTHP)$_3$—CO$_2$H (29) (0.66 g, 1.19 mmol) and DPTS (0.147 g, 0.5 mmol) were dissolved in anhydrous DCM (7 mL). DCC (0.266 g, 1.29 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of hexanes to ethyl acetate up to 10% The sample was dried under high vacuum overnight to afford a colorless oil: 1.00 g (93% yield).

(3,5)12G1-PE-(3,4,5)-1EO-G1-(OH)$_6$ (31b): (3,5)12G1-PE-(3,4,5)-1EO-G1-(OTHP)$_6$ (31bTHP) (0.5 g, 0.23 mmol) was dissolved in 1:1 DCM:MeOH (10 mL). TsOH (0.06 g, 0.35 mmol) was added and the reaction mixture was stirred for 1 h at rt. After the reaction was complete, the reaction mixture was concentrated under vacuum and then dissolved in DCM (100 mL). The organic layer was washed with sat. NaHCO$_3$ and sat. NaCl, and then dried over MgSO$_4$. The solution was filtered and the solvent was evaporated under reduced pressure. The crude product was purified by silica gel flash column chromatography using a gradient elution of DCM to methanol up to 10%. The solvent was evaporated to afford a white solid: 0.20 g (53% yield).

(3,4,5)12G1-PE-(3,4,5)-1EO-G1-(OTHP)$_6$ (31cTHP): (3,4,5)12G1-PE-(OH)$_2$ (17c) (0.98 g, 0.68 mmol), (3,4,5)-1EOG1-(OTHP)$_3$—CO$_2$H (29) (0.83 g, 1.5 mmol) and DPTS (0.2 g, 0.68 mmol) were dissolved in anhydrous DCM (7 mL). DCC (0.42 g, 2.04 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of hexanes to ethyl acetate up to 10%. The sample was dried under high vacuum overnight to afford a colorless oil: 0.42 g (24% yield).

(3,4,5)12G1-PE-(3,4,5)-1EO-G1-(OH)$_6$ (31c): (3,4,5)12G1-PE-(3,4,5)-1EO-G1-(OTHP)$_6$ (31cTHP) (0.42 g, 0.166 mmol) was dissolved in 1:1 DCM:MeOH (10 mL). TsOH (0.04 g, 0.25 mmol) was added and the reaction mixture was stirred for 1 h at rt. After the reaction was complete, the reaction mixture was concentrated under vacuum and then dissolved in DCM (100 mL). The organic layer was washed with sat. NaHCO$_3$ and sat. NaCl, and then dried over MgSO$_4$. The solution was filtered and solvent was evaporated under reduced pressure and the residue was purified by silica gel flash column chromatography using a gradient elution of DCM to methanol up to 10%. The solvent was evaporated to afford a white solid: 0.20 g (60% yield).

(3,4)12G1-PE-(3,4)-3EO-G1-(OTHP)$_4$ (32aTHP): (3,4)12G1-PE-(OH)$_2$ (17a) (0.42 g, 0.39 mmol), (3,4)-3EO-G1-(OTHP)$_2$—CO$_2$H (30a) (0.55 g, 0.94 mmol) and DPTS (0.11 g, 0.39 mmol) were dissolved in anhydrous DCM (7 mL). DCC (0.21 g, 1.01 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of EtOAc to methanol up to 5%. The sample was dried under high vacuum overnight to afford a colorless oil: 0.78 g (90% yield).

(3,4)12G1-PE-(3,4)-3EO-G1-(OH)$_4$ (32a): (3,4)12G1-PE-(3,4)-3EO-G1-(OTHP)$_4$ (32aTHP) (0.78 g, 0.35 mmol) was dissolved in 1:1 DCM:MeOH (10 mL). TsOH (0.06 g, 0.35 mmol) was added and the reaction mixture was stirred for 1 h at rt. After the reaction was complete, the reaction mixture was concentrated under vacuum and then dissolved in ethyl acetate (100 mL). The organic layer was washed with sat. NaHCO$_3$, and then dried over MgSO$_4$. The solution was filtered and solvent was evaporated under reduced pressure and the residue was purified by silica gel flash column chromatography using a gradient elution of DCM to methanol up to 10%. The solvent was evaporated to afford a white solid: 0.40 g (61% yield).

(3,4)12G1-PE-(3,4,5)-3EO-G1-(OTHP)$_6$ (32bTHP): (3,4)12G1-PE-(OH)$_2$ (17a) (0.413 g, 0.382 mmol), (3,4,5)-3EOG1-(OTHP)$_3$—CO$_2$H (30b) (0.75 g, 0.916 mmol) and DPTS (0.11 g, 0.387 mmol) were dissolved in anhydrous DCM (7 mL). DCC (0.204 g, 0.99 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of ethyl acetate to methanol up to 7%. The sample was dried under high vacuum overnight to afford a colorless oil: 0.90 g (88% yield).

(3,4)12G1-PE-(3,4,5)-3EO-G1-(OH)$_6$ (32b): (3,4)12G1-PE-(3,4,5)-3EO-G1-(OTHP)$_6$ (32bTHP) (0.9 g, 0.34 mmol) was dissolved in 1:1 DCM:MeOH (10 mL). TsOH (0.09 g, 0.54 mmol) was added and the reaction mixture was stirred for 1 h at rt. After the reaction was complete, the reaction mixture was concentrated under vacuum and then dissolved in ethyl acetate (100 mL). The organic layer was washed with sat. NaHCO$_3$, and then dried over MgSO$_4$. The solution was filtered and solvent was evaporated under reduced pressure and the residue was purified by silica gel flash column chromatography using a gradient elution of DCM to methanol up to 10%. Solvent was evaporated to afford a white solid: 0.36 g (49% yield).

(3,5)12G1-PE-(3,4)-3EO-G1-(OTHP)$_4$ (32cTHP): (3,5)12G1-PE-(OH)$_2$ (17b) (0.36 g, 0.33 mmol), (3,4)-3EO-G1-(OTHP)$_2$—CO$_2$H (30a) (0.47 g, 0.80 mmol) and DPTS (0.1 g, 0.33 mmol) were dissolved in anhydrous DCM (7 mL). DCC (0.18 g, 0.86 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of ethyl acetate to methanol up to 5%. The sample was dried under high vacuum overnight to afford a colorless oil: 0.35 g (48% yield).

(3,5)12G1-PE-(3,4)-3EO-G1-(OH)$_4$ (32c): (3,5)12G1-PE-(3,4)-3EO-G1-(OTHP)$_4$ (32cTHP) (0.35 g, 0.16 mmol) was dissolved in 1:1 DCM:MeOH (10 mL). TsOH (0.03 g, 0.16 mmol) was added and the reaction mixture was stirred for 1 h at rt. After the reaction was complete, the reaction mixture was concentrated under vacuum and then dissolved in ethyl acetate (100 mL). The organic layer was washed with sat. NaHCO$_3$, and then dried over MgSO$_4$. The solution was filtered and solvent was evaporated under reduced pressure and the residue was purified by silica gel flash column chromatography using a gradient elution of DCM to methanol up to 10%. The solvent was evaporated to afford a white solid: 0.17 g (56% yield).

(3,5)12G1-PE-(3,4,5)-3EO-G1-(OTHP)$_6$ (32dTHP): (3,5) 12G1-PE-(OH)$_2$ (17b) (0.42 g, 0.387 mmol), (3,4,5)-3EOG1-(OTHP)$_3$—CO$_2$H (30b) (0.76 g, 0.928 mmol) and DPTS (0.11 g, 0.387 mmol) were dissolved in anhydrous DCM (7 mL). DCC (0.21 g, 1.0 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of ethyl acetate to methanol up to 7%. The sample was dried under high vacuum overnight to afford a colorless oil: 0.97 g (93% yield).

(3,5)12G1-PE-(3,4,5)-3EO-G1-(OH)$_6$ (32d): (3,5)12G1-PE-(3,4,5)-3EO-G1-(OTHP)$_6$ (32dTHP) (0.97 g, 0.36 mmol) was dissolved in 1:1 DCM:MeOH (7 mL). TsOH (0.09 g, 0.54 mmol) was added and the reaction mixture was stirred for 1 h at rt. After the reaction was complete, the reaction mixture was concentrated under vacuum and then dissolved in DCM (100 mL). The organic layer was washed with sat. NaHCO$_3$ and sat. NaCl, and then dried over MgSO$_4$. The solution was filtered and solvent was evaporated under reduced pressure and the residue was purified by silica gel flash column chromatography using a gradient elution of DCM to methanol up to 10%. Solvent was evaporated to afford a white solid: 0.21 g (27% yield).

(3,4,5)12G1-PE-(3,4,5)-3EO-G1-(OTHP)$_6$ (32eTHP): (3,4,5)12G1-PE-(OH)$_2$ (17c) (0.45 g, 0.31 mmol), (3,4,5)-3EO-G1-(OTHP)$_3$—CO$_2$H (30b) (0.75 g, 0.92 mmol) and DPTS (0.12 g, 0.42 mmol) were dissolved in anhydrous DCM (7 mL). DCC (0.25 g, 1.09 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of ethyl acetate to methanol up to 5%. The sample was dried under high vacuum overnight to afford a colorless oil: 0.60 g (63% yield).

(3,4,5)12G1-PE-(3,4,5)-3EO-G1-(OH)$_6$ (32e): (3,4,5) 12G1-PE-(3,4,5)-3EO-G1-(OTHP)$_6$ (32eTHP) (0.81 g, 0.265 mmol) was dissolved in 1:1 DCM:MeOH (32 mL). TsOH (0.07 g, 0.398 mmol) was added and the reaction mixture was stirred for 1 h at rt. After the reaction was complete, the reaction mixture was concentrated under vacuum and then dissolved in DCM (100 mL). The organic layer was washed with sat. NaHCO$_3$ and sat. NaCl, and then dried over MgSO$_4$. The solution was filtered and solvent was evaporated under reduced pressure and the residue was purified by silica gel flash column chromatography using a gradient elution of DCM to methanol up to 100%. The recovered product was dissolved in DCM and filtered through celite. Solvent was evaporated to afford a white solid: 0.45 g (67% yield).

HO-3EO-Bn (33): A mixture of triethylene glycol, benzyl bromide, and 50% NaOH was heated with stirring at 100° C. for 24 h. The mixture was cooled to room temperature, diluted with water, and extracted with Et$_2$O. The organic extracted were combined, dried over MgSO$_4$, and concentrated under vacuum. The remaining oil was purified by reduced pressure distillation (1 torr, 170° C.) to give a colorless liquid: 15.22 g (72%).

TsO-3EO-Bn (34): p-Toluenesulfonyl chloride (TsCl) was added dropwise into the solution of HO-3EO-Bn, and NaOH in water and THF mixture while maintaining the temperature at 0 to 5° C. The reaction mixture was stirred at 0° C. for 3 h. After the reaction was complete, it was poured into ice-water, extracted with CH$_2$Cl$_2$, washed with HCl (pH=1), brine, and dried over MgSO$_4$. The organic phase was concentrated and purified by column chromatography (silica gel, EtOAc/hexane=30:70) to give TsO-3EO-Bn (34) as a colorless liquid: 17.70 g (72%).

(3,4)-3EO-G1-(OBn)$_2$-CO$_2$CH$_3$ (35a): 3,4-dihydroxymethylbenzoate (0.59 g, 3.51 mmol) was dissolved in DMF (30 mL) that was previously degassed by bubbling nitrogen for 0.5 h. TsO-3EO-Bn (34 (3.05 g, 7.73 mmol), KI (0.29 g, 1.76 mmol), and K$_2$CO$_3$ (4.85 g, 35.1 mmol) were added, and the suspension was stirred 1.5 h at 70° C. The reaction mixture was then cooled to rt, poured into water (150 mL) and extracted with ethyl acetate (3×50 mL). The organic layers were combined, washed with water (150 mL) and dried over MgSO$_4$ then filtered. The solvent was removed under high vacuum to remove ethyl acetate and DMF respectively. The sample was purified using silica gel flash column chromatography using a gradient elution of acetate: hexanes to ethyl acetate. The sample was dried under high vacuum overnight to afford a colorless oil: 2.02 g (94% yield).

(3,5)-3EO-G1-(OBn)$_2$-CO$_2$CH$_3$ (35b): 3,5-Dihydroxymethyl benzoate (1.62 g, 9.66 mmol) was dissolved in DMF (40 mL) that was previously degassed by bubbling nitrogen for 0.5 h. TsO-3EO-Bn (8.00 g, 20.3 mmol) in DMF (20 mL), and K$_2$CO$_3$ (5.34 g, 38.6 mmol) were added, and the suspension was stirred overnight at 80° C. The reaction mixture was then cooled to room temperature and poured into water. The mixture was extracted with EtOAc, washed with water and brine, and dried over MgSO$_4$. The solvent was evaporated under vacuum and the residue was purified by column chromatography (silica gel, EtOAc/hexane=50: 50) to give (3,5)3EO-Bn-CO2CH3 as a colorless liquid: 5.68 g (96%).

(3,4)-3EO-G1-(OBn)$_2$-CO$_2$H (36a): (3,4)-3EO-G1-(OBn)$_2$-CO$_2$CH$_3$ (35a) (2.02 g, 3.30 mmol) was dissolved in 95% EtOH (60 mL). KOH (0.92 g, 16.48 mmol) in water (9 mL) was added and the reaction mixture was stirred at reflux for 1 h. The reaction mixture was then cooled to rt, poured into water (150 mL) and acidified to pH 1 with a few drops of 2 M HCl. The aqueous solution was extracted with ethyl acetate (3×50 mL). The ethyl acetate solution was washed with water (50 mL) and dried over MgSO$_4$ then filtered. The solvent was removed under vacuum, and the sample was dried under high vacuum overnight to afford a white solid: 1.60 g (81% yield). No further purification was necessary.

(3,5)-3EO-G1-(OBn)$_2$-CO$_2$H (36b): (3,4)-3EO-G1-(OBn)$_2$-CO$_2$CH$_3$ (35b) (5.00 g, 8.16 mmol) was dissolved in water (30 ml). KOH (2.29 g, 40.8 mmol) in water (20 ml) was added and the reaction mixture was stirred at reflux for 2 h. The reaction mixture was then cooled to room temperature, and acidified to pH=1 with 6M HCl. The solution was extracted with EtOAc, washed with water, brine, and dried over MgSO$_4$. The solvent was evaporated to give (3,5)3EO-Bn-CO2H as a colorless liquid: 4.87 g (100%).

(3,4)12G1-PE-(3,5)-3EO-G1-(Bn)$_4$ (37aBn): (3,4)12G1-PE-(OH)$_2$ (17a) (0.87 g, 0.80 mmol), (3,5)-3EO-G1-(OBn)$_2$-CO$_2$H (36b) (1.01 g, 1.69 mmol), and DPTS (0.24 g, 0.80 mmol) were dissolved in anhydrous CH$_2$Cl$_2$ (5 mL). DCC (0.43 g, 2.09 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; EtOAc/hexane=60:40) to give (3,4)12G1-PE-(3,5)-3EO-G1-(Bn)$_4$ (37aBn) as a colorless liquid: 1.66 g (92%).

(3,4)12G1-PE-(3,5)-3EO-G1-(OH)$_4$ (37a): (3,4)12G1-PE-(3,5)-3EO-G1-(Bn)$_4$ (37aBn) (1.40 g, 0.62 mmol) was dissolved in CH$_2$Cl$_2$ (40 mL) and diluted with MeOH (20 mL). 10% Pd/C (0.14 g) was added into the solution and then the reaction flask was evacuated and filled three times with H2. After stirring at room temperature overnight in H$_2$ atmosphere, the Pd/C was filtered off using celite pad and washed with THF. The solvent was evaporated off and purified by column chromatography (silica gel, MeOH/EtOAc=10:90) to give (3,4)12G1-PE-(3,5)-3EO-G1-(OH)$_4$ (37a) as a white solid: 1.06 g (91%).

(3,5)12G1-PE-(3,5)-3EO-G1-(Bn)$_4$ (37bBn): (3,5)12G1-PE-(OH)$_2$ (17b) (0.87 g, 0.80 mmol), (3,5)-3EO-G1-(OBn)$_2$-CO$_2$H (36b) (1.01 g, 1.69 mmol), and DPTS (0.24 g, 0.80 mmol) were dissolved in anhydrous CH$_2$Cl$_2$ (5 mL). DCC (0.43 g, 2.09 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; EtOAc/hexane=60:40) to give (3,5)12G1-PE-(3,5)-3EO-G1-(Bn)$_4$ (37bBn) as a colorless liquid: 1.56 g (87%).

(3,5)12G1-PE-(3,5)-3EO-G1-(OH)$_4$ (37b): (3,5)12G1-PE-(3,5)-3EO-G1-(Bn)$_4$ (37bBn) (1.40 g, 0.62 mmol) was dissolved in CH$_2$Cl$_2$ (40 mL) and diluted with MeOH (20 mL). 10% Pd/C (0.14 g) was added into the solution and then the reaction flask was evacuated and filled three times with H$_2$. After stirring at room temperature overnight in H$_2$ atmosphere, the Pd/C was filtered off using celite pad and washed with THF. The solvent was evaporated and the crude product was purified by column chromatography (silica gel, MeOH/EtOAc=10:90) to give (3,5)12G1-PE-(3,5)-3EOG1-(OH)$_4$ (37b) as a colorless liquid: 1.09 g (93%).

(3,4,5)12G1-PE-(3,4)-3EO-G1-(Bn)$_4$ (37cBn): (3,4,5)12G1-PE-(OH)$_2$ (17c) (1.03 g, 0.71 mmol), (3,4)-3EO-G1-(OBn)$_2$-CO$_2$H (36a) (0.94 g, 1.57 mmol) and DPTS (0.21 g, 0.71 mmol) were dissolved in anhydrous DCM (7 mL). DCC (0.38 g, 1.85 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of EtOAc to MeOH up to 5%, and the sample was dried under high vacuum overnight to afford a colorless oil: 1.60 g (86% yield).

(3,4,5)12G1-PE-(3,4)-3EO-G1-(OH)$_4$ (37c): (3,4,5)12G1-PE-(3,4)-3EO-G1-(Bn)$_4$ (37cBn) (1.6 g, 0.613 mmol) was dissolved in 1:1 DCM/MeOH (100 mL). Pd/C was added (160 mg) and the atmosphere purged and filled with hydrogen three times. The reaction mixture was then stirred overnight under a hydrogen atmosphere. The reaction mixture was filtered through celite and the solvent was evaporated. The residue was purified by silica gel flash column chromatography using a gradient elution of DCM to methanol up to 10%. The solvent was evaporated to afford a white solid: 1.04 g (75% yield).

(3,4,5)12G1-PE-(3,5)-3EO-G1-(Bn)$_4$ (37 dBn): (3,4,5)12G1-PE-(OH)$_2$ (17c) (1.02 g, 0.70 mmol), (3,5)-3EO-G1-(OBn)$_2$-CO$_2$H (36b) (0.88 g, 1.48 mmol), and DPTS (0.21 g, 0.70 mmol) were dissolved in anhydrous CH$_2$Cl$_2$ (5 mL). DCC (0.38 g, 1.83 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; EtOAc/hexane=60:40) to give (3,4,5)12-PE-(3,5)$_3$EO-Bn as a colorless liquid: 1.73 g (94%).

(3,4,5)12G1-PE-(3,5)-3EO-G1-(OH)$_4$ (37d): (3,4,5)12G1-PE-(3,5)-3EO-G1-(Bn)$_4$ (37 dBn) (1.50 g, 0.58 mmol) was dissolved in CH$_2$Cl$_2$ (20 mL) and diluted with MeOH (10 mL). 10% Pd/C (0.15 g) was added into the solution and then the reaction flask was evacuated and filled three times with H$_2$. After stirring at room temperature overnight in H$_2$ atmosphere, the Pd/C was filtered off using celite pad and washed with THF. The solvent was removed under vacuum and purified by column chromatography (silica gel, MeOH/EtOAc=10:90) to give (3,4,5)12G1-PE-(3,5)-3EO-G1-(OH)$_4$ (37d) as white solid: 1.08 g (83%).

(3,4)4G1-CO$_2$CH$_3$ (39a): 3,4-Dihydroxymethyl benzoate (9.00 g, 53.5 mmol) was dissolved in DMF (100 mL) that was previously degassed by bubbling nitrogen for 0.5 h. 1-Bromobutane (15.39 g, 112.4 mmol) in DMF (50 mL), and K$_2$CO$_3$ (29.58 g, 214 mmol) were added, and the suspension was stirred overnight at 70° C. The reaction mixture was then cooled to room temperature and poured into water. The precipitate was collected, passed through basic Al$_2$O$_3$ using CH$_2$Cl$_2$ as eluent to give (3,4)4G1-CO$_2$CH$_3$ (39a) as a white solid: 14.89 g (99%).

(3,5)4G1-CO$_2$CH$_3$ (39b): 3,5-Dihydroxymethyl benzoate (5.00 g, 29.7 mmol) was dissolved in DMF (60 mL) that was previously degassed by bubbling nitrogen for 0.5 h. 1-Bromobutane (8.56 g, 62.4 mmol) in DMF (40 mL), and K$_2$CO$_3$ (16.44 g, 119 mmol) were added, and the suspension was stirred overnight at 70° C. The reaction mixture was then cooled to room temperature and poured into water. The mixture was extracted with EtOAc, washed with water and brine, and dried over MgSO$_4$. The solvent was evaporated under vacuum and the residue was passed through basic Al$_2$O$_3$ using CH$_2$Cl$_2$ as eluent to give (3,5)4G1-CO$_2$CH$_3$ (39b) as a pale yellow liquid: 8.24 g (99%).

(3,4,5)4G1-CO$_2$CH$_3$ (39c): 3,4,5-Trihydroxymethyl benzoate (7.00 g, 38.0 mmol) was dissolved in DMF (80 mL) that was previously degassed by bubbling nitrogen for 0.5 h. 1-Bromobutane (16.14 g, 117.8 mmol) in DMF (10 mL), and K$_2$CO$_3$ (31.51 g, 228 mmol) were added, and the suspension was stirred overnight at 70° C. The reaction mixture was then cooled to room temperature and poured into water. The mixture was extracted with EtOAc, washed with water and brine, and dried over MgSO$_4$. The solvent was removed under vacuum and the residue was passed through basic Al$_2$O$_3$ using CH$_2$Cl$_2$ as eluent to give (3,4,5)4G1-CO$_2$CH$_3$ (39c) as a colorless liquid: 12.98 g (97%).

(3,4)6G1-CO$_2$CH$_3$ (40a): 3,4-Dihydroxymethylbenzoate (10.8 g, 65.4 mmol) was dissolved in DMF (125 mL) that was previously degassed by bubbling nitrogen for 0.5 h. 1-Bromohexane (10.8 g, 65.4 mmol), and K$_2$CO$_3$ (20.5 g, 148.5 mmol) were added, and the suspension was stirred overnight at 70° C. The reaction mixture was then cooled to rt, poured into water (300 mL) and extracted with DCM (4×75 mL). The organic layers were combined, washed with water (7×100 mL) and brine (75 mL), and dried over MgSO$_4$ then filtered. The solvent was removed under vacuum at low and then high vacuum to remove ethyl acetate and residual DMF respectively. The sample was purified using column chromatography on silica gel with a mobile phase of hexanes ramped to 2:8 ethyl acetate:hexanes and the sample was dried under high vacuum overnight to afford a colorless oil: 9.00 g (90% yield).

(3,5)6G1-CO$_2$CH$_3$ (40b): 3,5-Trihydroxymethylbenzoate (6.16 g, 36.6 mmol) was dissolved in DMF (100 mL) that was previously degassed by bubbling nitrogen for 0.5 h. 1-Bromohexane (13.34 g, 80.8 mmol), and K$_2$CO$_3$ (25.3 g, 183 mmol) were added, and the suspension was stirred overnight at 70° C. The reaction mixture was then cooled to rt, poured into water (300 mL) and extracted with DCM (4×75 mL). The organic layers were combined, washed with water (7×100 mL) and brine (75 mL), and dried over MgSO$_4$ then filtered. The solvent was removed under vacuum at low and then high vacuum to remove ethyl acetate and residual DMF respectively. The sample was purified by silica gel flash column chromatography using a gradient elution of hexanes to 1:1 ethyl acetate:hexanes, and the sample was dried under high vacuum overnight to afford a colorless oil: 12.30 g (100% yield).

(3,4,5)6G1-CO$_2$CH$_3$ (40c): 3,4,5-Trihydroxymethylbenzoate (5 g, 27.2 mmol) was dissolved in DMF (100 mL) that was previously degassed by bubbling nitrogen for 0.5 h. 1-Bromohexane (14.79 g, 89.6 mmol), and K$_2$CO$_3$ (28 g, 204 mmol) were added, and the suspension was stirred overnight at 70° C. The reaction mixture was then cooled to rt, poured into water (300 mL) and extracted with DCM (4×75 mL). The organic layers were combined, washed with water (7×100 mL) and brine (75 mL), and dried over MgSO$_4$ then filtered. The solvent was removed under vacuum. The sample was purified using column chromatography on silica gel with a mobile phase of hexanes ramped to 2:8 ethyl acetate:hexanes, and the sample was dried under high vacuum overnight to afford a colorless oil: 11.12 g (94% yield).

(3,4)8G1-CO$_2$CH$_3$ (41a):, 3,4-Dihydroxymethyl benzoate (6.42 g, 38.2 mmol) was dissolved in DMF (100 mL) that was previously degassed by bubbling nitrogen for 0.5 h. 1-Bromooctane (14.75 g, 76.36 mmol) in DMF (20 mL), and K$_2$CO$_3$ (21.11 g, 152.7 mmol) were added, and the suspension was stirred overnight at 70° C. The reaction mixture was then cooled to room temperature and poured into water. The precipitate was collected, passed through basic Al$_2$O$_3$ using CH$_2$Cl$_2$ as eluent to give (3,4)8G1-CO$_2$CH$_3$ (41a) as a white solid: 15.00 g (100%).

(3,5)8G1-CO$_2$CH$_3$ (41b): 3,5-Dihydroxymethyl benzoate (5.04 g, 30.0 mmol) was dissolved in DMF (60 mL) that was previously degassed by bubbling nitrogen for 0.5 h. 1-Bromooctane (12.17 g, 63.00 mmol) in DMF (40 mL), and K$_2$CO$_3$ (16.58 g, 120 mmol) were added, and the suspension was stirred overnight at 70° C. The reaction mixture was then cooled to room temperature and poured into water. The precipitate was collected, passed through basic Al$_2$O$_3$ using CH$_2$Cl$_2$ as eluent to give (3,5)8G1-CO$_2$CH$_3$ (41b) as a white solid: 11.36 g (100%).

(3,4,5)8G1-CO$_2$CH$_3$ (41c): 3,4,5-Trihydroxymethyl benzoate (4.60 g, 25.0 mmol) was dissolved in DMF (70 mL) that was previously degassed by bubbling nitrogen for 0.5 h. 1-Bromooctane (14.48 g, 75.00 mmol) in DMF (10 mL), and K$_2$CO$_3$ (20.73 g, 150.0 mmol) were added, and the suspension was stirred overnight at 70° C. The reaction mixture was then cooled to room temperature and poured into water. The mixture was extracted with EtOAc, washed with water and brine, and dried over MgSO$_4$. The solvent was evaporated under vacuum and the residue was passed through basic Al$_2$O$_3$ using CH$_2$Cl$_2$ as eluent to give (3,4,5)8G1-CO$_2$CH$_3$ (41c) as a white liquid: 12.71 g (98%).

(3,4)2-Ethyl8G1-CO$_2$CH$_3$ (42): 3,4-Dihydroxymethylbenzoate (2.6 g, 15.46 mmol) was dissolved in DMF (125 mL) that was previously degassed by bubbling nitrogen for 0.5 h. 3-Bromomethylhexane (6.57 g, 34 mmol), and K$_2$CO$_3$ (21.4 g, 154.6 mmol) were added, and the suspension was stirred overnight at 70° C. The reaction mixture was then cooled to rt, poured into water (200 mL) and extracted with DCM (4×100 mL). The organic layers were combined, washed with water (10×100 mL) and brine (100 mL), and dried over MgSO$_4$ then filtered. The solvent was removed under vacuum at low and then high vacuum to remove ethyl acetate and residual DMF respectively. The sample was purified using column chromatography on silica gel with a mobile phase of hexanes ramped to 3:7 ethyl acetate: hexanes, and the sample was dried under high vacuum overnight to afford a colorless oil: 5.34 g (88% yield). The product is a mixture of diastereomers.

(3,4)4G1-CO$_2$H (43a): (3,4)4G1-CO$_2$CH$_3$ (39a) (7.01 g, 25.0 mmol) was dissolved in 95% EtOH (30 ml). KOH (7.01 g, 125 mmol) in water (20 ml) was added and the reaction mixture was stirred at reflux for 2 h. The reaction mixture was then cooled to room temperature, poured into water, and acidified to pH=1 with 6M HCl. The precipitate was collected and recrystallized in acetone. The solid was filtered and dried under vacuum to give (3,4)4G1-CO$_2$H (43a) as a white solid: 5.98 g (90%).

(3,5)4G1-CO$_2$H (43b): (3,5)4G1-CO$_2$CH$_3$ (39b) (6.00 g, 21.4 mmol) was dissolved in 95% EtOH (40 ml). KOH (6.00 g, 107 mmol) in water (20 ml) was added and the reaction mixture was stirred at reflux for 2 h. The reaction mixture was then cooled to room temperature, poured into water, and acidified to pH=1 with 6M HCl. The precipitate was collected and dried under vacuum to give (3,5)4G1-CO$_2$H (43b) as a white solid: 5.60 g (98%).

(3,4,5)4G1-CO$_2$H (43c): (3,4,5)4G1-CO$_2$CH$_3$ (39c) (6.50 g, 18.4 mmol) was dissolved in 95% EtOH (20 ml). KOH (5.17 g, 92.2 mmol) in water (20 ml) was added and the reaction mixture was stirred at reflux for 2 h. The reaction mixture was then cooled to room temperature, poured into water, and acidified to pH=1 with 6M HCl. The solid was filtered and dried under vacuum to give (3,4,5)4G1-CO$_2$H (43c) as a white solid: 6.24 g (100%).

(3,5)6G1-CO$_2$H (44a): (3,5)6G1-CO$_2$CH$_3$ (40b) (12 g, 35.66 mmol) was dissolved in 95% EtOH (500 mL). KOH (10 g, 178 mmol) in water (100 mL) was added and the reaction mixture was stirred at reflux for 10 min. The reaction mixture was then cooled to rt, poured into water (200 mL) and acidified to pH=1 with 2 M HCl. The aqueous solution was extracted with ethyl acetate (5×100 mL). The ethyl acetate solution was washed with water (6×100 mL), brine (2×100 mL) and dried over MgSO$_4$ then filtered. The solvent was removed under vacuum, and the sample was dried under high vacuum overnight to afford a waxy white solid: 11.40 g (99% yield). No further purification was necessary.

(3,4,5)6G1-CO$_2$H (44b): (3,4,5)6G1-CO$_2$CH$_3$ (40c) (10.7 g, 24.52 mmol) was dissolved in 95% EtOH (250 mL). KOH (6.88 g, 122.62 mmol) in water (69 mL) was added and the reaction mixture was stirred at reflux for 2 h. The reaction mixture was then cooled to rt, poured into water (200 mL) and acidified to pH=1 with 2 M HCl. The aqueous solution was extracted with ethyl acetate (4×75 mL). The ethyl acetate solution was washed with water (5×100 mL), brine (100 mL) and dried over MgSO$_4$ then filtered. The solvent was removed under vacuum, and the sample was dried under high vacuum overnight to afford a waxy white solid: 10.35 g (100% yield). No further purification was necessary.

(3,4)8G1-CO$_2$H (45a): (3,4)8G1-CO$_2$CH$_3$ (41a) (7.85 g, 20.0 mmol) was dissolved in 95% EtOH (30 ml). KOH (5.61 g, 100 mmol) in water (30 ml) was added and the reaction mixture was stirred at reflux for 2 h. The reaction mixture was then cooled to room temperature, poured into water, and acidified to pH=1 with 6M HCl. The precipitate was collected and recrystallized in acetone. The solid was filtered and dried under vacuum to give (3,4)8G1-CO$_2$H (45a) as a white solid: 7.30 g (96%).

(3,5)8G1-CO$_2$H (45b): (3,5)8G1-CO$_2$CH$_3$ (41b) (6.00 g, 15.8 mmol) was dissolved in 95% EtOH (30 ml). KOH (4.45 g, 79.2 mmol) in water (20 ml) was added and the reaction mixture was stirred at reflux for 2 h. The reaction mixture was then cooled to room temperature, poured into water, and acidified to pH=1 with 6M HCl. The precipitate was collected and recrystallized in MeOH. The solid was filtered and dried under vacuum to give (3,5)8-CO2H as a white solid: 5.65 g (94%).

(3,4,5)8G1-CO$_2$H (45c): (3,4,5)8G1-CO$_2$CH$_3$ (41c) (7.03 g, 13.5 mmol) was dissolved in 95% EtOH (20 ml). KOH (3.79 g, 67.5 mmol) in water (20 ml) was added and the reaction mixture was stirred at reflux for 2 h. The reaction mixture was then cooled to room temperature, poured into water, and acidified to pH=1 with 6M HCl. The solid was filtered and dried under vacuum to give (3,4,5)8-CO$_2$H as a white solid: 6.71 g (98%).

(3,4)2-Ethyl8G1-CO$_2$H (46): (3,4)2-Ethyl8G1-CO$_2$CH$_3$ (42) (5.34 g, 13.6 mmol) was dissolved in 95% EtOH (160 mL). KOH (3.82 g, 68.01 mmol) in water (38 mL) was added and the reaction mixture was stirred at reflux for 10 min. The reaction mixture was then cooled to rt, poured into water (200 mL) and acidified to pH=1 with 2 M HCl. The aqueous solution was extracted with ethyl acetate (3×50 mL). The ethyl acetate solution was washed with water (5×100 mL), brine (100 mL) and dried over copious MgSO$_4$ then filtered. The solvent was removed under vacuum, and the sample was dried under high vacuum overnight to afford a colorless oil: 4.51 g (88% yield). No further purification was necessary. Product is a mixture of diastereomers.

(3,4)4G1-PE-(benzylidene) (47a): The monobenzacetal of pentaerythritol (1.65 g, 7.36 mmol), (3,4)4G1-CO$_2$H (43a) (4.12 g, 15.5 mmol), and DPTS (2.17 g, 7.36 mmol) were dissolved in anhydrous CH$_2$Cl$_2$ (15 mL). DCC (3.95 g, 19.1 mmol) dissolved in anhydrous CH$_2$Cl$_2$ (7 mL) was added, and the reaction mixture was stirred for 12 h at room temperature. After the reaction was complete, the mixture was diluted, filtered, and rinsed with Et$_2$O. The solvent was evaporated under vacuum and the residue was purified by column chromatography (silica gel; EtOAc/hexane=10:90) to give (3,4)4G1-PE-(benzylidene) (47a) as a colorless liquid: 5.19 g (98%).

(3,5)4G1-PE-(benzylidene) (47b): The monobenzacetal of pentaerythritol (1.64 g, 7.33 mmol), (3,5)4G1-CO$_2$H (43b) (4.10 g, 15.39 mmol), and DPTS (2.16 g, 7.33 mmol) were dissolved in anhydrous CH$_2$Cl$_2$ (15 mL). DCC (3.93 g, 19.1 mmol) dissolved in anhydrous CH$_2$Cl$_2$ (10 mL) was added, and the reaction mixture was stirred for 12 h at room temperature. After the reaction was complete, the mixture was diluted, filtered, and rinsed with Et$_2$O. The solvent was evaporated under vacuum and the residue was purified by column chromatography (silica gel; Et$_2$O/hexane=20:80) to give (3,5)4G1-PE-(benzylidene) (47b) as a white solid: 4.93 g (93%).

(3,4,5)4G1-PE-(benzylidene) (47c): The monobenzacetal of pentaerythritol (1.79 g, 8.00 mmol), (3,4,5)4G1-CO$_2$H (43c) (5.68 g, 16.8 mmol), and DPTS (2.35 g, 8.00 mmol) were dissolved in anhydrous CH$_2$Cl$_2$ (20 mL). DCC (4.29 g, 20.8 mmol) dissolved in anhydrous CH$_2$Cl$_2$ (10 mL) was added, and the reaction mixture was stirred for 12 h at room temperature. After the reaction was complete, the mixture was diluted, filtered, and rinsed with Et$_2$O. The solvent was evaporated under vacuum and the residue was purified by column chromatography (silica gel; Et$_2$O/hexane=25:75) to give (3,4,5)4G1-PE-(benzylidene) (47c) as a white solid: 6.65 g (96%).

(3,4)6G1-PE-(benzylidene) (48a): The monobenzacetal of pentaerythritol (1 g, 4.46 mmol), (3,4)6G1-CO$_2$H (1d) (3.16 g, 9.81 mmol) and DPTS (1.31 g, 4.46 mmol) were dissolved in anhydrous DCM (7 mL). DCC (2.39 g, 11.59 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified using silica gel flash column chromatography with gradient eluent of hexanes to EtOAc up to 40%, and the sample was dried under high vacuum overnight to afford a viscous colorless oil: 3.61 g (97% yield).

(3,5)6G1-PE-(benzylidene) (48b): The monobenzacetal of pentaerythritol (3.16 g, 14.1 mmol), (3,5)6G1-CO$_2$H (44a) (10 g, 31 mmol) and DPTS (4.15 g, 14.1 mmol) were dissolved in anhydrous DCM (7 mL). DCC (7.56 g, 36.66 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified using silica gel flash column chromatography with gradient eluent of hexanes to DCM up to 100%, and the sample was dried under high vacuum overnight to afford a white solid: 9.00 g (77% yield).

(3,4,5)6G1-PE-(benzylidene) (48c): The monobenzacetal of pentaerythritol (1 g, 4.46 mmol), (3,4,5)6G1-CO$_2$H (44b) (4.14 g, 9.81 mmol) and DPTS (1.31 g, 4.46 mmol) were dissolved in anhydrous DCM (7 mL). DCC (3 g, 14.53 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified using silica gel flash column chromatography with gradient eluent of hexanes to EtOAc up to 30%, and the sample was dried under high vacuum overnight to afford a viscous colorless oil: 4.53 g (98% yield).

(3,4)8G1-PE-(benzylidene) (49a): The monobenzacetal of pentaerythritol (1.20 g, 5.35 mmol), (3,4)8G1-CO$_2$H (45a) (4.25 g, 11.2 mmol), and DPTS (1.58 g, 5.35 mmol) were dissolved in anhydrous CH$_2$Cl$_2$ (24 mL). DCC (2.87 g, 13.9 mmol) dissolved in anhydrous CH$_2$Cl$_2$ (4 mL) was added, and the reaction mixture was stirred for 12 h at room temperature. After the reaction was complete, the mixture was diluted, filtered, and rinsed with Et$_2$O. The solvent was evaporated under vacuum and the residue was purified by column chromatography (silica gel; Et$_2$O/hexane=10:90) to give (3,4)8G1-PE-(benzylidene) (49a) as a colorless liquid: 5.02 g (99%).

(3,5)8G1-PE-(benzylidene) (49b): The monobenzacetal of pentaerythritol (1.23 g, 5.50 mmol), (3,5)8G1-CO$_2$H (45b) (4.37 g, 11.6 mmol), and DPTS (1.62 g, 5.50 mmol) were dissolved in anhydrous CH$_2$Cl$_2$ (30 mL). DCC (2.95 g, 14.3 mmol) dissolved in anhydrous CH$_2$Cl$_2$ (10 mL) was added, and the reaction mixture was stirred for 12 h at room temperature. After the reaction was complete, the mixture was diluted, filtered, and rinsed with Et$_2$O. The solvent was evaporated under vacuum and the residue was purified by column chromatography (silica gel; Et$_2$O/hexane=10:90) to give (3,5)8G1-PE-(benzylidene) (49b) as a colorless liquid: 5.15 g (99%).

(3,4,5)8G1-PE-(benzylidene) (49c): The monobenzacetal of pentaerythritol (1.12 g, 5.00 mmol), (3,5)8G1-CO$_2$H (45b) (5.32 g, 10.5 mmol), and DPTS (1.47 g, 5.00 mmol) were dissolved in anhydrous CH$_2$Cl$_2$ (15 mL). DCC (2.68 g, 13.0 mmol) dissolved in anhydrous CH$_2$Cl$_2$ (5 mL) was added, and the reaction mixture was stirred for 12 h at room temperature. After the reaction was complete, the mixture was diluted, filtered, and rinsed with Et$_2$O. The solvent was evaporated under vacuum and the residue was purified by column chromatography (silica gel; Et$_2$O/hexane=20:80) to give (3,4,5)8G1-PE-(benzylidene) (49c) as a colorless liquid: 5.77 g (96%).

(3,4)2-Ethyl8G1-PE-(benzylidene) (50): The monobenzacetal of pentaerythritol (1.21 g, 5.42 mmol), (3,4)2-Ethyl8G1-CO$_2$H (46) (4.51 g, 11.91 mmol) and DPTS (1.6 g, 5.42 mmol) were dissolved in anhydrous DCM (7 mL). DCC (2.91 g, 14.1 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient of hexanes to DCM up to 100%, and the sample was dried under high vacuum overnight to afford a colorless oil: 4.88 g (95% yield). Et$_2$O (3,4)4G1-PE-(OH)$_2$ (51a): (3,4)4G1-PE-(benzylidene) (47a) (5.00 g, 6.94 mmol) was dissolved in 1:2 MeOH:CH$_2$Cl$_2$ (60 mL), Pd/C (0.25 g) was added and the atmosphere purged and filled with hydrogen three times. The reaction mixture was then stirred overnight under a hydrogen atmosphere. The mixture was filtered through celite and the solvent was evaporated to give (3,4)4G1-PE-(OH)$_2$ (51a) as a white solid:4.10 (93%).

(3,5)4G1-PE-(OH)$_2$ (51b): (3,5)4G1-PE-(benzylidene) (47b) (4.00 g, 5.55 mmol) was dissolved in 1:2 MeOH:CH$_2$Cl$_2$ (60 mL), Pd/C (0.40 g) was added and the atmosphere purged and filled with hydrogen three times. The reaction mixture was then stirred overnight under a hydrogen atmosphere. The mixture was filtered through celite, and the solvent was evaporated to give (3,5)4G1-PE-(OH)$_2$ (51b) as a white solid:3.53 (100%).

(3,4,5)4G1-PE-(OH)$_2$ (51c): (3,4,5)4G1-PE-(benzylidene) (47c) (6.00 g, 6.94 mmol) was dissolved in 1:2 MeOH:CH$_2$Cl$_2$ (60 mL), Pd/C (0.10 g) was added and the atmosphere purged and filled with hydrogen three times. The reaction mixture was then stirred overnight under a hydrogen atmosphere. The mixture was filtered through celite, and concentrated to give (3,4,5)4G1-PE-(OH)$_2$ (51c) as a white solid:5.39 (100%).

(3,4)6G1-PE-(OH)$_2$ (52a): (3,4)6G1-PE-(benzylidene) (48a) (3.5 g, 4.2 mmol) was dissolved in 1:1 DCM:MeOH (200 mL). Pd/C was added (100 mg) and the atmosphere purged and filled with hydrogen three times. The reaction mixture was then stirred overnight under a hydrogen atmosphere. The reaction mixture was filtered through celite and the solvent was evaporated. In order to azeotropically remove residual methanol, the sample was dissolved in benzene, which was then removed under vacuum. This cycle was repeated twice and the sample was dried under high vacuum overnight to afford a white solid: 2.79 g (89% yield).

(3,5)6G1-PE-(OH)$_2$ (52b): (3,5)6G1-PE-(benzylidene) (48b) (8.4 g, 10.08 mmol) was dissolved in 1:1 DCM:MeOH (200 mL). Pd/C was added (130 mg) and the atmosphere purged and filled with hydrogen three times. The reaction mixture was then stirred overnight under a hydrogen atmosphere. The reaction mixture was filtered through celite and the solvent was evaporated. In order to azeotropically remove residual methanol, the sample was dissolved in benzene, which was then removed under vacuum. This cycle was repeated twice and the sample was dried under high vacuum overnight to afford a white solid: 7.34 g (98% yield).

(3,4,5)6G1-PE-(OH)$_2$ (52c): (3,4,5)6G1-PE-(benzylidene) (48c) (4.12 g, 3.99 mmol) was dissolved in 1:1 DCM:MeOH (200 mL). Pd/C was added (100 mg) and the atmosphere purged and filled with hydrogen three times. The reaction mixture was then stirred overnight under a hydrogen atmosphere. The reaction mixture was filtered through celite and the solvent was evaporated. In order to azeotropically remove residual methanol, the sample was dissolved in benzene, which was then removed under vacuum. This cycle was repeated twice and the sample was dried under high vacuum overnight to afford a white solid: 3.70 g (98% yield).

(3,4)8G1-PE-(OH)$_2$ (53a): (3,4)8G1-PE-(benzylidene) (49a) (5.00 g, 5.29 mmol) was dissolved in 1:2 MeOH:CH$_2$Cl$_2$ (60 mL), Pd/C (0.25 g) was added and the atmosphere purged and filled with hydrogen three times. The reaction mixture was then stirred overnight under a hydrogen atmosphere. The mixture was filtered through celite, concentrated and precipitated in MeOH to give (3,4)8G1-PE-(OH)$_2$ (53a) as a white solid: 4.29 (95%).

(3,5)8G1-PE-(OH)$_2$ (53b): (3,5)8G1-PE-(benzylidene) (49b) (4.50 g, 4.76 mmol) was dissolved in 1:2 MeOH:CH$_2$Cl$_2$ (60 mL), Pd/C (0.45 g) was added and the atmosphere purged and filled with hydrogen three times. The reaction mixture was then stirred overnight under a hydrogen atmosphere. The mixture was filtered through celite and the solvent was evaporated to give (3,5)8G1-PE-(OH)2 (53b) as a white solid: 4.08 g (100%).

(3,4,5)8G1-PE-(OH)$_2$ (53c): (3,4,5)8G1-PE-(benzylidene) (49c) (5.00 g, 4.16 mmol) was dissolved in 1:2 MeOH:CH$_2$Cl$_2$ (60 mL), Pd/C (0.10 g) was added and the flask was evacuated and filled with hydrogen three times. The reaction mixture was then stirred overnight under a hydrogen atmosphere. The mixture was filtered through celite and concentrated to give (3,4,5)8G1-PE-(OH)$_2$ (53c) as a white solid: 4.63 (100%).

(3,4)2-Ethyl8G1-PE-(OH)$_2$ (54): (3,4)2-Ethyl8G1-PE-(benzylidene) (50) (4.88 g, 5.16 mmol) was dissolved in 1:1 DCM:MeOH (200 mL). Pd/C was added (100 mg) and the atmosphere purged and filled with hydrogen three times. The reaction mixture was then stirred overnight under a hydrogen atmosphere. The reaction mixture was filtered through celite and the solvent was evaporated. In order to azeotropically remove residual methanol, the sample was dissolved in benzene, which was then removed under vacuum. This cycle was repeated twice and the sample was dried under high vacuum overnight to afford a viscous colorless oil: 4.10 g (93% yield).

(3,4)4G1-PE-(3,4)-3EO-G1-(OCH$_3$)$_4$ (55a): (3,4)4G1-PE-(OH)$_2$ (51a) (0.70 g, 1.1 mmol), (3,4)-3EO-G1-(OCH$_3$)$_2$—CO$_2$H (14a) (1.03 g, 2.31 mmol), and DPTS (0.32 g, 1.1 mmol) were dissolved in anhydrous CH$_2$Cl$_2$ (5 mL). DCC (0.59 g, 2.9 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; MeOH/EtOAc=5:95) to give (3,4)4G1-PE-(3,4)-3EO-G1-(OCH3)4 (55a) as a colorless liquid: 1.41 g (86%).

(3,4)4G1-PE-(3,5)-3EO-G1-(OCH$_3$)$_4$ (55b): (3,4)4G1-PE-(OH)$_2$ (51a) (0.63 g, 1.0 mmol), (3,5)-3EO-G1-(OCH$_3$)$_2$—CO$_2$H (14b) (0.94 g, 2.1 mmol), and DPTS (0.29 g, 1.0 mmol) were dissolved in anhydrous CH$_2$Cl$_2$ (5 mL). DCC (0.54 g, 2.6 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; MeOH/EtOAc=5:95) to give (3,4)4G1-PE-(3,5)-3EO-G1-(OCH$_3$)$_4$ (55b) as a colorless liquid: 1.33 g (89%).

(3,4)4G1-PE-(3,4,5)-3EO-G1-(OCH$_3$)$_6$ (55c): (3,4)4G1-PE-(OH)$_2$ (51a) (0.56 g, 0.88 mmol), (3,4,5)-3EO-G1-(OCH$_3$)$_3$—CO$_2$H (14c) (1.12 g, 1.85 mmol), and DPTS (0.26 g, 0.88 mmol) were dissolved in anhydrous CH$_2$Cl$_2$ (5 mL). DCC (0.47 g, 2.3 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; MeOH/EtOAc=5:95) to give (3,4)4G1-PE-(3,4,5)-3EO-G1-(OCH$_3$)$_6$ (55c) as a colorless liquid: 1.36 g (85%).

(3,5)4G1-PE-(3,4)-3EO-G1-(OCH$_3$)$_4$ (55d): (3,5)4G1-PE-(OH)$_2$ (51b) (0.63 g, 1.0 mmol), (3,4)-3EO-G1-(OCH$_3$)$_2$—CO$_2$H (14a) (0.94 g, 2.1 mmol), and DPTS (0.29 g, 1.0 mmol) were dissolved in anhydrous CH$_2$Cl$_2$ (5 mL). DCC (0.54 g, 2.6 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; MeOH/EtOAc=5:95) to give (3,5)4G1-PE-(3,4)-3EO-G1-(OCH$_3$)$_4$ (55d) as a colorless liquid: 1.20 g (80%).

(3,5)4G1-PE-(3,5)-3EO-G1-(OCH$_3$)$_4$ (55e): (3,5)4G1-PE-(OH)$_2$ (51b) (0.63 g, 1.0 mmol), (3,5)-3EO-G1-(OCH$_3$)$_2$—CO$_2$H (14b) (0.94 g, 2.1 mmol), and DPTS (0.29 g, 1.0 mmol) were dissolved in anhydrous CH$_2$Cl$_2$ (5 mL). DCC (0.54 g, 2.6 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; MeOH/EtOAc=4:96) to give (3,5)4G1-PE-(3,5)-3EO-G1-(OCH$_3$)$_4$ (55e) as a colorless liquid: 1.12 g (75%).

(3,5)4G1-PE-(3,4,5)-3EO-G1-(OCH$_3$)$_6$ (55f): (3,5)4G1-PE-(OH)$_2$ (51b) (0.54 g, 0.85 mmol), (3,4,5)-3EO-G1-(OCH$_3$)$_3$—CO$_2$H (14c) (1.09 g, 1.79 mmol), and DPTS (0.25 g, 0.85 mmol) were dissolved in anhydrous CH$_2$Cl$_2$ (5 mL). DCC (0.46 g, 2.21 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; MeOH/CH$_2$Cl$_2$=2.5:97.5) to give (3,5)4G1-PE-(3,4,5)-3EO-G1-(OCH$_3$)$_6$ (55f) as a colorless liquid: 0.82 g (53%).

(3,4,5)4G1-PE-(3,4)-3EO-G1-(OCH$_3$)$_4$ (55g): (3,4,5)4G1-PE-(OH)$_2$ (51c) (0.78 g, 1.0 mmol), (3,4)-3EO-G1-(OCH$_3$)$_2$—CO$_2$H (14a) (0.94 g, 2.1 mmol), and DPTS (0.29 g, 1.0 mmol) were dissolved in anhydrous CH$_2$Cl$_2$ (5 mL). DCC (0.54 g, 2.6 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; MeOH/EtOAc=5:95) to give (3,4,5)4G1-PE-(3,4)-3EO-G1-(OCH$_3$)$_4$ (55g) as a colorless liquid: 1.32 g (81%).

(3,4,5)4G1-PE-(3,5)-3EO-G1-(OCH$_3$)$_4$ (55h): (3,4,5)4G1-PE-(OH)$_2$ (51c) (0.78 g, 1.0 mmol), (3,5)-3EO-G1-(OCH$_3$)$_2$—CO$_2$H (14b) (0.94 g, 2.1 mmol), and DPTS (0.29 g, 1.0 mmol) were dissolved in anhydrous CH$_2$Cl$_2$ (5 mL). DCC (0.54 g, 2.6 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; MeOH/EtOAc=5:95) to give (3,4,5)4G1-PE-(3,5)-3EO-G1-(OCH$_3$)$_4$ (55h) as a colorless liquid: 1.45 g (89%).

(3,4,5)4G1-PE-(3,4,5)-3EO-G1-(OCH$_3$)$_6$ (55i): (3,4,5)4G1-PE-(OH)$_2$ (51c) (0.60 g, 0.77 mmol), (3,4,5)-3EO-G1-(OCH$_3$)$_3$—CO$_2$H (14c) (0.98 g, 1.6 mmol), and DPTS (0.23 g, 0.77 mmol) were dissolved in anhydrous CH$_2$Cl$_2$ (5 mL). DCC (0.41 g, 2.0 mmol) dissolved in anhydrous CH$_2$Cl$_2$ (2 mL) was added, and the reaction mixture was stirred for 12 h at room temperature. After the reaction was complete, the mixture was diluted with Et2O, filtered, and rinsed with Et2O. The solvent was evaporated under vacuum and the residue was purified by column chromatography (silica gel; MeOH/EtOAc=10:90) to give (3,4,5)4G1-PE-(3,4,5)-3EO-G1-(OCH$_3$)$_6$ (55i) as a colorless liquid: 1.36 g (91%).

(3,4)6G1-PE-(3,4)-3EO-G1-(OCH$_3$)$_4$ (56a): (3,4)6G1-PE-(OH)$_2$ (52a) (0.73 g, 0.97 mmol), (3,4)-3EO-G1-(OCH$_3$)$_2$—CO$_2$H (14a) (1 g, 2.24 mmol) and DPTS (0.3 g, 1.02 mmol) were dissolved in anhydrous DCM (7 mL). DCC (0.55 g, 2.65 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of ethyl acetate to methanol up to 5% to afford a colorless oil: 1.12 g (69% yield).

(3,4)6G1-PE-(3,5)-3EO-G1-(OCH$_3$)$_4$ (56b): (3,4)6G1-PE-(OH)$_2$ (52a) (0.76 g, 1.02 mmol), benzoic acid (3,5)-3EOG1-(OCH$_3$)$_2$—CO$_2$H (14b) (1 g, 2.24 mmol) and DPTS (0.3 g, 1.02 mmol) were dissolved in anhydrous DCM (7 mL). DCC (0.55 g, 2.65 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of ethyl acetate to methanol up to 5% to afford a colorless oil: 1.20 g (73% yield).

(3,4)6G1-PE-(3,4,5)-3EO-G1-(OCH$_3$)$_6$ (56c): (3,4)6G1-PE-(OH)$_2$ (52a) (0.57 g, 0.77 mmol), (3,4,5)-3EO-G1-(OCH$_3$)$_3$—CO$_2$H (14c) (1 g, 1.64 mmol) and DPTS (0.22 g, 0.75 mmol) were dissolved in anhydrous DCM (7 mL). DCC (0.40 g, 1.95 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of ethyl acetate to methanol up to 5% to afford a colorless oil: 0.92 g (62% yield).

(3,5)6G1-PE-(3,4)-3EO-G1-(OCH$_3$)$_4$ (56d): (3,5)6G1-PE-(OH)$_2$ (52b) (0.75 g, 1.02 mmol), (3,4)-3EO-G1-(OCH$_3$)$_2$—CO$_2$H (14a) (1 g, 2.24 mmol) and DPTS (0.3 g, 1.02 mmol) were dissolved in anhydrous DCM (7 mL). DCC (0.55 g, 2.65 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of ethyl acetate to methanol up to 5% to afford a colorless oil: 1.11 g (68% yield).

(3,5)6G1-PE-(3,5)-3EO-G1-(OCH$_3$)$_4$ (56e): (3,5)6G1-PE-(OH)$_2$ (52b) (0.71 g, 0.95 mmol), (3,5)-3EO-G1-(OCH$_3$)$_2$—CO$_2$H (14b) (1 g, 2.24 mmol) and DPTS (0.3 g, 1.02 mmol) were dissolved in anhydrous DCM (7 mL). DCC (0.55 g, 2.65 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of ethyl acetate to methanol up to 5% to afford a colorless oil: 1.26 g (83% yield).

(3,5)6G1-PE-(3,4,5)-3EO-G1-(OCH$_3$)$_6$ (56f): (3,5)6G1-PE-(OH)$_2$ (52b) (0.56 g, 0.75 mmol), (3,4,5)-3EO-G1-(OCH$_3$)$_3$—CO$_2$H (14c) (1 g, 1.64 mmol) and DPTS (0.22 g, 0.75 mmol) were dissolved in anhydrous DCM (7 mL). DCC (0.4 g, 1.95 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of ethyl acetate to methanol up to 5% to afford a colorless oil: 0.68 g (47% yield).

(3,4,5)6G1-PE-(3,4)-3EO-G1-(OCH$_3$)$_4$ (56g): (3,4,5)6G1-PE-(OH)$_2$ (52c) (0.88 g, 1.02 mmol), (3,4)-3EO-G1-(OCH$_3$)$_2$—CO$_2$H (14a) (1 g, 2.24 mmol) and DPTS (0.3 g, 1.02 mmol) were dissolved in anhydrous DCM (7 mL). DCC (0.55 g, 2.65 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of ethyl acetate to methanol up to 5% to afford a colorless oil: 0.80 g (44% yield).

(3,4,5)6G1-PE-(3,5)-3EO-G1-(OCH$_3$)$_4$ (56h): (3,4,5)6G1-PE-(OH)$_2$ (52c) (0.93 g, 0.98 mmol), (3,5)-3EO-G1-(OCH$_3$)$_2$—CO$_2$H (14b) (1 g, 2.24 mmol) and DPTS (0.3 g, 1.02 mmol) were dissolved in anhydrous DCM (7 mL). DCC (0.55 g, 2.65 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of ethyl acetate to methanol up to 5% to afford a colorless oil: 1.04 g (67% yield).

(3,4,5)6G1-PE-(3,4,5)-3EO-G1-(OCH$_3$)$_6$ (56i): (3,4,5)6G1-PE-(OH)$_2$ (52c) (0.43 g, 0.45 mmol), (3,4,5)-3EO-G1-(OCH$_3$)$_3$—CO$_2$H (14c) (0.69 g, 1.13 mmol) and DPTS (0.15 g, 0.52 mmol) were dissolved in anhydrous DCM (7 mL). DCC (0.276 g, 1.34 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of ethyl acetate to methanol up to 5% to afford a colorless oil: 0.73 g (76% yield).

(3,4)8G1-PE-(3,4)-3EO-G1-(OCH$_3$)$_4$ (57a): (3,4)8G1-PE-(OH)$_2$ (53a) (0.87 g, 1.02 mmol), (3,4)-3EO-G1-(OCH$_3$)$_2$—CO$_2$H (14a) (1 g, 2.24 mmol) and DPTS (0.3 g, 1.02 mmol) were dissolved in anhydrous DCM (7 mL). DCC (0.55 g, 2.65 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of ethyl acetate to methanol up to 5% to afford a colorless oil: 1.21 g (69% yield).

(3,4)8G1-PE-(3,5)-3EO-G1-(OCH$_3$)$_4$ (57b): (3,4)8G1-PE-(OH)$_2$ (53a) (0.86 g, 1.0 mmol), (3,5)-3EO-G1-(OCH$_3$)$_2$—CO$_2$H (14b) (0.94 g, 2.1 mmol), and DPTS (0.29 g, 1.0 mmol) were dissolved in anhydrous CH$_2$Cl$_2$ (5 mL). DCC (0.54 g, 2.6 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; MeOH/EtOAc=5:95) to give (3,4)8G1-PE-(3,5)-3EO-G1-(OCH$_3$)$_4$ (57b) as a colorless liquid: 1.51 g (88%).

(3,4)8G1-PE-(3,4,5)-3EO-G1-(OCH$_3$)$_6$ (57c): (3,4)8G1-PE-(OH)$_2$ (53a) (0.64 g, 0.75 mmol), (3,4,5)-3EO-G1-(OCH$_3$)$_3$—CO$_2$H (14c) (1 g, 1.65 mmol) and DPTS (0.22 g, 0.75 mmol) were dissolved in anhydrous DCM (7 mL). DCC (0.4 g, 1.95 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of ethyl acetate to methanol up to 5% to afford a colorless oil: 1.34 g (88% yield).

(3,5)8G1-PE-(3,4)-3EO-G1-(OCH$_3$)$_4$ (57d): (3,5)8G1-PE-(OH)$_2$ (53b) (0.75 g, 0.88 mmol), (3,4)-3EO-G1-(OCH$_3$)$_2$—CO$_2$H (14a) (0.82 g, 1.8 mmol), and DPTS (0.26 g, 0.88 mmol) were dissolved in anhydrous CH$_2$Cl$_2$ (5 mL). DCC (0.47 g, 2.3 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; MeOH/EtOAc=5:95) to give (3,5)8G1-PE-(3,4)-3EO-G1-(OCH$_3$)$_4$ (57d) as a colorless liquid: 1.28 g (85%).

(3,5)8G1-PE-(3,5)-3EO-G1-(OCH$_3$)$_4$ (57e): (3,5)8G1-PE-(OH)$_2$ (53b) (0.86 g, 1.0 mmol), (3,5)-3EO-G1-(OCH$_3$)$_2$—CO$_2$H (14b) (0.94 g, 2.1 mmol) and DPTS (0.29 g, 1.0 mmol) were dissolved in anhydrous CH$_2$Cl$_2$ (5 mL). DCC (0.54 g, 2.6 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel;

MeOH/EtOAc=4:96) to give (3,5)8G1-PE-(3,5)-3EO-G1-(OCH$_3$)$_4$ (57e) as a colorless liquid: 1.40 g (82%).

(3,5)8G1-PE-(3,4,5)-3EO-G1-(OCH$_3$)$_6$ (57f): (3,5)8G1-PE-(OH)$_2$ (53b) (0.63 g, 0.73 mmol), (3,4,5)-3EO-G1-(OCH$_3$)$_3$—CO$_2$H (14c) (0.94 g, 1.54 mmol), and DPTS (0.22 g, 0.73 mmol) were dissolved in anhydrous CH$_2$Cl$_2$ (5 mL). DCC (0.39 g, 1.91 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; MeOH/EtOAc=5:95) to give (3,5)8G1-PE-(3,4,5)-3EO-G1-(OCH$_3$)$_6$ (57f) as a colorless liquid: 1.01 g (67%).

(3,4,5)8G1-PE-(3,4)-3EO-G1-(OCH$_3$)$_4$ (57g): (3,4,5)8G1-PE-(OH)$_2$ (53c) (0.95 g, 0.85 mmol), (3,4)-3EO-G1-(OCH$_3$)$_2$—CO$_2$H (14a) (0.80 g, 1.8 mmol), and DPTS (0.25 g, 0.85 mmol) were dissolved in anhydrous CH$_2$Cl$_2$ (5 mL). DCC (0.46 g, 2.2 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; MeOH/EtOAc=5:95) to give (3,4,5)8G1-PE-(3,4)-3EO-G1-(OCH$_3$)$_4$ (57g) as a colorless liquid: 1.45 g (87%).

(3,4,5)8G1-PE-(3,5)-3EO-G1-(OCH$_3$)$_4$ (57h): (3,4,5)8G1-PE-(OH)$_2$ (53c) (0.95 g, 0.85 mmol), (3,5)-3EO-G1-(OCH$_3$)$_2$—CO$_2$H (14b) (0.80 g, 1.8 mmol), and DPTS (0.25 g, 0.85 mmol) were dissolved in anhydrous CH$_2$Cl$_2$ (5 mL). DCC (0.40 g, 2.2 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; MeOH/EtOAc=4:96) to give (3,4,5)8G1-PE-(3,5)-3EO-G1-(OCH$_3$)$_4$ (57h) as a colorless liquid: 1.05 g (63%).

(3,4,5)8G1-PE-(3,4,5)-3EO-G1-(OCH$_3$)$_6$ (57i): (3,4,5)8G1-PE-(OH)$_2$ (53c) (0.73 g, 0.65 mmol), (3,4,5)-3EO-G1-(OCH$_3$)$_3$—CO$_2$H (14c) (0.84 g, 1.4 mmol), and DPTS (0.19 g, 0.65 mmol) were dissolved in anhydrous CH$_2$Cl$_2$ (5 mL). DCC (0.35 g, 1.7 mmol) dissolved in anhydrous CH$_2$Cl$_2$ (2 mL) was added, and the reaction mixture was stirred for 12 h at room temperature. After the reaction was complete, the mixture was diluted with Et$_2$O, filtered, and rinsed with Et$_2$O. The solvent was evaporated under vacuum and the residue was purified by column chromatography (silica gel; MeOH/EtOAc=5:95) to give (3,4,5)8G1-PE-(3,4,5)-3EO-G1-(OCH$_3$)$_6$ (57i) as a colorless liquid: 1.09 g (73%).

(3,4)2-Ethyl8G1-PE-(3,4)-3EO-G1-(OCH$_3$)$_4$ (58a): (3,4)2-Ethyl8G1-PE-(OH)$_2$ (54) (0.69 g, 0.80 mmol), (3,4)-3EOG1-(OCH$_3$)$_2$—CO$_2$H (14a) (0.79 g, 1.77 mmol) and DPTS (0.24 g, 0.8 mmol) were dissolved in anhydrous DCM (7 mL). DCC (0.43 g, 2.08 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was by silica gel flash column chromatography using a gradient elution of ethyl acetate to methanol up to 5% to afford a colorless oil: 1.18 g (86% yield).

(3,4)2-Ethyl8G1-PE-(3,4,5)-3EO-G1-(OCH$_3$)$_6$ (58b):(3,4)2-Ethyl8G1-PE-(OH)$_2$ (54) (0.64 g, 0.75 mmol), (3,4,5)-3EO-G1-(OCH$_3$)$_3$—CO$_2$H (14c) (1 g, 1.65 mmol) and DPTS (0.22 g, 0.75 mmol) were dissolved in anhydrous DCM (7 mL). DCC (0.4 g, 1.95 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by silica gel flash column chromatography using a gradient elution of ethyl acetate to methanol up to 5% to afford a colorless oil: 0.90 g (59% yield).

(3,4,5)allylG1-CO$_2$CH$_3$ (59): 3,4,5-Trihydroxymethyl benzoate (2.76 g, 15 mmol) was dissolved in acetone (60 mL). K$_2$CO$_3$ (6.48 g, 46.9 mmol) and allyl bromide (5.67 g, 56.9 mmol) were added, and the suspension was stirred at reflux overnight. The reaction mixture was then cooled to room temperature and concentrated. The mixture was extracted with CH$_2$Cl$_2$, washed with water and brine, and dried over MgSO$_4$. The solvent was evaporated under vacuum and the residue was purified by column chromatography (silica gel, EtOAc/hexane=5:95) to give (3,4,5)allylG1-CO$_2$CH$_3$ (59) as a colorless liquid: 4.05 g (89%).

(3,4,5)allylG1-CO$_2$H (60): (3,4,5)allylG1-CO$_2$CH$_3$ (59) (4.00 g, 13.1 mmol) was dissolved in 95% EtOH (30 mL). KOH (3.69 g, 65.7 mmol) in water (10 ml) was added and the reaction mixture was stirred at reflux for 2 h. The reaction mixture was then cooled to room temperature, and acidified with 6M HCl carefully to pH=2. The precipitate was stirred for 10 min and then filtered under vacuum filtration, rinsed with water and dried in vacuum to give (3,4,5)allylG1-CO$_2$H (60) as a white solid: 3.64 (95%).

(3,4)12G1-PE-G-G1-(allyl)$_6$ (61a): (3,5)12G1-PE-(OH)$_2$ (17a) (1.00 g, 0.92 mmol), (3,4,5)allylG1-CO$_2$H (60) (0.59 g, 2.03 mmol), and DPTS (0.27 g, 0.92 mmol) were dissolved in anhydrous CH$_2$Cl$_2$ (5 mL). DCC (0.50 g, 2.40 mmol) dissolved in anhydrous CH$_2$Cl$_2$ (3 mL) was added, and the reaction mixture was stirred for 24 h at room temperature. After the reaction was complete, the mixture was diluted with hexane, filtered, and rinsed with hexane. The solvent was evaporated under vacuum and the residue was purified by column chromatography (silica gel; EtOAc/hexane=10:90) to give (3,4)12G1-PE-G-G1-(allyl)$_6$ (61a) as a white solid: 1.47 g (98%).

(3,5)12G1-PE-G-G1-(allyl)$_6$ (61b): (3,5)12G1-PE-(OH)$_2$ (17b) (1.00 g, 0.92 mmol), (3,4,5)allylG1-CO$_2$H (60) (0.59 g, 2.03 mmol), and DPTS (0.27 g, 0.92 mmol) were dissolved in anhydrous CH$_2$Cl$_2$ (5 mL). DCC (0.50 g, 2.40 mmol) dissolved in anhydrous CH$_2$Cl$_2$ (3 mL) was added, and the reaction mixture was stirred for 24 h at room temperature. After the reaction was complete, the mixture was diluted with hexane, filtered and rinsed with hexane. The solvent was evaporated under vacuum and the residue was purified by column chromatography (silica gel; EtOAc/hexane=5:95) to give (3,5)12G1-PE-G-G1-(allyl)$_6$ (61b) as a white solid: 1.40 g (93%).

(3,4,5)12G1-PE-G-G1-(allyl)$_6$ (61c): (3,4,5)12G1-PE-(OH)$_2$ (17c) (1.10 g, 0.76 mmol), (3,4,5)allylG1-CO$_2$H (60) (0.48 g, 1.67 mmol), and DPTS (0.22 g, 0.76 mmol) were dissolved in anhydrous CH$_2$Cl$_2$ (5 mL). DCC (0.41 g, 1.97 mmol) dissolved in anhydrous CH$_2$Cl$_2$ (2 mL) was added, and the reaction mixture was stirred for 24 h at room temperature. After the reaction was complete, the mixture was diluted with hexane, filtered, and rinsed with hexane. The solvent was evaporated under vacuum and the residue was purified by column chromatography (silica gel; EtOAc/hexane=10:90) to give (3,4,5)12G1-PE-G-G1-(allyl)$_6$ (61c) as a white solid: 1.48 g (98%).

(3,4)12G1-PE-G-G1-(OH)$_{12}$ (62a): K$_2$OsO$_4$·2H$_2$O (4.45 mg, 0.017 mmol) was added to a solution of the (3,4)12G1-PE-G-G1-(allyl)$_6$ (61a) (0.90 g, 0.55 mmol), N-methylmorpholine oxide (NMO) (0.43, 3.65 mmol) and citric acid (0.21 g, 1.11 mmol) in acetone/distilled water/t-butyl alcohol. The mixture was stirred at room temperature for 24 h. After the reaction was complete, the reaction mixture was concentrated, purified by column chromatography (silica gel, MeOH/CH$_2$Cl$_2$=20:80), and precipitated in acetone to give (3,4)12G1-PE-G-G1-(OH)$_{12}$ (62a) as a white solid: 0.51 g (51%).

(3,5)12G1-PE-G-G1-(OH)$_{12}$ (62b): K$_2$OsO$_4$·2H$_2$O (6.12 mg, 0.017 mmol) in water (2 mL) was added to a solution of the (3,5)12G1-PE-G-G1-(allyl)$_6$ (61b) (0.90 g, 0.55 mmol), N-methylmorpholine oxide (NMO) (0.43, 3.65 mmol) and citric acid (0.21 g, 1.11 mmol) in acetone (5 mL), distilled water (10 mL), and t-butyl alcohol (10 mL). The mixture was stirred at room temperature for 12 h. After the reaction was complete, the reaction mixture was concentrated, purified by column chromatography (silica gel, MeOH/CH$_2$Cl$_2$=20:80), and precipitated in acetone to give (3,5)12G1-PE-G-G1-(OH)$_{12}$ (62b) as a white solid: 0.47 g (47%).

(3,4,5)12G1-PE-G-G1-(OH)$_{12}$ (62c): K$_2$OsO$_4$·2H$_2$O (5.52 mg, 0.015 mmol) in water (2 mL) was added to a solution of the (3,4,5)12G1-PE-G-G1-(allyl)$_6$ (61c) (1.00 g, 0.50 mmol), N-methylmorpholine oxide (NMO) (0.39, 3.31 mmol) and citric acid (0.19 g, 1.00 mmol) in acetone (5 mL), distilled water (10 mL), and t-butyl alcohol (10 mL). The mixture was stirred at room temperature for 24 h. After the reaction was complete, the reaction mixture was concentrated, purified by column chromatography (silica gel, MeOH/CH$_2$Cl$_2$=20:80), and precipitated in acetone to give (3,4,5)12G1-PE-G-G1-(OH)$_{12}$ (62c) as a white solid: 0.74 g (67%).

(3,4,5)12G1-APD-(OH)—(CO$_2$CH$_3$) (65): D/L methyl serine (0.32 g, 2.07 mmol) was dissolved in DMSO (3 ml) and then diluted with THF (12 mL). NaHCO$_3$ and 5-(bromomethyl)-1,2,3-tris(dodecyloxy)benzene (4.50 g, 6.22 mmol) were added and the reaction mixture was refluxed under N$_2$ atmosphere overnight. The reaction mixture was cooled down to room temperature and cold water was added. The mixture was extracted with EtOAc, washed with water and brine, and dried over MgSO$_4$. The combined organic phase was concentrated and purified by column chromatography (gradient EtOAc/hexane=0-10%) to give (3,4,5)12G1-APD-(OH)—(CO$_2$CH$_3$) (65) as a white solid: 2.34 g (80%).

(3,4,5)12G1-APD-(OH)$_2$ (66): (3,4,5)12G1-APD-(OH)—(CO$_2$CH$_3$) (65) (2.34 g, 1.67 mmol) in dry THF (20 mL) was added dropwise into a slurry of LiAlH$_4$ (0.19 g, 5.00 mmol) in dry THF (30 mL) in N$_2$ atmosphere at 0° C. The mixture was stirred at room temperature for 2 h. After the reaction was complete, it was cooled down to 0° C. and quenched by successive addition of H$_2$O (0.5 mL), 15% NaOH (0.5 mL), and H$_2$O (1.5 mL) until H$_2$ evolution ceased. The reaction mixture was then filtered through celite and washed with THF. The filtrate was dried over MgSO$_4$, concentrated and recrystallized in acetone to give (3,4,5)12G1-APD-(OH)$_2$ (66) as a white solid: 2.20 g (96%).

General Procedure for the allylation of alcohol (Yamazaki, Polym. J. 17, 377-384 (1985)): 50% NaOH solution was added to a solution of the alcohol, allyl bromide (5 equiv. per OH group) and tetrabutyl ammonium bromide (TBAB) (0.4 equiv.) as phase-transfer catalyst in DMSO/THF (1:3) at 60° C. The reaction mixture was then stirred at 60° C. for 12 h. After the mixture was cooled down to room temperature, sat. NH4Cl was added, and extracted with Et$_2$O, washed with water, and brine, and dried with MgSO$_4$. The solvent was evaporated and the crude oil was purified by column chromatography.

(3,4,5)12G1-APD-(allyl)$_2$ (67): Reaction conditions and workup were as described above, with (3,4,5)12G1-APD-(OH)$_2$ (66) (2.57 g, 1.87 mmol), allyl bromide (1.63 mL, 18.66 mmol), TBAB (0.24 g, 0.746 mmol), and 50% NaOH (6 mL) in DMSO/THF (6 mL). The crude oil was purified by column chromatography (Et$_2$O/hexane=5:95) to give (3,4,5)12G1-APD-(allyl)$_2$ (67) as a colorless liquid: 2.55 g (94%).

General Procedure for the Dihydroxylation (Haag, J. Am. Chem. Soc. 122, 2954-2955 (2000) and Wyszogrodzka, Eur. J. Org. Chem., 53-63, (2008)): K$_2$OsO$_4$·2H$_2$O (0.5 mol % per allyl group) was added to a solution of the allyl ether and N-methylmorpholine oxide (NMO) (1.1 equiv. per allyl group) in acetone/distilled water/t-butyl alcohol. The mixture was stirred at 40° C. for 12 h. After the reaction was complete, the reaction mixture was concentrated, purified by column chromatography, and precipitated in acetone.

(3,4,5)12G1-APD-G-G1-(OH)$_4$ (68): Reaction conditions and workup were as described above, with (3,4,5)12G1-APD-(allyl)$_2$ (67) (2.82 g, 1.93 mmol), NMO (0.50 g, 4.26 mmol), K$_2$OsO$_4$·2H$_2$O (7.1 mg, 0.0193 mmol) in acetone/water/ter butyl alcohol (4 mL/1 mL/6 mL). The crude product was purified by column chromatography (MeOH/CH$_2$Cl$_2$=5:95) and precipitated in acetone to give (3,4,5)12G1-APD-G-G1-(OH)$_4$ (68) as a white solid: 1.83 g (62%).

(3,4,5)12G1-APD-G-G1-(allyl)$_4$ (69): Reaction conditions and workup were as described for compound (67), with (3,4,5)12G1-APD-G-G1-(OH)$_4$ (68) (1.60 g, 1.05 mmol), allyl bromide (1.83 mL, 20.98 mmol), TBAB (0.14 g, 0.420 mmol), and 50% NaOH (6 mL) in DMSO/THF (6 mL). The crude oil was purified by column chromatography (Et$_2$O/hexane=5:95) to give (3,4,5)12G1-APD-G-G1-(allyl)$_4$ (69) as a colorless liquid: 1.57 g (89%).

(3,4,5)12G1-APD-G-G2-(OH)$_8$ (70): Reaction conditions and workup were as described for 68, with (3,4,5)12G1-APD-G-G1-(allyl)$_4$ (69) (1.20 g, 0.711 mmol), NMO (0.37 g, 3.13 mmol), K$_2$OsO$_4$·2H$_2$O (5.3 mg, 0.0142 mmol) in acetone/water/t-butyl alcohol (5 mL/3 mL/6 mL). The crude product was purified by column chromatography (MeOH/CH$_2$Cl$_2$=10:90) and precipitated in acetone to give (3,4,5)12G1-APD-G-G2-(OH)$_8$ (70) as a white solid: 0.30 g (23%).

(3,4,5)12G1-CH$_2$Br (71): (3,4,5)12G1-CH$_2$OH (80c) (4.80 g, 7.26 mmol) was dissolved in dry THF. PPh$_3$ freshly recrystallized from hexane was added and the reaction mixture was stirred for 10 min. N-bromosuccinamide (NBS) was then added and the mixture was stirred for additional 2 h. The reaction mixture was precipitated in cold MeOH to give the white solid: 4.82 g (92%).

(3,4,5)12G1-PE-(3,4,5)$_1$-1EO-G1-(OTHP)$_3$ (72THP): This product was recovered as a side product of the synthesis of (3,4)12G1-PE-(3,4,5)-1EO-G1-(OTHP)$_3$ (31aTHP) when acetic acid was present in the starting benzoic acid (3,4,5)-1EO-G1-(OTHP)$_3$—CO$_2$H (29) due to the use of acetic acid in an early, unoptimized quenching procedure.

(3,4,5)12G1-PE-(3,4,5)$_1$-1EO-G1-(OH)$_3$ (72): (3,4,5)12G1-PE-(3,4,5)$_1$-1EO-G1-(OTHP)$_3$ (72THP) (0.64 g, 0.315 mmol) was dissolved in 1:1 DCM:MeOH (10 mL). TsOH (0.04 g, 0.25 mmol) was added and the reaction mixture was stirred for 1 h at rt. After the reaction was complete, the reaction mixture was concentrated under vacuum and then dissolved in DCM (100 mL). The organic layer was washed with sat. NaHCO$_3$ and sat. NaCl, and then dried over MgSO$_4$. The solution was filtered and the solvent was evaporated under reduced pressure and purified using column chromatography on silica gel with a mobile phase of ethyl acetate. The solvent was evaporated to afford a white solid: 0.39 g (70% yield).

(3,4)12G1-PE-TP-G1-(Br)$_2$ (73a): (3,4)12G1-PE-(OH)$_2$ (17a) (3 g, 2.77 mmol) was dissolved in dry CH$_2$Cl$_2$ (15 mL) and pyridine (0.9 mL, 11.09 mmol). The reaction mixture was cooled to 0° C. and a solution of 2-bromopropionyl bromide (1.16 mL, 11.09 mmol) in CH$_2$Cl$_2$ (20 mL) was added dropwise. The reaction mixture was stirred for an additional 10 min. The reaction mixture was diluted in DCM (200 mL) and washed with water (2×100 mL), NaHCO$_3$ (aq. sat., 100 mL), water (100 mL) and brine (100 mL). The organic phase was dried over MgSO$_4$ and concentrated. The crude product was purified by column chromatography on silica gel with a mobile phase of DCM to give (3,4)12G1-PETP-G1-(Br)$_2$ (73a) as a white solid: 3.74 g (100%). Mixture of diastereomers.

(3,5)12G1-PE-TP-G1-(Br)$_2$ (73b): (3,5)12G1-PE-(OH)$_2$ (17b) (2.00 g, 1.85 mmol) was dissolved in dry CH$_2$Cl$_2$ (6 mL) and pyridine (3 mL). The reaction mixture was cooled to 0° C. and a solution of 2-bromopropionyl bromide (0.78 mL, 7.4 mmol) in CH$_2$Cl$_2$ (12 mL) was added dropwise. The reaction mixture was stirred for an additional 30 min. The reaction mixture was diluted in Et$_2$O and washed with water and brine. The organic phase was dried over MgSO$_4$ and concentrated. The crude product was purified by column chromatography (silica gel; Et$_2$O/Hexane=10:90 gradient to Et$_2$O/Hexane=20:80) to give (3,5)12G1-PE-TP-G1-(Br)$_2$ (73b) as a colorless oil: 2.35 g (94%).

(3,4,5)12G1-PE-aBr-G1-(Br)$_2$ (73c): (3,4,5)12G1-PE-(OH)$_2$ (17c) (1 g, 0.67 mmol) was dissolved in dry CH$_2$Cl$_2$ (5 mL) and pyridine (0.18 mL, 2.21 mmol). The reaction mixture was cooled to 0° C. and a solution of 2-Bromopropionyl bromide (0.2 mL, 1.94 mmol) in CH$_2$Cl$_2$ (10 mL) was added dropwise. The reaction mixture was stirred for an additional 10 min. The reaction mixture was diluted in diethylether (100 mL) and washed with water (3×50 mL) and brine (100 mL). The organic phase was dried over MgSO$_4$ and concentrated. The crude product was purified by column chromatography on silica gel with a mobile phase of DCM to give (3,4,5)12G1-PE-aBr-G1-(Br)$_2$ (73c) as a clear oil: 1.13 g (98%). Mixture of diastereomers.

(3,4)12G1-PE-TP-G1-(OH)$_4$ (74a): To a solution of (3,4)12G1-PE-TP-G1-(Br)$_2$ (73a) (3.63 g, 2.69 mmol), and 1-thioglycerol (0.51 mL, 5.9 mmol) in CH$_2$Cl$_2$ (7 mL) was added Et$_3$N (1.02 mL, 5.9 mmol) dropwise via syringe at 25° C. After the complete conversion determined by MALDI-TOF and TLC, the reaction mixture was diluted in DCM (100 mL) and washed with water (3×100 mL) and brine (100 mL). The organic phase was dried over MgSO$_4$ and concentrated. The crude product was purified by silica gel flash column chromatography using a gradient elution of 1:1 hexanes:EtOAc to EtOAc to give (3,4)12G1-PE-TP-G1-(OH)$_4$ (74a) as a white solid: 3.31 g (88%). Complex mixture of diastereomers.

(3,5)12G1-PE-TP-G1-(OH)$_4$ (74b): To a solution of (3,5)12G1-PE-TP-G1-(Br)$_2$ (73b) (2.03 g, 1.5 mmol), and 1-thioglycerol (0.39 g, 3.6 mmol) in CH$_2$Cl$_2$ (3 mL) and CH$_3$CN (2 mL) was added a solution of Et$_3$N (0.36 g, 3.6 mmol) in CH$_3$CN (2 mL) dropwise via syringe at 25° C. After the complete conversion determined by MALDI-TOF and TLC, the Et3NHBr salts were precipitated in acetone and the reaction mixture was filtered and concentrated. The crude product was purified by column chromatography (silica gel, EtOAc/Hexane=50:50 gradient to EtOAc/Hexane=70:30) to give (3,5)12G1-PE-TP-G1-(OH)$_4$ (74b) as a white solid: 1.81 g (86%).

(3,4,5)12G1-PE-TP-G1-(OH)$_4$ (74c)45: To a solution of (3,4,5)12G1-PE-TP-G1-(Br)$_2$ (73c) (3.16 g, 1.84 mmol), and 1-thioglycerol (0.48 mL, 5.5 mmol) in CH$_2$Cl$_2$ (5 mL) and MeCN (5 mL) was added Et$_3$N (0.77 mL, 5.5 mmol) dropwise via syringe at 25° C. After the complete conversion determined by MALDI-TOF and TLC, the reaction mixture was diluted in EtOAc (150 mL) and washed with water (3×100 mL) and brine (100 mL). The organic phase was dried over MgSO$_4$ and concentrated. The crude product was purified by silica gel flash column chromatography using a gradient elution of 1:1 hexanes:EtOAc to EtOAc to give (3,4,5)12G1-PE-TP-G1-(OH)$_4$ (74c) as a white solid: 3.04 g (93%). Mixture of diastereomers.

(3,4)12G1-PE-TP-G2-(Br)$_4$ (75a): (3,4)12G1-PE-TP-G1-(OH)$_4$ (74a) (3 g, 2.13 mmol) was dissolved in dry CH$_2$Cl$_2$ (15 mL) and pyridine (1.03 mL, 12.78 mmol). The reaction mixture was cooled to 0° C. and a solution of 2-bromopropionyl bromide (1.34 mL, 12.78 mmol) in CH$_2$Cl$_2$ (30 mL) was added dropwise. The reaction mixture was stirred for an additional 10 min. The reaction mixture was diluted in DCM (150 mL) and washed with water (2×100 mL), NaHCO$_3$ (aq. sat., 100 mL), water (100 mL) and brine (100 mL). The organic phase was dried over MgSO$_4$ and concentrated. The crude product was purified by silica gel flash column chromatography using a gradient elution of DCM up to 3% EtOAc/DCM to give (3,4)12G1-PE-TP-G2-(Br)$_4$ (75a) as a white solid: 3.9 g (94%). Mixture of diastereomers.

(3,5)12G1-PE-TP-G2-(Br)$_4$ (75b): (3,4)12G1-PE-TP-G1-(OH)$_4$ (74b) (4.42 g, 3.14 mmol) was dissolved in dry CH$_2$Cl$_2$ (13 mL) and pyridine (2.03 mL, 25.1 mmol). The reaction mixture was cooled to 0° C. and a solution of 2-bromopropionyl bromide (2.64 mL, 25.1 mmol) in CH$_2$Cl$_2$ (7 mL) was added dropwise. The reaction mixture was stirred for an additional 30 min. The reaction mixture was diluted in Et$_2$O and washed with water and brine. The organic phase was dried over MgSO$_4$ and concentrated. The crude product was purified by column chromatography (silica gel; EtOAc/Hexane=15:85 gradient to EtOAc/Hexane=20:80) to give (3,5)12G1-PE-TP-G2-(Br)$_4$ (75b) as a colorless oil: 5.79 g (95%).

(3,4,5)12G1-PE-TP-G2-(Br)$_4$ (75c): (3,4,5)12G1-PE-TP-G1-(OH)$_4$ (74c) (2.58 g, 1.45 mmol) was dissolved in dry CH$_2$Cl$_2$ (15 mL) and pyridine (0.7 mL, 8.72 mmol). The reaction mixture was cooled to 0° C. and a solution of 2-bromopropionyl bromide (0.91 mL, 8.72 mmol) in CH$_2$Cl$_2$ (30 mL) was added dropwise. The reaction mixture was stirred for an additional 10 min. The reaction mixture was diluted in DCM (100 mL) and washed with water (4×100 mL) and brine (100 mL). The organic phase was dried over MgSO$_4$ and concentrated. The crude product was purified by silica gel flash column chromatography using a gradient elution of DCM to 1% EtOAc/DCM to give (3,4,5)12G1-PE-TPG2-(Br)$_4$ (75c) as a white solid: 3.15 g (95%). Mixture of diastereomers.

(3,4)12G1-PE-TP-G2-(OH)$_8$ (76a): To a solution of (3,4)12G1-PE-TP-G2-(Br)$_4$ (75a) (0.76 g, 0.42 mmol), and 1-thioglycerol (0.21 mL, 2.36 mmol) in CH$_2$Cl$_2$ (1 mL) and MeCN (2 mL) was added Et$_3$N (0.33 mL, 2.36 mmol) dropwise via syringe at 25° C. After the complete conversion determined by MALDI-TOF, the reaction mixture was diluted in DCM (100 mL) and washed with water (3×100 mL) and brine (100 mL). The organic phase was dried over MgSO$_4$ and concentrated. The crude product was purified by silica gel flash column chromatography using a gradient elution of EtOAc up to 10% MeOH/EtOAc to give (3,4)12G1-PE-TP-G2-(OH)$_8$ (76a) as a white solid: 0.36 g (42%). Complex mixture of diastereomers.

(3,5)12G1-PE-TP-G2-(OH)$_8$ (76b): To a solution of (3,5) 12G1-PE-TP-G2-(Br)$_4$ (75b) (1.00 g, 0.51 mmol), and 1-thioglycerol (0.27 g, 2.5 mmol) in CH$_2$Cl$_2$ (2 mL) and CH$_3$CN (5 mL) was added a solution of Et$_3$N (0.25 g, 2.5 mmol) in CH$_3$CN (5 mL) dropwise via syringe at 25° C. After the complete conversion determined by MALDI-TOF and TLC, the Et$_3$NHBr salts were precipitated in Et$_2$O and the reaction mixture was filtered and concentrated. The crude product was purified by column chromatography (silica gel, MeOH/CH$_2$Cl$_2$=10:90) to give (3,5)12G1-PE-TP-G2-(OH)$_8$ (76b) as a pale yellow solid: 0.71 g (67%).

(3,4,5)12G1-PE-TP-G2-(OH)$_8$ (76c): To a solution of (3,4,5)12G1-PE-TP-G2-(Br)$_4$ (75c) (0.78 g, 0.34 mmol), and 1-thioglycerol (0.12 mL, 1.48 mmol) in CH$_2$Cl$_2$ (2 mL) and MeCN (5 mL) was added Et$_3$N (0.21 mL, 1.48 mmol) dropwise via syringe at 25° C. After the complete conversion determined by MALDI-TOF, the reaction mixture was diluted in EtOAc (150 mL) and washed with water (100 mL), 0.5 N HCl (2×50 mL), water (100 mL) and brine (100 mL). The organic phase was dried over MgSO$_4$ and concentrated. The crude product was purified by silica gel flash column chromatography using a gradient elution of EtOAc up to 3% MeOH/EtOAc to give (3,4,5)12G1-PE-TP-G2-(OH)$_8$ (76c) as a white solid: 0.55 g (67%). Complex mixture of diastereomers.

(3,4)12G1-PE-TP-G3-(Br)$_8$ (77a): (3,4)12G1-PE-TP-G2-(OH)$_8$ (76a) (0.24 g, 0.12 mmol) was dissolved in dry CH$_2$Cl$_2$ (10 mL) and pyridine (0.11 mL, 1.4 mmol). The reaction mixture was cooled to 0° C. and a solution of 2-bromopropionyl bromide (0.15 mL, 1.4 mmol) in CH$_2$Cl$_2$ (20 mL) was added dropwise. The reaction mixture was stirred for an additional 10 min. The reaction mixture was diluted in DCM (100 mL) and washed with water (4×100 mL) and brine (100 mL). The organic phase was dried over MgSO$_4$ and concentrated. The crude product was purified by silica gel flash column chromatography using a gradient elution of DCM up to 10% EtOAc/DCM to give (3,4)12G1-PETP-G3-(Br)$_8$ (77a) as a white solid: 0.29 g (77%). Complex mixture of diastereomers.

(3,5)12G1-PE-TP-G3-(Br)$_8$ (77b): (3,5)12G1-PE-TP-G2-(OH)$_8$ (76b) (3.35 g, 1.63 mmol) was dissolved in dry CH$_2$Cl$_2$ (15 mL) and pyridine (2.14 mL, 26.1 mmol). The reaction mixture was cooled to 0° C. and a solution of 2-bromopropionyl bromide (2.73 mL, 26.1 mmol) in CH$_2$Cl$_2$ (5 mL) was added dropwise. The reaction mixture was stirred for an additional 30 min. The reaction mixture was diluted in Et$_2$O and washed with water and brine. The organic phase was dried over MgSO$_4$ and concentrated. The crude product was purified by column chromatography (silica gel; EtOAc/Hexane=10:80 gradient to EtOAc/Hexane=20:80) to give (3,5)12G1-PE-TP-G3-(Br)$_8$ (77b) as a colorless oil: 4.65 g (91%).

(3,4,5)12G1-PE-TP-G3-(Br)$_8$ (77c): (3,4,5)12G1-PE-TP-G2-(OH)$_8$ (76c) (1.21 g, 0.51 mmol) was dissolved in dry CH$_2$Cl$_2$ (10 mL) and pyridine (0.24 mL, 6.03 mmol). The reaction mixture was cooled to 0° C. and a solution of 2-bromopropionyl bromide (0.63 mL, 6.03 mmol) in CH$_2$Cl$_2$ (30 mL) was added dropwise. The reaction mixture was stirred for an additional 10 min. The reaction mixture was diluted in DCM (100 mL) and washed with water (4×100 mL) and brine (100 mL). The organic phase was dried over MgSO$_4$ and concentrated. The crude product was by silica gel flash column chromatography using a gradient elution of DCM to up to 6% EtOAc/DCM to give (3,4,5)12G1-PE-TPG3-(Br)$_8$ (77c) as a white solid: 1.63 g (91%). Mixture of diastereomers.

(3,4)12G1-PE-TP-G3-(OH)$_{16}$ (78a): To a solution of (3,4) 12G1-PE-TP-G3-(Br)$_8$ (77a) (0.29 g, 0.09 mmol), and 1-thioglycerol (0.10 mL, 1.15 mmol) in CH$_2$Cl$_2$ (1 mL) and MeCN (5 mL) was added Et$_3$N (0.13 mL, 0.9 mmol) dropwise via syringe at 25° C. After the complete conversion determined by MALDI-TOF, the reaction mixture was diluted in EtOAc (100 mL) and washed with water (50 mL). The organic phase was dried over MgSO$_4$ and concentrated. The crude product was purified by silica gel flash column chromatography using a gradient elution of EtOAc to 10% MeOH/EtOAc to give (3,4)12G1-PE-TP-G3-(OH)$_{16}$ (78a) as an off-white solid: 0.12 g (38%). Complex mixture of diastereomers.

(3,5)12G1-PE-TP-G3-(OH)$_{16}$ (78b): To a solution of (3,5) 12G1-PE-TP-G3-(Br)$_8$ (77b) (1.88 g, 0.60 mmol), and 1-thioglycerol (0.57 g, 5.3 mmol) in CH$_2$Cl$_2$ (5 mL) and CH$_3$CN (5 mL) was added a solution of Et$_3$N (0.53 g, 5.3 mmol) in CH$_3$CN (2 mL) dropwise via syringe at 25° C. After the complete conversion determined by MALDI-TOF and TLC, the Et$_3$NHBr salts were precipitated in Et$_2$O and the reaction mixture was filtered and concentrated. The crude product was purified by column chromatography (silica gel, MeOH/CH$_2$Cl$_2$=10:90 gradient to MeOH/CH$_2$Cl$_2$=15:85) to give (3,5)12G1-PE-TP-G3-(OH)$_{16}$ (78b) as a pale yellow solid: 0.93 g (46%).

(3,4,5)12G1-PE-TP-G3-(OH)$_{16}$ (78c): To a solution of (3,4,5)12G1-PE-TP-G3-(Br)$_8$ (77c) (0.35 g, 0.1 mmol), and 1-thioglycerol (0.10 mL, 1.15 mmol) in CH$_2$Cl$_2$ (1 mL) and MeCN (5 mL) was added Et$_3$N (0.14 mL, 1 mmol) dropwise via syringe at 25° C. After the complete conversion determined by MALDI-TOF, the reaction mixture was diluted in EtOAc (100 mL) and washed with water (50 mL). The organic phase was dried over MgSO$_4$ and concentrated. The crude product was purified by silica gel flash column chromatography using a gradient elution of EtOAc to 10% MeOH/EtOAc to give (3,4,5)12G1-PE-TP-G3-(OH)$_{16}$ (78c) as an off-white solid: 0.34 g (90%). Complex mixture of diastereomers.

(3,5)12G1-CH$_2$OH (80b): LiAlH$_4$ (0.56 g, 14.9 mmol) was added to THF (125 mL) at 0° C. The suspension was stirred for 5 min after which 3,5-dodecanol methylbenzoate (79b) (5 g, 9.9 mmol) dissolved in THF (20 mL) was added dropwise. After 1 hour, the reaction was complete by TLC. The reaction mixture was carefully poured into a 4 L beaker and slowly diluted with THF (100 mL, not distilled). The slurry was treated with water (0.6 mL), 15% NaOH (0.6 mL) and then water (1.8 mL) and let to stir overnight to quench. The suspension was filtered through celite, dried over MgSO$_4$, filtered and the solvent evaporated. The residue was purified by silica gel flash column chromatography using a gradient elution of hexanes up to 20% EtOAc, and the sample was dried under high vacuum overnight to afford a white solid: 4.72 g (100% yield).

(3,5)12G1-CHO (81): Dess-Martin periodinane (Dess, J. Org. Chem. 48, 4155-4156 (1983)) (C$_{13}$H$_{13}$IO$_8$) (1.16 g, 2.73 mmol) was dissolved in DCM (17 mL) followed by (3,5)12G1-CH$_2$OH (80b) (1 g, 2.1 mmol). After 1 hr, the reaction was complete by TLC. The reaction mixture was diluted with diethyl ether (50 mL), then treated with 1.3 N NaOH (20 mL) and stirred for 5 min. The organic layer was washed with 1.3 N HCl (20 mL) and water (25 mL), and the solvent was evaporated. The residue was purified using column chromatography on silica gel with a mobile phase of DCM, and the sample was dried under high vacuum overnight to afford a white solid: 0.86 g (86% yield).

(3,4,5)-3EO-G1-(OCH$_3$)$_3$—CH$_2$OH (82): LiAlH$_4$ (0.32 g, 8.4 mmol) was added to THF (60 mL) at 0° C. The suspension was stirred for 5 min after which (3,4,5)-3EO-G1-(OCH$_3$)$_3$—CO$_2$CH$_3$ (13c) (3.5 g, 5.6 mmol) dissolved in THF (20 mL) was added dropwise. After 20 min, the reaction was complete as determined by TLC. The reaction mixture was carefully poured into a 4 L beaker and slowly diluted with THF (100 mL, not distilled). The slurry was treated with water (0.3 mL), 15% NaOH (0.3 mL) and then water (1 mL) and let to stir overnight to quench. The suspension was filtered through celite, dried over MgSO$_4$, filtered and the solvent evaporated to yield a clear colorless oil that was used without further purification: 2.60 g (78% yield).

(3,4,5)-3EO-G1-(OCH$_3$)$_3$—CHO (83): Dess-Martin periodinane (C$_{13}$H$_{13}$IO$_8$) (0.53 g, 0.89 mmol) was dissolved in DCM (5 mL) followed by (3,4,5)-3EO-G1-(OCH$_3$)$_3$—CH$_2$OH (82) (0.49 g, 1.16 mmol). After 1 hr, the reaction was complete by TLC. The reaction mixture was diluted with diethyl ether (50 mL), then treated with 1.3 N NaOH (20 mL) and stirred for 5 min. The organic layer was washed with 1.3 N HCl (20 mL) and water (25 mL). The aqueous layer was extracted with EtOAc (3×50 mL), which was then combined with the diethyl ether portion. The sample was dried over MgSO$_4$, filtered and the solvent was evaporated to yield a clear colorless oil. The compound was used without further purification: 2.06 g (80% yield).

(3,5)12G1-dAc—(OH)$_2$ (84): Pentaerythritol (3 g, 22 mmol) and TsOH (0.05 g, 0.29 mmol) were added to benzene (20 mL) and DMF (30 mL) and the suspension was refluxed until fully dissolved. (3,5)12G1-CHO (81) (0.5 g, 1.05 mmol) was dissolved in benzene (5 mL) and added dropwise. After 1 h, the reaction was complete by TLC. The reaction mixture was cooled to rt and poured into water (50 mL). The aqueous layer was extracted with DCM (3×50 mL). The organic layer was then washed with water (4×100 mL) and brine (100 mL). The sample was then dried over MgSO$_4$, filtered and the solvent evaporated. The residue was purified by flash column chromatography on silica gel using a gradient of hexanes to EtOAc, and the sample was dried under high vacuum overnight to afford a white solid: 0.60 g (96% yield).

(3,5)12G1-dAc-(3,4,5)-3EO-G1-(OCH$_3$)$_3$ (85): (3,4,5)-3EO-G1-(OCH$_3$)$_3$—CHO (83) (0.33 g, 0.557 mmol), (3,5)12G1-dAc—(OH)$_2$ (84) (0.33 g, 0.557 mmol) and TsOH (0.02 g, 0.12 mmol) were dissolved in benzene (10 mL). The reaction mixture was refluxed for 30 min after which the reaction was complete by TLC. The reaction mixture cooled to rt and was poured into water (50 mL) and neutralized with K$_2$CO$_3$. The aqueous layer was removed and the organic layer was washed with brine and dried over MgSO$_4$. The sample was filtered and The solvent evaporated. The residue was purified by flash column chromatography on silica gel using a gradient of ethyl acetate to methanol up to 10% to afford a colorless oil: 0.15 g (23% yield).

tris12-PE-BMPA-G1-(benzylidene)$_1$ (87): This compound was synthesized by the same procedure described for the synthesis of (3,4)12G1-PE-BMPA-G3-(benzylidene)$_8$ (7a). From tri-O-dodecyl pentaerythritol (86) (5.00 g, 7.80 mmol), benzylidene-2,2 bis(oxymethyl)propionic anhydride (4.32 g, 10.14 mmol), DMAP (0.31 g, 2.54 mmol), pyridine (5 mL), and CH$_2$Cl$_2$ (15 mL), 5.30 g (82%) of tris12-PE-BMPA-G1-(benzylidene)$_1$ (87) was obtained as a white solid.

tris12-PE-BMPA-G1-(OH)$_2$ (88): This compound was synthesized by the same procedure described for the synthesis of (3,4)12G1-PE-BMPA-G3-(OH)$_{16}$ (8a). From tris12-PE-BMPA-G1-(benzylidene)$_1$ (87) (3.00 g, 3.55 mmol), Pd/C (0.30 g), CH$_2$Cl$_2$ (20 mL), and MeOH (20 mL) 2.09 g (78%) of tris12-PE-BMPA-G1-(OH)$_2$ (88) was obtained as a white solid after column chromatography (EtOAc/hexane=15:85).

tris12-PE-BMPA-G2-(benzylidene)$_2$ (89): This compound was synthesized by the same procedure described for the synthesis of tris12-PE-BMPA-G1-(benzylidene)$_1$ (87). From tris12-PE-BMPA-G1-(OH)$_2$ (88) (2.00 g, 2.64 mmol), benzylidene-2,2-bis(oxymethyl)propionic anhydride (2.93 g, 6.87 mmol), DMAP (0.21 g, 1.72 mmol), pyridine (3 mL), and CH$_2$Cl$_2$ (9 mL), 1.65 g (54%) of tris12-PE-BMPA-G2-(benzylidene)$_2$ (89) was obtained as a white solid after column chromatography (EtOAc/hexane=10:90) and precipitation in MeOH.

tris12-PE-BMPA-G2-(OH)$_4$ (90): This compound was synthesized by the same procedure described for the synthesis of tris12-PE-BMPA-G1-(OH)$_2$ (88). From tris12-PE-BMPA-G2-(benzylidene)$_2$ (89) (1.60 g, 1.37 mmol), Pd/C (0.16 g), CH$_2$Cl$_2$ (20 mL), and MeOH (10 mL). 1.35 g (99%) of tris12-PE-BMPA-G2-(OH)$_4$ (90) was obtained as a white solid.

tris12-PE-BMPA-G3-(benzylidene)$_4$ (91): This compound was synthesized by the same procedure described for the synthesis of tris12-PE-BMPA-G1-(benzylidene)$_1$ (87). From tris12-PE-BMPA-G2-(OH)$_4$ (90) (0.95 g, 0.96 mmol), benzylidene-2,2 bis(oxymethyl)propionic anhydride (2.13 g, 4.99 mmol), DMAP (0.15 g, 1.25 mmol), pyridine (5 mL), and CH$_2$Cl$_2$ (20 mL), 1.50 g (87%) of tris12-PE-BMPA-G3-(benzylidene)$_4$ (91) was obtained as a white solid after column chromatography (EtOAc/hexane=25:75) and recrystallization in MeOH.

tris12-PE-BMPA-G3-(OH)$_8$ (92): This compound was synthesized by the same procedure described for the synthesis of tris12-PE-BMPA-G1-(OH)$_2$ (88). From tris12-PE-BMPA-G3-(benzylidene)$_4$ (91) (1.30 g, 0.72 mmol), Pd/C (0.13 g), CH$_2$Cl$_2$ (20 mL), and MeOH (10 mL). 0.87 g (83%) of tris12-PE-BMPA-G3-(OH)$_8$ (92) was obtained as a white solid.

(3,4)12G1-BnE-(3,4)-3EO-G1-(OCH$_3$)$_2$ (93a): (3,4)12G1-CH$_2$OH (80a) (0.41 g, 0.85 mmol), (3,4)-3EO-G1-(OCH$_3$)$_2$—CO$_2$H (14a) (0.38 g, 0.85 mmol) and DPTS (0.13 g, 0.43 mmol) were dissolved in anhydrous DCM (7 mL). DCC (0.23 g, 1.1 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by flash column chromatography on silica gel using a gradient of ethyl acetate to methanol up to 5% to afford a colorless oil: 0.50 g (65% yield).

(3,4)12G1-BnE-(3,5)-3EO-G1-(OCH$_3$)$_2$ (93b): (3,4)12G1-CH$_2$OH (80a) (0.53 g, 1.12 mmol), (3,5)-3EO-G1-(OCH$_3$)$_2$—CO$_2$H (14b) (0.5 g, 1.12 mmol) and DPTS (0.16 g, 0.56 mmol) were dissolved in anhydrous DCM (7 mL). DCC (0.3 g, 1.46 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by flash column chromatography on silica gel using a gradient of ethyl acetate to methanol up to 5% to afford a colorless oil: 0.83 g (82% yield).

(3,4)12G1-BnE-(3,4,5)-3EO-G1-(OCH$_3$)$_3$ (93c): (3,4) 12G1-CH$_2$OH (80a) (0.59 g, 1.23 mmol), (3,4,5)-3EO-G1-(OCH$_3$)$_2$—CO$_2$H (14c) (0.75 g, 1.23 mmol) and DPTS (0.18 g, 0.62 mmol) were dissolved in anhydrous DCM (7 mL). DCC (0.33 g, 1.6 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by flash column chromatography on silica gel using a gradient of ethyl acetate to methanol up to 5% to afford a colorless oil: 0.70 g (53% yield).

(3,5)12G1-BnE-(3,4)-3EO-G1-(OCH$_3$)$_2$ (93d): (3,5) 12G1-CH$_2$OH (80b) (0.5 g, 1.05 mmol), (3,4)-3EO-G1-(OCH$_3$)$_2$—CO$_2$H (14a) (0.47 g, 1.05 mmol) and DPTS (0.15 g, 0.525 mmol) were dissolved in anhydrous DCM (7 mL). DCC (0.28 g, 1.37 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by flash column chromatography on silica gel using a gradient of ethyl acetate to methanol up to 5% to afford a colorless oil: 0.74 g (78% yield).

(3,5)12G1-BnE-(3,5)-3EO-G1-(OCH$_3$)$_2$ (93e): (3,5) 12G1-CH$_2$OH (80b) (0.53 g, 1.12 mmol), (3,5)-3EO-G1-(OCH$_3$)$_2$—CO$_2$H (14b) (0.5 g, 1.12 mmol) and DPTS (0.16 g, 0.56 mmol) were dissolved in anhydrous DCM (7 mL). DCC (0.3 g, 1.46 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by flash column chromatography on silica gel using a gradient of ethyl acetate to methanol up to 5% to afford a colorless oil: 1.01 g (99% yield).

(3,5)12G1-BnE-(3,4,5)-3EO-G1-(OCH$_3$)$_3$ (93f): (3,5) 12G1-CH$_2$OH (80b) (0.48 g, 1.01 mmol), (3,4,5)-3EO-G1-(OCH$_3$)$_2$—CO$_2$H (14c) (0.6 g, 0.99 mmol) and DPTS (0.15 g, 0.525 mmol) were dissolved in anhydrous DCM (7 mL). DCC (0.281 g, 1.37 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by flash column chromatography on silica gel using a gradient of ethyl acetate to methanol up to 5% to afford a colorless oil: 0.72 g (68% yield).

(3,4,5)12G1-BnE-(3,4)-3EO-G1-(OCH$_3$)$_2$ (93g): (3,4,5) 12G1-CH$_2$OH (80c) (0.86 g, 1.30 mmol), (3,4)-3EO-G1-(OCH$_3$)$_2$—CO$_2$H (14a) (0.58 g, 1.30 mmol) and DPTS (0.16 g, 0.56 mmol) were dissolved in anhydrous DCM (7 mL). DCC (0.3 g, 1.46 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by flash column chromatography on silica gel using a gradient of ethyl acetate to methanol up to 5% to afford a colorless oil: 1.06 g (75% yield).

(3,4,5)12G1-BnE-(3,5)-3EO-G1-(OCH$_3$)$_2$ (93h): (3,4,5) 12G1-CH$_2$OH (80c) (0.74 g, 1.11 mmol), (3,5)-3EO-G1-(OCH$_3$)$_2$—CO$_2$H (14b) (0.5 g, 1.11 mmol) and DPTS (0.16 g, 0.56 mmol) were dissolved in anhydrous DCM (7 mL). DCC (0.3 g, 1.44 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by flash column chromatography on silica gel using a gradient of ethyl acetate to methanol up to 5% to afford a colorless oil: 0.99 g (91% yield).

(3,4,5)12G1-BnE-(3,4,5)-3EO-G1-(OCH$_3$)$_3$ (93i): (3,4,5) 12G1-CH$_2$OH (80c) (0.54 g, 0.82 mmol), (3,4,5)-3EO-G1-(OCH$_3$)$_2$—CO$_2$H (14c) (0.5 g, 0.82 mmol) and DPTS (0.12 g, 0.41 mmol) were dissolved in anhydrous DCM (7 mL). DCC (0.22 g, 1.07 mmol) dissolved in anhydrous DCM (3 mL) was added, and the reaction mixture was stirred for 24 h at rt. After the reaction was complete, the mixture was diluted with hexanes, filtered through celite and rinsed with hexanes. The solvent was evaporated under vacuum and the residue was purified by flash column chromatography on silica gel using a gradient of ethyl acetate to methanol up to 5% to afford a colorless oil: 0.78 g (88% yield).

1,2,3-tris(butyloxy)-5-nitrobenzene (94a): To the solution of 1,2,3-tributyloxybenzene (102a) (10.0 g, 0.340 mol) and NaNO$_2$ (0.58 g, 0.068 mol) in a mixture of CH$_2$Cl$_2$/H$_2$O (50 mL/3 mL) stirred at 25° C. under Ar, concentrated HNO$_3$ was added dropwise. After 3 h water was added and the crude product was extracted into CH$_2$Cl$_2$. Organic layer was washed with water and dries over Na$_2$S$_2$O$_4$. The solvent was evaporated and the crude product was purified on silica gel column with hexane: CH$_2$Cl$_2$ (4:1) as an eluent yielding a pale yellow oil (6.05 g, 52% yield). TLC (SiO$_2$, hexanes: CH$_2$Cl$_2$ 1:1) Rf=0.37.

(3,4,5)12G1-NO$_2$ (94b): Method A (Percec, Macromolecules 29, 1464-1472 (1996); Percec, J. Am. Chem. Soc. 128, 16365-16372, (2006); and Percec, Chem. Eur. J., 1070-1083 (1999)): To the solution of 1,2,3-tridodecyloxybenzene (21.61 g, 34.2 mmol) and NaNO$_2$ (0.48 g, 6.9 mmol) in a mixture of CH$_2$Cl$_2$/H$_2$O (50 mL/2.5 mL) stirred at 25° C. under Ar, concentrated HNO$_3$ was added dropwise. After 3 h water was added and the crude product was extracted into CH$_2$Cl$_2$. The organic layer was washed with water and dries over Na$_2$S$_2$O$_4$. The solvent was evaporated and the crude product was purified on silica gel column with hexane: CH$_2$Cl$_2$ (4:1) as an eluent yielding a pale yellow oil (16.01 g, 69% yield). Method B (Das, Org. Lett. 4, 3055-3058 (2002)): AIBN (0.05 g, 0.30 mmol) was added in a solution of (3,4,5)12G1-CO$_2$H (1c) (9.00 g, 13.3 mmol) and HNO$_3$ (1.78 mL, 40.0 mmol) in CH$_3$CN (100 mL). The reaction mixture was stirred at 50° C. for 36 h. After the reaction was complete, iced-cold water was added and the mixture was extracted with Et$_2$O, washed with water, brine, and dried over MgSO$_4$. The combined organic phase was concentrated, passed through basic Al$_2$O$_3$ using CH$_2$Cl$_2$ as eluent, and precipitated in MeOH to give (3,4,5)12G1-NO$_2$ (94b) as a pale yellow solid: 6.08 g (67%).

1,2,3-Tris(butyloxy)benzeneamine (95a): A mixture of 1,2,3-tris(butyloxy)-5-nitrobenzene (94a) (5.70 g, 16.8 mmol), hydrazine-monohydrate (5 eq., 4.21 g, 84.0 mmol) and graphite (11.10 g, 924.0 mmol) in ethanol (150 mL) was stirred at 80° C. in the atmosphere of Ar for 20 h. The reaction mixture was cooled to 25° C. The graphite was filtered off and washed with CH$_2$Cl$_2$ to dissolve the product that was partially precipitated at 25° C. The solvent was evaporated and the amine 10a was recrystallized from EtOH yielding a white solid (3.80 g, 73%). TLC (SiO$_2$, hexanes: CH$_2$Cl$_2$ 1:1) Rf=0.06.

(3,4,5)12-NH$_2$ (95b): A mixture of (3,4,5)12G1-NO$_2$ (94b) (3.00 g, 4.4 mmol), hydrazine-monohydrate (5 eq., 1.10 g, 22.0 mmol) and graphite (2.91 g, 242.0 mmol) in ethanol (80 mL) was stirred at 80° C. in the atmosphere of Ar for 20 h. The reaction mixture was cooled to 25° C. The graphite was filtered off and washed with CH$_2$Cl$_2$ to dissolve the product that was partially precipitated at 25° C. The solvent was evaporated and the amine (3,4,5)12-NH$_2$ (95b) was recrystallized from EtOH yielding white solid (4.51 g, 88%). TLC (SiO2, hexanes: CH$_2$Cl$_2$ 1:1) Rf=0.09.

(3,4,5)12G1-PhA-(3,4,5)-3EO-G1-(OCH$_3$)$_3$ (96): (3,4,5) 12-NH$_2$ (95b) (1.62 g, 2.50 mmol), (3,4,5)-3EO-G1-(OCH$_3$)$_3$—CO$_2$H (14c) (1.52 g, 2.50 mmol), and DPTS (0.37 g, 1.25 mmol) were dissolved in anhydrous CH$_2$Cl$_2$ (7 mL). DCC (1.55 g, 7.50 mmol) dissolved in anhydrous CH$_2$Cl$_2$ (3 mL) was added, and the reaction mixture was stirred for 12 h at room temperature. After the reaction was complete, the mixture was diluted, filtered, and rinsed with CH$_2$Cl$_2$. The solvent was evaporated under vacuum and the residue was purified by column chromatography (silica gel; MeOH/EtOAc=3:97) and precipitated in MeOH to give (3,4,5)12G1-PhA-(3,4,5)-3EO-G1-(OCH$_3$)$_3$ (96) as a white solid: 1.51 g (49%).

(3-Chloropropyl)-carbamic acid tert-butyl ester (98): 3-Chloropropylammonium chloride (97) (10 g, 76.80 mmol) was added to 40 mL aqueous solution of 2N NaOH. The mixture was stirred at 23° C. until a clear solution was obtained. The resulting solution was cooled to 0° C. and di-t-butyl dicarbonate (Boc anhydride, 16.74 g, 76.78 mmol) and 4N NaOH (10 mL) were added. The reaction mixture was allowed to warm up and stirred at 23° C. for 14 h. The mixture was extracted with diethyl ether (2×50 mL). The combined organic phase was washed twice with water, dried over MgSO$_4$ and the solvent was removed under reduced pressure. The resulting crude product was purified by short column chromatography (SiO2, CH$_2$Cl$_2$) to produce the pure product as colorless oil in 87% (12.90 g) yield.

3,4,5-Tris-(3-t-butoxycarbonylaminopropoxy)benzoic acid methyl ester (99): In a round-bottom flask equipped with an addition funnel and a magnetic stirrer, 15 g (108.7 mmol) of K$_2$CO$_3$ and 120 mL of dry DMF were placed and purged with nitrogen for 0.5 h at 60° C. 3,4,5-Trihydroxymethylbenzoate (3.4 g, 18.47 mmol) was added and the solution was purged with nitrogen for additional 0.5 h. (3-Chloropropyl)-carbamic acid tert-butyl ester (98) (10.70 g, 55.30 mol) was added and the reaction mixture was stirred for 15 h at the same temperature. The reaction mixture was cooled to 23° C. and poured into 100 mL of ice-water. The resulting precipitate was filtered and dried. The crude product was purified by column chromatography (SiO$_2$, CH$_2$Cl$_2$: acetone 10:1). The product was recrystallized from EtOAc: hexane to produce white crystalline material (10.2 g, 90%).

3,4,5-Tris-(3-t-butoxycarbonylamino-propoxy)benzoic acid (100): To 180 mL of Tesser Base (made from dioxane: methanol:4M NaOH 14:5:2 V/V/V) was added to 3,4,5-Tris-(3-t-butoxycarbonylaminopropoxy)benzoic acid methyl ester (99) (9.70 g, 15.98 mmol) and the mixture was stirred at 23° C. for 45 h. To the reaction mixture was added a solution of citric acid in dioxane:MeOH (2:1) until pH=5. The solvents were removed under reduced pressure and the resulting residue was subject to column chromatography using CH$_2$Cl$_2$:acetone (10:1). Subsequent recrystallization from EtOAc produced the pure product as white solid (9.20 g, 97%).

1,2,3-Tributyloxybenzene (102a): To the degassed solution of 1,2,3-trihydroxybenzene (101) (5.00 g, 0.040 mol) and 1-bromobutane (15.4 mL, 19.53 g, 0.143 mol) in DMF (200 mL) potassium carbonate (49.25 g, 0.356 mol) was added and the mixture was stirred under Ar at 90° C. for 24 h. The reaction was cooled to 25° C. and poured to cola acidic (acidified by HCl) water. The product was extracted into CH$_2$Cl$_2$ and the organic solution was washed with water. The organic layer was separated dried over Na$_2$SO$_4$. The solvent was evaporated and the product was purified on silica gel column with hexane: CH$_2$Cl$_2$ (4:1) as an eluent yielding a pale yellow oil (10.5 g, 90% yield). TLC (SiO$_2$, hexanes: CH$_2$Cl$_2$ 1:1) Rf=0.49.

1,2,3-Tridodecyloxybenzene (102b): To the degassed solution of 1,2,3-trihydroxybenzene (101) (8.20 g, 0.065 mol) and 1-bromododecane (56.6 mL, 58.33 g, 0.234 mol) in DMF (250 mL) potassium carbonate (g, mmol) was added and the mixture was stirred under Ar at 90° C. for 24 h. The reaction was cooled to 25° C. and poured to cola acidic (acidified by HCl) water. The product was extracted into CH$_2$Cl$_2$ and the organic solution was washed with water. The organic layer was separated dried over Na$_2$SO$_4$. The solvent was evaporated and the product was purified on silica gel column with hexane: CH$_2$Cl$_2$ (4:1) as an eluent yielding a pale yellow oil (30.79 g, 75% yield). TLC (SiO$_2$, hexanes: CH$_2$Cl$_2$ 1:1) Rf=0.61.

(3,4,5)4G1-PhA-(3,4,5)-3-G1-(NHBoc)$_3$ (103a): To the mixture of 1,2,3-Tris(butyloxy)benzeneamine (95a) (0.70 g, 2.26 mmol), 3,4,5-Tris-(3-tert-butoxycarbonylamino-propoxy)benzoic acid (100) (1.45 g, 2.26 mmol) and 2-chloro-4,6-dimethoxy-1,3,5-triazine (CDMT, 1.2 eq., 0.47 g, 2.71 mol) in dry THF (40 mL) in the atmosphere of Ar, 4-methylmorpholine (NMM, 2.5 eq., 0.57 g, 5.65 mmol, 0.62 mL) was added and the mixture was stirred in the atmosphere of Ar for 12 h at 25° C. The precipitation formed at the beginning of the reaction was filtered off and the solvent was evaporated. The product was purified on the silica gel column using CH$_2$Cl$_2$ and CH$_2$Cl$_2$:EtOAc (9:1), followed by recrystallization from acetone yielding a white solid (1.18 g, 49%). TLC (SiO$_2$, hexanes: CH$_2$Cl$_2$ 1:1) Rf=0.41.

(3,4,5)12G1-PhA-(3,4,5)-3-G1-(NHBoc)$_3$ (103b): To the mixture of (3,4,5)12-NH$_2$ (95b) (0.78 g, 1.21 mmol), 3,4,5-Tris-(3-tert-butoxycarbonylamino-propoxy)benzoic acid (100) (0.78 g, 1.21 mmol) and 2-chloro-4,6-dimethoxy-1,3,5-triazine (CDMT, 1.2 eq., 0.25 g, 1.45 mol) in dry THF (40 mL) in the atmosphere of Ar, 4-methylmorpholine (NMM, 2.5 eq., 0.31 g, 3.03 mmol, 0.34 mL) was added and the mixture was stirred in the atmosphere of Ar for 12 h at 25° C. The precipitation formed at the beginning of the reaction was filtered off and the solvent was evaporated. The product was purified on the silica gel column using CH$_2$Cl$_2$ and CH$_2$Cl$_2$:EtOAc (9:1), followed by recrystallization from acetone yielding white solid (1.08 g, 70%). TLC (SiO$_2$, hexanes: CH$_2$Cl$_2$ 1:1) Rf=0.45.

(3,4,5)4G1-PhA-(3,4,5)-3-G1-(NH$_3$Cl)$_3$ (104a): To the solution of (3,4,5)4G1-PhA-(3,4,5)-3-G1-(NHBoc)$_3$ (103a) (0.60 g, 0.643 mmol) in dry CH$_2$Cl$_2$ (20 mL) in the atmosphere of Ar, 2N HCl in Et$_2$O (4 mL) was added. The reaction was stirred at 25° C. in Ar atmosphere and its progress was followed by $^1$H NMR. If necessary the additional amounts of HCl in Et$_2$O was added until the complete disappearance of BOC group in the NMR spectrum. The solvent was evaporated and the crude product was washed with CH$_2$Cl$_2$, filtered and dried to yield yellowish solid (0.47 g, 98%) of poor solubility in common solvents.

(3,4,5)12G1-PhA-(3,4,5) 3-G1-(NH$_3$Cl)$_3$ (104b): To the solution of (3,4,5)12G1-PhA-(3,4,5) 3-G1-(NHBoc)$_3$ (103b) (0.50 g, 0.394 mmol) in dry CH$_2$Cl$_2$ (20 mL) in the atmosphere of Ar, 2 N HCl in Et$_2$O (4 mL) was added. The reaction was stirred at 25° C. in Ar atmosphere and its progress was followed by $^1$H NMR. If necessary the additional amounts of HCl in Et$_2$O was added until the complete disappearance of BOC group in the NMR spectrum. The solvent was evaporated and the crude product was washed with $CH_2Cl_2$, filtered and dried to yield a yellowish solid (0.268 g, 63%) of poor solubility in common solvents.

3,4,5-Tris(dodecyl-1-oxy)benzylazide (106): To a solution of the 3,4,5-tris(dodecyl-1-oxy)benzylchloride (13) (6.20 g, 9.12 mmol) in DMF (90 mL) was added $NaN_3$ (0.90 g, 10.8 mmol) and the mixture was stirred at 25° C. for 9 h. TLC indicated complete conversion. The reaction mixture was poured into 100 mL of water and the resulting precipitate was filtered and dried. Recrystallization of the crude product from acetone produced 6.1 g (96%) of the pure product as white crystals. mp 58° C. Purity (HPLC): 99%+. TLC ($SiO_2$, hexanes:acetone 9:1) Rf=0.9.

3,4,5-Tris(dodecyl-1-oxy)benzylamine (107): To a suspension of $LiAlH_4$ (0.20 g, 5.22 mmol) in dry THF (15 mL) at 0° C. and under Ar atmosphere was added dropwise a solution of 3,4,5-Tris(dodecyl-1-oxy)benzylazide (106) (3.0 g, 4.39 mmol) in 20 mL of THF. After the addition was completed, the reaction mixture was stirred at 25° C. for 3 h. The reaction mixture was quenched by successive addition of 2 mL $H_2O$, 2 mL of 15% NaOH and 2 mL of $H_2O$. The granular salts were filtered and washed with THF. The solvent was fully evaporated and the remaining solid was recrystallized twice from boiling acetone to produce 2.5 g (89%) of white crystals. mp 62° C. Purity (HPLC): 99%+. TLC ($SiO_2$, hexanes/EtOAc 3:1): Rf=0.30.

{3-[2,3-Bis-(3-t-butoxycarbonylaminopropoxy)-5-(3,4,5-tris dodecyloxybenzylcarbamoyl)phenoxy]propyl}carbamic acid tert-butyl ester; (3,4,5)12G1-BnA-(3,4,5) 3-G1-(NH-Boc)$_3$ (108)48,67: To a solution of 2.0 g (3.03 mmol) of 3,4,5-Tris(dodecyl-1-oxy)benzylamine (107), 1.80 g (3.03 mmol) of 3,4,5-Tris-(3-tert-butoxycarbonylamino-propoxy) benzoic acid (100) and 0.63 g (3.58 mmol) of chlorodimethoxytriazine (CDMT) in 30 mL of THF was added 0.76 g (7.58 mmol) of N-methylmorpholine (NMM). The reaction mixture was stirred at 23° C. for 14 h. A colorless precipitate was removed by filtration of the reaction mixture. The filtrate was evaporated until dryness under reduced pressure. The crude product was purified by chromatography in SiO2 using hexane: $CH_2Cl_2$:EtOAc (10:1) as eluent. Recrystallization from boiling acetone produced 0.45 g (52%) of pure waxy product.

(3,4,5)12G1-BnA-(3,4,5)-3-G1-($NH_3Cl$)$_3$ (109): (3,4,5) 12G1-BnA-(3,4,5)-3-G1-(NHBoc)$_3$ (108) (0.5 g) was dissolved in 20 mL of $CH_2Cl_2$. An ethereal solution of HCl (3 mL of 2M of HCl in ether) was added and the reaction mixture and was stirred at 23° C. for 14 h (TLC showed complete conversion). Diethyl ether (20 mL) was added and the salt was filtered, washed with diethetyl ether and dried to give a yellowish solid (0.18 g, 86%) of poor solubility in common organic solvents.

Texas Red-(3,5)12G1-PE-BMPA-G2-(OH)$_8$ (110). To a thoroughly degassed suspension of DMAP (0.5 mg, 2.0.mol) Janus-dendrimer (3,5)12G1-PE-BMPA-G2-(OH)$_g$ (2 mg, 2.3 μmol) in distilled $CH_2Cl_2$ (1 mL), a solution of Texas Red (1 mg, 1.6 μmol) in $CH_2Cl_2$ (2 mL) was slowly added over 10 min. The reaction was allowed to stir at 25° C. under nitrogen for 24 h, after which TLC (10:1 $CH_2Cl_2$:MeOH) showed completion. The reaction was quenched with cold water and extracted with water. The organic layer was washed with saturated $NaHCO_3$, brine, and water (5×'s), dried over $MgSO_4$ and concentrated. The crude product was purified by flash column chromatography (10:1 $CH_2Cl_2$: MeOH). The purple solid 20 was used without further purification. MALDI-TOF for $C_{128}H_{192}N_2NaO_{34}S_2$ m/z calcd: 2389.28 [M+Na+]. found 2389.47.

Texas Red-(3,4,5)12G1-PhA-(3,4,5)$_3$G1-($NH_3^+Cl^-$)$_3$ conjugate (111). To a thoroughly degassed suspension of DMAP (0.5 mg, 2.0 μmol) Janus-dendrimer 104b (2 mg, 1.9 μmol) in distilled DMF (1 mL), a solution of Texas Red (1 mg, 1.6 mol) in DMF (2 mL) was slowly added over 10 min. The reaction was allowed to stir at 25° C. under nitrogen for 24 h, after which TLC (10:1 $CH_2Cl_2$: MeOH) showed completion. The reaction quenched with cold water and extracted with water. The organic layer was washed with saturated $NaHCO_3$, brine, and water (5×'s), dried over $MgSO_4$ and concentrated. The crude product was purified by flash column chromatography (10:1 $CH_2Cl_2$: MeOH). The purple solid was used without further purification.

Preparation of Dendrosomes

Small Unilamellar Dendrosomes (SUD)

A diversity of methods for the preparation of small unilamellar liposomes are available. See, Szoka, Annu. Rev. Biophys. Bioeng. 9, 467-508 (1980); Monnard, in Methods in Enzymology (ed Nejat Duzgunes) 133-151 (Academic Press, 2003); and Bridson, J. Pharm. Pharmacol. 58, 775-785(11) (2006).

Ethanol Injection

Small unilamellar dendrosomes of <200 nm size were obtained by fast injection of 100 μL of ethanol (THF, acetone, dioxane, acetonitrile or DMSO for the solvent dependence studies) solution containing 10 mg of Janus-dendrimer dissolved in 1 mL of solvent into various volumes of milippore water (0.5 mL-5 mL) giving final Janus-dendrimer concentrations of 0.1-2 mg/mL. Dendrosomes obtained via injection method were used without further manipulation to study the influence of concentration, solvent, temperature and time on size and polydispersity by dynamic light scattering (DLS) as well as for the characterization of dendrosome morphologies via cryogenic transmission electron microscopy (cryo-TEM).

Film Hydration

Small unilamellar dendrosomes were obtained also by film hydration (Huang, Biochemistry 8, 344-352 (1969)). This procedure was used for doxorubicin and calcein release studies as well HUVECs cell work. The Janus-dendrimer was deposited as a film, either at the bottom of a 10 mL round bottom flask by dissolving 2 mg of Janus-dendrimer in $CH_2Cl_2$, THF or diethyl ether followed by slow removal of the solvent under nitrogen and further drying for 12 h under vacuum, or deposited on 1 cm$^2$ roughened Teflon® surface (200 μL of 10 mg/mL Janus-dendrimer solution in $CH_2Cl_2$ covering the entire Teflon surface). The Teflon was carefully placed into a 5 dram screw top vial and dried for 12 h under vacuum. Films were hydrated with 2 mL of Millipore water or buffered solution (PBS or citrate) of pH=7.2 for 7 h at 50-60° C. followed by sonication for 30 min (sonic bath Bransom, Model 3510). Three to five freeze-thaw cycles were performed to promote unilamellar structures. Dendrosomes were further extruded 25 times through 100 nm polycarbonate membrane and used immediately for the release study or cell work.

Large Unilamellar Dendrosomes (LUD)

Film Hydration

Large unilamellar dendrosomes (Deamer, Biochim. Biophys. Acta, Biomembr. 443, 629-634 (1976)) were obtained via film hydration by placing 200 μL of denrimer solution (10 mg/mL Janus-dendrimer solution in methylene chloride, THF or diethyl ether) in a round bottom flask followed by slow solvent removal under reduced pressure ensuring an even distribution of material at the bottom of the flask was obtained. The thin film was subsequently placed under vacuum for 12 h. Addition of 2 mL of aqueous solution (ultrapure water or buffer) followed by hydration and sonication for 60 min yielded dendrosomes whose size and size distribution was determined by DLS.

Giant Unilamellar Dendrosomes (GUD)
Film Hydration

Giant unilamellar dendrosomes (Lasic, J. Am. Chem. Soc. 110, 970-971 (1988)) were prepared by film hydration and were used for visualization by differential interfering contrast microscopy (DIC) and bright field microscopy. Dendrosomes encapsulating hydrophilic or hydrophobic dyes visualized by fluorescence microscopy were obtained by the same method of film hydration with the exception that the hydrophobic dye was dissolved into the $CH_2Cl_2$ Janus-dendrimer solution while the hydrophilic dye was dissolved in the aqueous solution used for hydration. An aliquot of 200 µL of a 10 mg/mL Janus-dendrimer solution in methylene chloride, THF, or diethyl ether was uniformly deposited on the surface of a roughened Teflon plate, placed in a vial and followed by evaporation of the solvent for 12 h. Addition of aqueous solution, and subsequent hydration at 60° C. for ~12 h, (unless otherwise indicated), led to the formation of giant dendrosomes. The sample was then mixed using a vortex mixer for 5 s. In the formation of giant unilamellar dendrosomes no sonication was applied.

Characterization of Dendrosomes

The dendrosome wall was visualized by fluorescence microscopy using Nile red which has a strong emission at 525 nm when is present in a lipid-rich environment when excited at 485 nm. Janus-dendrimer, 10 mg/mL and 0.1 mg/mL Nile Red solution were dissolved in $CH_2Cl_2$, THF, or diethyl ether. An aliquot of 200 µL solution was evenly deposited on the surface of a 1 cm$^2$ roughened Teflon plate and placed in a vial followed by evaporation of the solvent for 12 h. Addition of 2 mL of Millipore water followed by hydration at 60° C. for ~12 h resulted in dendrosomes incorporating Nile red dye. Dendrosomes were used without further manipulation for visualization using a fluorescence microscope.

Encapsulation of hydrophilic dyes (Calcein excitation/emission 495/515, FITC-Dextran excitation/emission 495/521) follows the same procedure for film hydration, the hydrophilic dye being added in the hydration step into the aqueous solution. The Janus-dendrimer dissolved in dichloromethane, THF or diethyl ether (200 µL) at a concentration of 10 mg/mL was deposited on the surface of a roughened Teflon plate within a glass vial. The samples were dried for at least 12 hours under vacuum. 2 mL of ultrapure water containing 50 µM fluorescein isothiocyanate dextran (FITC-Dextran 10,000 MW) or 50 µM calcein were added followed by hydration at 60° C. for 7-12 h. The excess of non-encapsulated dye was removed by passing the sample through a Sephadex G25 (Sigma) column (~1.5 cm×10 cm) with 2 cm layer of QAE Sepharose A50 (Pharmacia) anion-exchange resin at the bottom using citrate phosphate buffer (pH=7.2) as eluent. Most of the dye was excluded by gel-filtration on Sephadex, while the resin retained the remaining dye. Dialysis can also be used to eliminate the non-encapsulated dye. Dendrosomes were used without further manipulation.

Incorporation of Both Hydrophobic and Hydrophilic Dyes a. 200 µL (10 mg/mL Janus-dendrimer, 0.1 mg/mL Nile Red solution in methylene chloride, THF, or diethyl ether) of Janus-dendrimer solution were evenly deposited on the surface of a roughened Teflon plate and placed in a vial followed by evaporation of the solvent for 12 h. Addition of aqueous solution containing 50 µM fluorescein isothiocyanate Dextran (10,000 MW, excitation/emission 495/521), followed by hydration at 60° C. for 12 h led to formation of dendrosomes. Dendrosomes were purified on a Sephadex G25 (Sigma) column (~1.5 cm×10 cm) with 2 cm layer of QAE Sepharose A50 (Pharmacia) anion-exchange resin at the bottom using citrate phosphate buffer as eluent. Most of the excess dye was retained on the Sephadex, while the anion-exchange resin absorbed the remaining non-encapsulated dye. Dendrosomes were used without further manipulation.

b. Incorporation of both hydrophilic and hydrophobic dye was made by film hydration were films were obtained as described above (200 µL of 10 mg/ml solution and 10 µM Nile red dissolved in suitable solvent and deposited on the Teflon film and dried for 12 h) After drying under vacuum, the films were hydrated with aqueous solution containing 10 µM calcein solution in 270 mM sucrose. Following hydration, dendrosomes incorporating both dyes were isolated by repeated centrifugation washing cycles. Giant unilamelar dendrosomes were visualized by fluoresence microscopy using filters specific for Nile red (excitation/emission 485/525) and Calcein (excitation/emission 495/515).

Dendrosome Formation from Different Solvents by Injection Method

The Janus-dendrosome (0.5 mg) dissolved in 100 µL of solvent was injected into 1 mL of ultrapure water followed by 5 seconds of vortex mixing. DLS experiments were performed at 25° C. within 5 min from preparation. Dendrosomes were obtained from all ethanol, acetone, THF, acetonitrile, dioxane and DMSO, with sizes ranging from 108-270 nm and PDI of 0.1-0.23. Ethanol, acetone, acetonitrile and DMSO produced monomodal number distributions, however dendrosomes formed by dioxane exhibited a bimodal distribution indicating the coexistence of dendrosomes with smaller objects.

Stability of Dendrosomes in Time

Dendrosomes were formed according to the general injection method disclosed herein at a final concentration 0.5 mg/mL. DLS measurements were performed and the sample was transferred into a screw top vial and stored at 25° C. Dendrosomes from libraries 1, 2 and 11 generally showed good stability in time at physiological pH (pH=7.4). In some cases, measurements showed constant size up to 244 days.

Stability of Dendrosomes in Buffer

Dendrosomes were formed by injection of ethanol Janus-dendrimer solution into phosphate saline buffer (PBS, pH=7.4). DLS measurements were performed immediately after the injection and after 60 min of equilibration. Injection of ethanol solutions of Janus-dendrimers from Library 1 showed poor stability in PBS buffer generating large particles that agglomerate dropping out of solution after 30 min from injection. Library 2 of amphiphilic Janus-dendrimers formed stable dendrosomes in both citrate and phosphate buffer stable over a period of 2-3 weeks.

Dendrosome Formation from Different Solvents by Injection Method

The Janus-dendrosome (0.5 mg) dissolved in 100 µL of solvent was injected into 1 mL of ultrapure water followed by 5 seconds of vortex mixing. DLS experiments were performed at 25° C. within 5 min from preparation. Dendrosomes were obtained from all ethanol, acetone, THF, acetonitrile, dioxane and DMSO, with sizes ranging from 108-270 nm and PDI of 0.1-0.23. Ethanol, acetone, acetonitrile and DMSO produced monomodal number distributions, however dendrosomes formed by dioxane exhibited a bimodal distribution indicating the coexistence of dendrosomes with smaller objects.

Concentration Dependence of Size and Polydispersity of Dendrosomes Formed via Ethanol Injection Method Dendrosomes were formed according to the general method discussed herein at final concentrations from 0.5-20 mg/mL. DLS measurements were carried out immediately following injection and repeated after 60 min. Janus dendrimer $(3,5)12G1$-PE-BMPA-$(OH)_8$ at concentrations of 0.5-10 mg/mL resulted in sizes from 94-330 nm and PDI from 0.04-0.018. Monomodal distributions were obtained from 0.5-7 mg/mL and bimodal distributions from 10-20 mg/mL. Concentration of 20 mg/mL exhibited sizes of 1004 nm and PDI of 0.4 the sample exhibited increased turbity and flocculation of particles over 20 min. Janus-dendrimer $(3,4)12G1$-PE-BMPA-$(OH)_8$ at concentrations of 0.5-2 mg/mL exhibit unimodal distributions of sizes from 111-175 nm and PDI of 0.07-0.2. At concentrations over 3 mg/mL, multimodal size distributions and increased flocculation in time was observed.

Sizes and Size Distribution of Dendrosomes from Library 1 and 2 Spontaneously Formed by Ethanol Injection Method Dendrosomes were formed according to the general method discussed herein at final concentrations of 0.5 mg/mL aqueous solution. With the exception of a few compounds most compounds exhibited unimodal size distributions and PDI between 0.02 and 0.2. The low values of polydispersity demonstrate the formation of monodisperse dendrosomes.

Mechanical Properties

The elastic properties of dendrosome membranes were determined by micropipette aspiration following an analogous procedure described previously (Needham, Biophys. J. 58, 997-1009 (1990)). Giant unilamellar (~20 m diameter) dendrosomes were prepared by Teflon film hydration as described herein and dispersed into iso-osmotic ultrapure water. Glass micropipettes with inner diameter from ~3 μm to ~10 μm were filled with iso-osmotic ultrapure water and connected to an aspiration station mounted on the side of a Zeiss inverted microscope, equipped with a manometer. The pipettes were used to manipulate the dendrosomes and to apply well-defined stress to the wall by inducing suction tension on their membranes.

The micropipette suction pressure is controlled in the range of microatmospheres and tenths of atmospheres (0.1 $N/m^2$ to 10000 $N/m^2$). The tension results in deformation and consequently provides direct measurements of the elastic moduli, which characterizes the membrane area expansion and bending, together with other parameter that characterize the tensile failure of the vesicle membrane according to the equations (1) and (2):

$$K_a = \Delta\tau/\Delta\alpha \quad (1)$$

$$E_s = Ka(\alpha_c)^2/2 \quad (2)$$

were $K_a$=elastic area expansion modulus; $\Delta\tau$=fractional tension; $\tau_s$=membrane tension at failure; $\Delta\alpha$=fractional increase in membrane area; $\alpha_c$=critical areal strain-fractional increase in membrane area at failure, and $E_s$=energy stored at failure Results are presented in the Table below.

Mechanical properties of dendrosomes and comparison with polymersomes and liposomes

| Sample | | $K_a$ (mN/m) | Lysis Tension $\tau_s$ (mN/m) | Critical $\alpha_c$ | Energy stored at failure (mJ/m²) |
|---|---|---|---|---|---|
| Dendrosomes | (3,4)12G1-PE-BMPA-$(OH)_8$ | 961 | 20.4 | 0.04 | 0.42 |
| | (3,5)12G1-PE-BMPA-$(OH)_8$ | 976 | 15.5 | 0.03 | 0.69 |
| | (3,4,5)12G1-PE-BMPA-$(OH)_8$ | 42.44 | 0.88 | 0.06 | 0.11 |
| | (3,4,5)12G1-PE-(3,4,5)-3EO-G1-$(OH)_6$ | 267.5 | 12.7 | 0.04 | 0.27 |
| | (3,5)12G1-PE-(3,4)-3EO-G1-$(OH)_4$ | 582.5 | 15.11 | 0.06 | 0.73 |
| Polymersomes[16] | $OB_2$ (PEO-PBD) | 100 | 14.0 | 0.21 | |
| | $OE_7$ (PEO-PEE) | 140 | 18.0 | 0.19 | 2.20 |
| | $OB_{18}$ (PEO-PEB) | 109 | 33.0 | 0.40 | |
| Lipids | DAPC | 57 | 2.3 | 0.04 | |
| | Egg PC | 140 | 4.0 | | |
| | DMPC | 234 | | | |
| | SOPC/ % Cholesterol[87] | 193 | 5.7 | 0.03 | 0.10 |
| | 0% | 244 | 12.6 | 0.05 | 0.33 |
| | 28% | 781 | 19.7 | 0.03 | 0.34 |
| | 50% | 1286 | 28.0 | 0.02 | 0.31 |
| | 78% | | | | |

Miscibility of Janus-Dendrimers with Phospholipids Forming Liposomes and Block-copolymer Forming Polymersomes Miscibility of several examples of Janus-dendrimers from libraries 1 and 10 with either SOPC (1-Stearoyl-2-Oleoyl-Sn-Glycero-3-Phosphatidylcholine) phospholipid forming liposomes or block copolymers OB-29 (poly(1,2 butadiene)-b-poly(ethylene oxide) (Mw=3800 g/mol; fEO=0.34) forming polymersomes was investigated by microscopy and DSC. Giant dendrosomes were obtained by film hydration as described herein where the Janus dendrimer: SOPC and/or OB29 were dissolved in a 1:1(:1) ratio followed by deposition on 1 $cm^2$ Teflon and hydration with Millipore water or PBS phosphate buffer (pH=7.2). The miscibility of (3,5) 12G1-PE-BMPA-$(OH)_8$ Janus-dendrimer from Library 1 with SOPC was investigated and confirmed by DSC.

Dendrosomes Tagged with Fluorescent Dye

The design of dendrosomes allows easy functionalization of the hydrophilic or hydrophobic segment with a variety of functionalities such as dyes, contrast agents, targeting molecules or drugs. As a proof of this concept the hydrophilic segment of two Janus-dendrimers was functionalized with fluorescent dyes giving rise to tagged compounds. See, the scheme below. The labeled Janus-dendrimers can be mixed with non-labeled Janus-dendrimers, phospholipids or block copolymers in various ratios. For example, a 1% ratio was used for visualization of giant dendrosomes under microscope

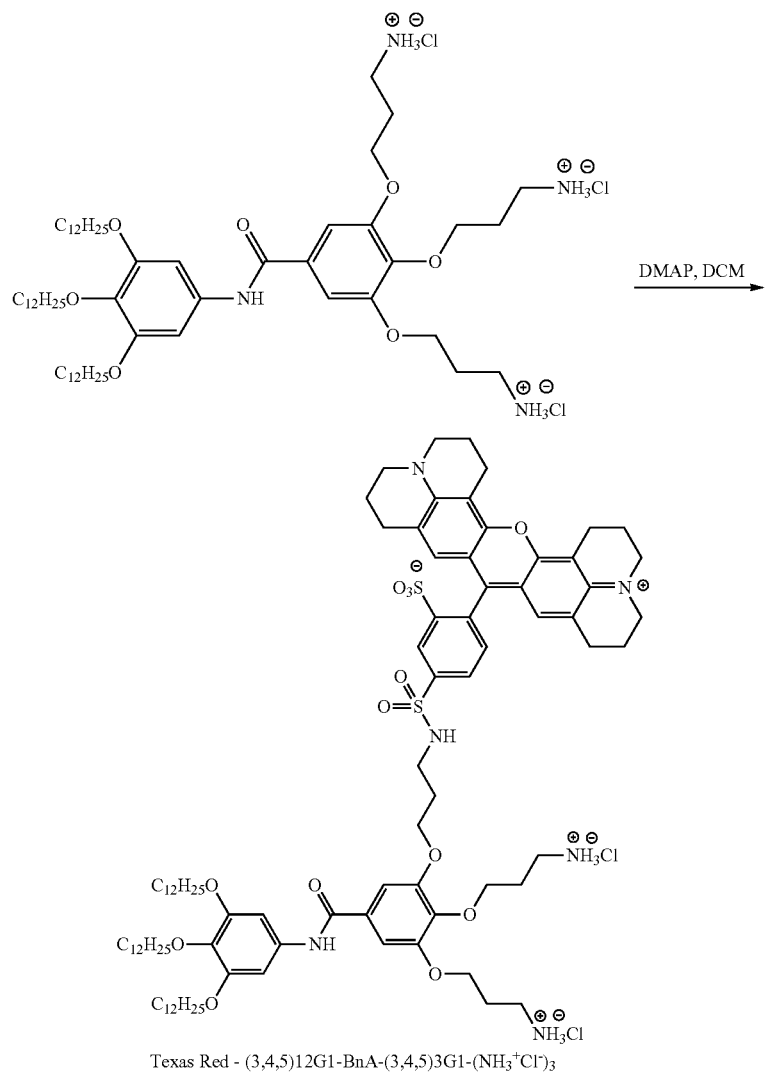
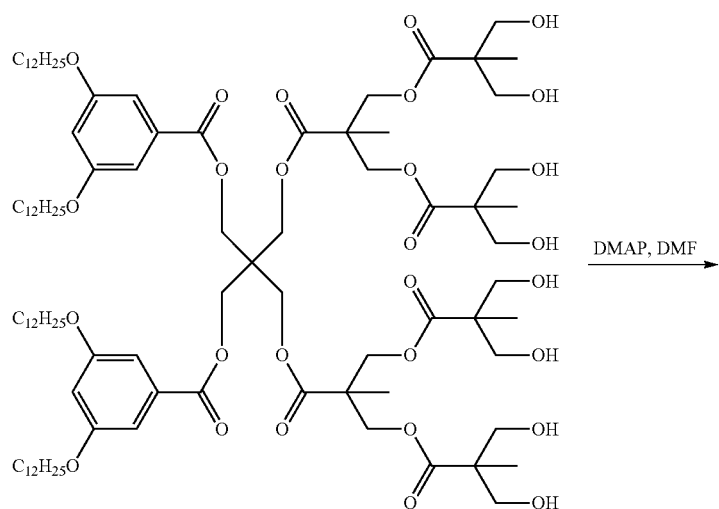

-continued

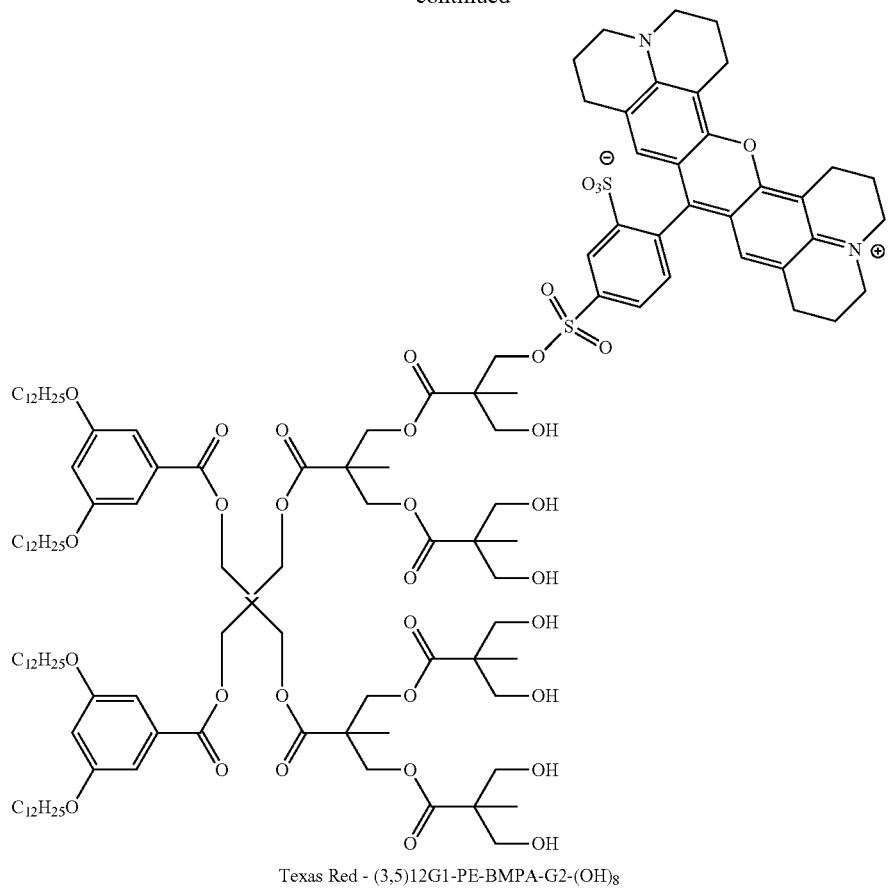

Texas Red - (3,5)12G1-PE-BMPA-G2-(OH)₈

Melittin Pore Formation in Dendrosomes

Melittin is known to form pores when mixed with SOPC liposomes. Pore formation by incorporation of Melittin into dendrosomes was investigated after injection of mellitin over Library 1 dendrosome and phospholipid SOPC control liposomes formed by standard film hydration. Fluorescent dye ANTS and the quencher DPX known to quench at high concentrations when encapsulated were used for the study. Following addition of Melittin, a dramatic increase in ANTS fluorescence was observed which is associated with the release of the dye on pore formation. Lysis of the dendrosomes with Triton-X allowed a subsequent determination of dye release following Melittin incorporation. SOPC liposomes and dendrosomes encapsulating fluorescent dyes were prepared as described herein. Janus-dendrimer or SOPC (2 mg) were dissolved in 2 mL of methylene chloride, THF, or diethyl ether in a 10 mL flask. The solvent was slowly evaporated under nitrogen flow, making sure the lipid layer was uniformly dispersed on the flask walls. The residue was dried in vacuum for 12 h at 20° C. The aqueous solution containing 2 mL of 25 mM ANTS fluorescent dye and 25 mM DPX quencher was added to the flask and the lipid was left to hydrate for 2-48 h at 70° C. This was followed by three freeze-thaw cycles and subsequent heating, and sonication. Liposomes were extruded twenty one times using 100 nm polycarbonate membranes.

The non-encapsulated dye was removed on a Sephadex G25 (Sigma) column (~1.5 cm×10 cm) with 2 cm layer of QAE Sepharose A50 (Pharmacia) anion-exchange resin at the bottom using citrate-phosphate buffer as eluent (pH=7.2). Most of the dye was excluded by gel-filtration on Sephadex, while the resin retained the remaining ANTS/DPX. Liposomes were used without further manipulation.

Release studies of ANTS/DPX from the loaded dendrosomes were analyzed immediately following dilution in citrate-phosphate buffer. ANTS fluorescence was measured fluorometrically ($\lambda_{ex}$=360 nm, $\lambda_{em}$=530 nm) before and after injection of 63 μL of Melittin (300 μM) in water into 2 mL of dendrosome suspension. As ANTS was released from the dendrosome core, and diluted into the surrounding solution, its fluorescence emission increased over time. At the end of the study, the samples were lysed using Triton X-100. The addition of Triton X cause the rupture of the liposomes, a release of the encapsulated dye, and consequently an increase in the fluorescence emission as the ANTS is diluted below the quenching concentration. The percent of dye release over time was calculated as the ratio between the fluorescence measured at each time point to the final ANTS fluorescence obtained upon lysis.

Dendrosomes and liposomes obtained by film hydration with Millipore water were analyzed by circular dichroism (CD). Melittin (63 μL, 300 μM) in water were added into 2 mL of dendrosome suspension and the solution was analyzed immediately. Both SOPC liposomes and (3,5)12G1-PE-BMPA-(OH)₈ dendrosomes showed CD signal due to the self-assembly of the chiral melittin inside the pore.

Doxorubicin Drug Encapsulation and Release

Doxorubicin encapsulation into small unilamellar vesicle was carried out by hydration of Janus-dendrimer films with doxorubicin/ammonium sulphate aqueous solution.[97,98,99]

Small unilamellar dendrosomes were obtained as described herein: 200 μL of a 10 mg/mL Janus-dendrimer solution in methylene chloride were uniformly deposited on the surface of a roughened Teflon plate followed by evaporation of the solvent for over 12 h. Addition of the aqueous solution containing ~290 mOsm ammonium sulfate solution and doxorubicin (DOX) (0.2 mg/mL) at pH 7.4, followed by sonication led to spontaneous formation of drug encapsulated nanosized dendrosomes. Equilibration of the aqueous solution (Branson; Model 3510) at 60-65° C. for 30 min was followed by sonication for 60 min at 60-65° C. and five freeze-thaw cycles (freezing in liquid N2 and subsequently thawing in a water bath at 50-60° C.).

After hydration and sonication the solution of dendrosomes was removed from the vials and introduced into dialysis cassettes for removal of the non-encapsulated drug. Dendrosomes were dialyzed at 4° C. in iso-osmotic citrate phosphate buffer (pH~7.4) for 3 days while dialysis solution was changed 4 times over approximately 48 hours. Following dialysis, the samples were removed from cassettes, and diluted in the citrate phosphate buffer. Release measurements of DOX from the loaded dendrosomes were performed immediately following the dilution step. Doxorubicin fluorescence was measured fluorometrically (using a SPEX Fluorolog-3 fluorimeter; $\lambda_{ex}$=480 nm, $\lambda_{em}$=590 nm) at various intervals over 4 days. The fluorescence was recorded at time zero for all samples. Subsequently, a portion of the samples were acidified with 12.1N HCl to bring the pH down to approximately 5.2 and the fluorescence was re-measured, while the new fluorescence was considered time zero for the acidified samples. Inside the dendrosomes the DOX is aggregated and its fluorescence is quenched. As DOX was released from the dendrosomes and diluted into the surrounding solution, its fluorescence emission increased over time. At the culmination of the study, the dendrosomes were lyzed using Triton X-100 and at a temperature of 50° C. The percent of Dox release over time was calculated as the ratio between the fluorescence measured at each time point to the maximum final fluorescence obtained upon lysis with TritonX-100 according to the equation:

$$P\% = (It - It_0)/(Imax(Tx) - It_0) \times 100, \text{ where}$$

It=fluorescence at each time point t
$It_0$=fluorescence at time point 0
Imax(Tx)=maximum fluorescence upon lysis with Triton X Cell Viability and Dendrosomes Toxicity Evaluation Since endothelial cells are the first point of contact for intravenous drug formulations, the toxicity of the dendrosomes was evaluated in vitro on human umbilical vein endothelial cells (HUVECs). HUVECs were cultured in EGM Endothelial Growth Media (LONZA) supplemented with bovine brain extract (BBE) with heparin, h-EGF, hydrocortisone, gentamicin, amphotericin B (GA-1000), and fetal bovine serum (FBS). Cells were maintained in plastic culture flasks at 37° C. in a humidified atmosphere containing 5% $CO_2$ and were further subcultured when the flasks were 70% to 90% confluent. The passage number of the cells for the HUVECs in vitro studies was 5-8. The investigation of toxicity of dendrosomes and viability of the cells was assessed fluorometrically by determining the number of viable cells present in multiwell plates. Cell viability was determined using the indicator dye resazurin, which is reduced by viable cells to a highly fluorescent form resorufin according to Scheme S17. In this way the viable cells retain the metabolic capacity and can be directly monitored while nonviable cells rapidly lose metabolic capacity, are not able to reduce the indicator dye and as such do not generate a fluorescent signal. The CellTiter-Blue Cell Viability Assay was obtained from Promega.

Scheme S17. Reduction of resazurin to the highly fluorescent form resorufin in the presence of life cells

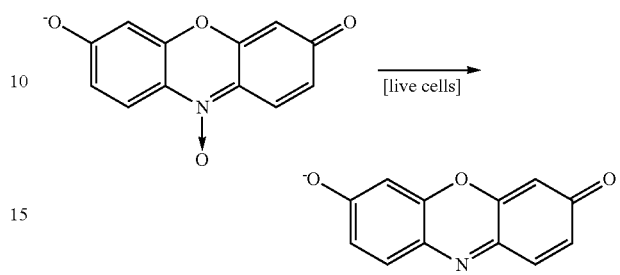

HUVECs were plated at a density of 3,200 cells per well (10,000 cells/cm$^2$) in 96 well tissue culture plates and allowed to adhere overnight. Culture media was removed from the wells and replaced with 250 μL of either: 100% media, 94% media/6% PBS buffer, 87.5% media/12.5% PBS buffer, 75% media/25% PBS buffer, 100% PBS buffer, and various concentrations of sterile dendrosomes and polymersomes ranging from 0.25 mg to 0.0625 mg in the three concentrations of media/PBS, and maintained at 37° C. in a humidified atmosphere of 5% $CO_2$. The dendrosomes and polymersomes were prepared by film the hydration method as described in section S5.1 and extruded 25 times through 100 nm polycarbonate membrane. Dendrosomes and polymersomes were sterilized by exposing them for # min to UV irradiation. At various defined time points (1 h, 2 h, and 4 h post vesicle administration), wells were washed three times with 250 μL of PBS and 100 μL of fresh media was added. To the fresh media, 20 μL of Cell-Titer Blue from Promega was added and cells were incubated at 37° C. in a humidified atmosphere containing 5% $CO_2$ for 2 hours. Subsequently, 100 μL of media containing Cell-Titer Blue was removed from the cells and placed in the wells of a 96 well black bottom plate. The fluorescence intensity at 590 nm emanating from the wells when excited at 560 nm was then determined using a TECAN Inifinite2000 plate reader.

What is claimed:
1. An amphiphilic Janus dendrimer having of the formula:

$(X)_t$-A-$(Y)_z$ wherein:
each t and z is independently an integer from 1-6;
A is

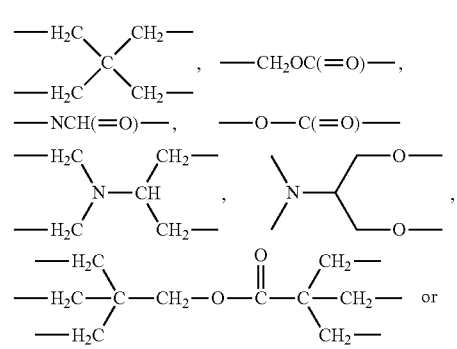

-continued

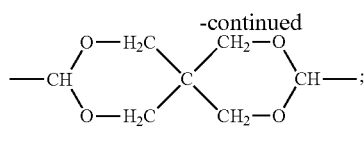

each X is independently selected from:

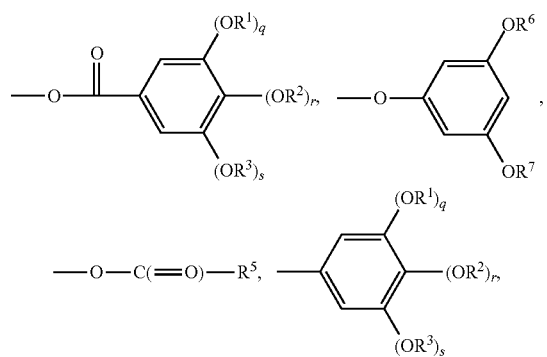

and —O—[CH$_2$—CH(OH)—CH$_2$—O—]$_m$—H; or —C(OR$^5$)$_3$;

wherein R$^1$, R$^2$, R$^3$, R$^5$, R$^6$, R$^7$, are each, independently, C$_1$-C$_{30}$ alkyl, —O(CH$_2$)$_p$R$^{13}$, or —(CH$_2$)$_p$R$^{12}$;

each R$^{12}$ is, independently, H or C$_1$-C$_{30}$ alkyl;

R$^{13}$ is —NHBoc;

m and p are each, independently, an integer from 1 to 12;

each q, r, and s is 0 or 1 and the sum of q+r+s is at least 2;

each Y is independently selected from

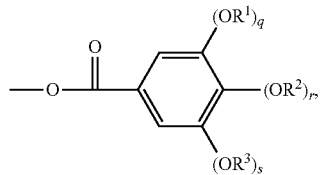

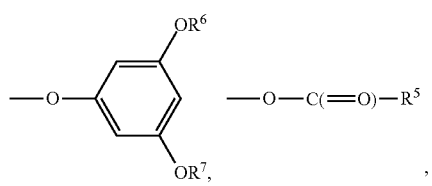

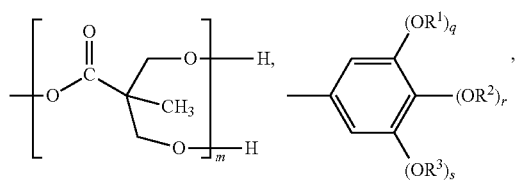

-continued

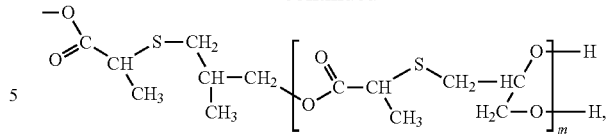

—O—[CH$_2$—CH(OH)—CH$_2$—O—]$_m$—H; or —C(OR$^5$)$_3$;

R$^1$, R$^2$, R$^3$, R$^6$, and R$^7$ are each, independently, —(CH$_2$CH$_2$O)$_m$—R$^4$ or —[CH$_2$CH(OH)CH$_2$O]$_n$H, each R$^4$ is independently R$^5$ or H;

each R$^5$ is independently H or C$_1$-C$_{30}$ alkyl;

m and n are each, independently, an integer from 1 to 12; and each q, r, and s is 0 or 1 and the sum of q+r+s is at least 2;

provided that when X is

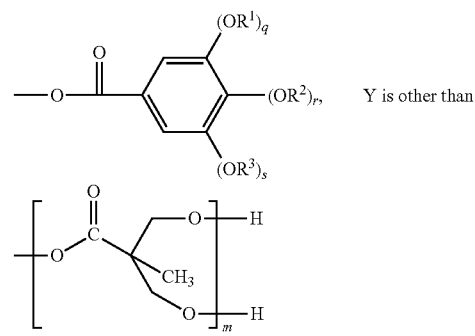

Y is other than wherein when A is —CH$_2$OC(=O)—, —NHC(=O)— or —O—C(=O)—, at least one of (a) X is

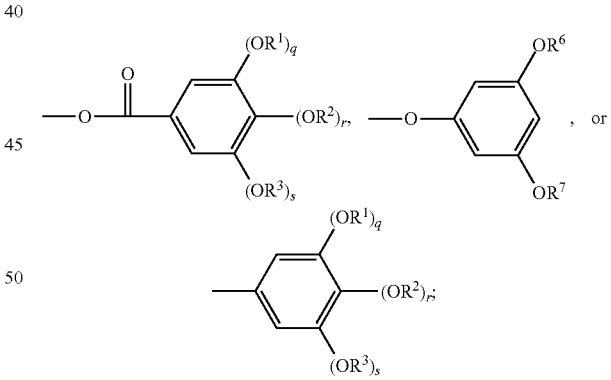

or (b) Y is

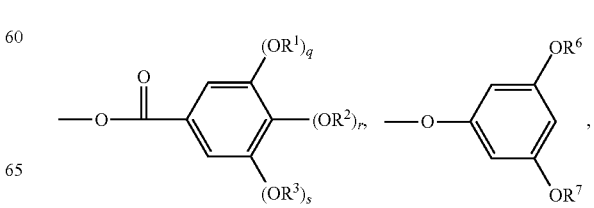

-continued

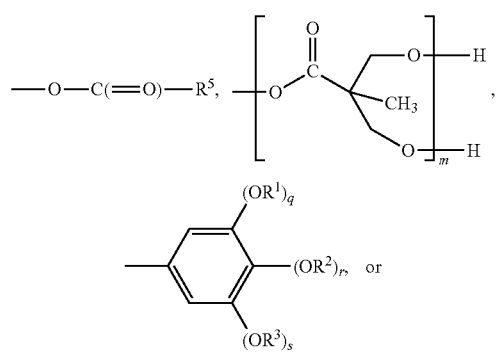

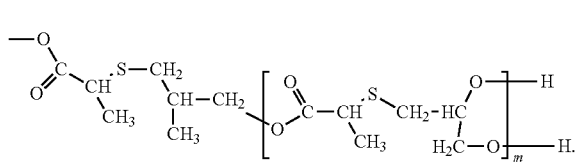

2. The amphiphilic Janus dendrimer of claim 1 having the formula:

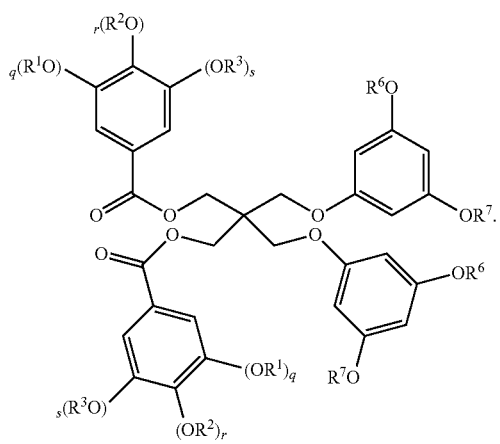

3. The amphiphilic Janus dendrimer of claim 1 having the formula:

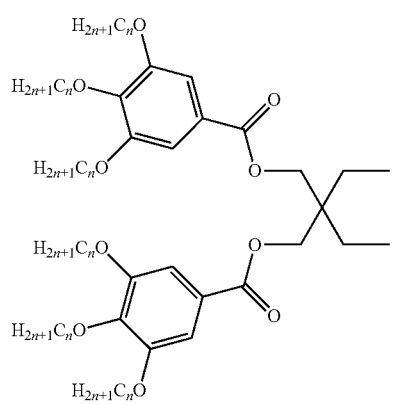

-continued

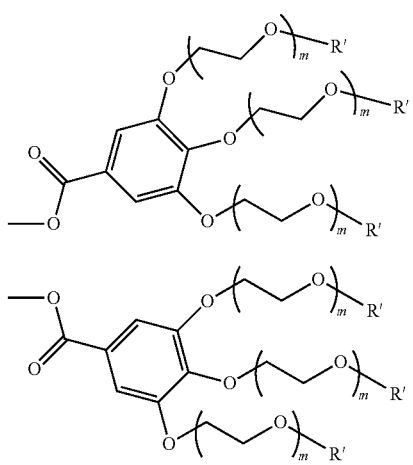

wherein R' is OH or OCH$_3$.

4. The amphiphilic Janus dendrimer of claim 3:
wherein m is an integer from 1 to 6.

5. The amphiphilic Janus dendrimer of claim 1 having the formula:

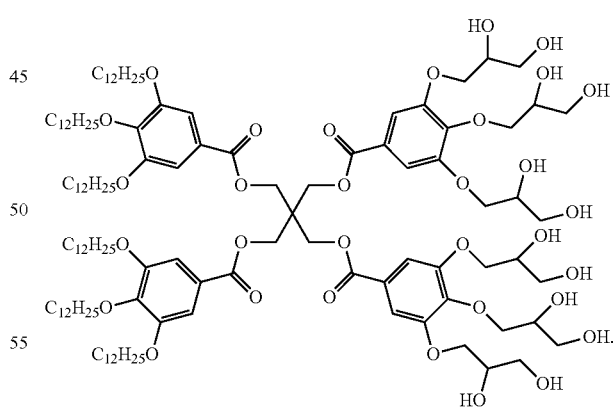

6. The amphiphilic Janus dendrimer of claim 1 having the formula:

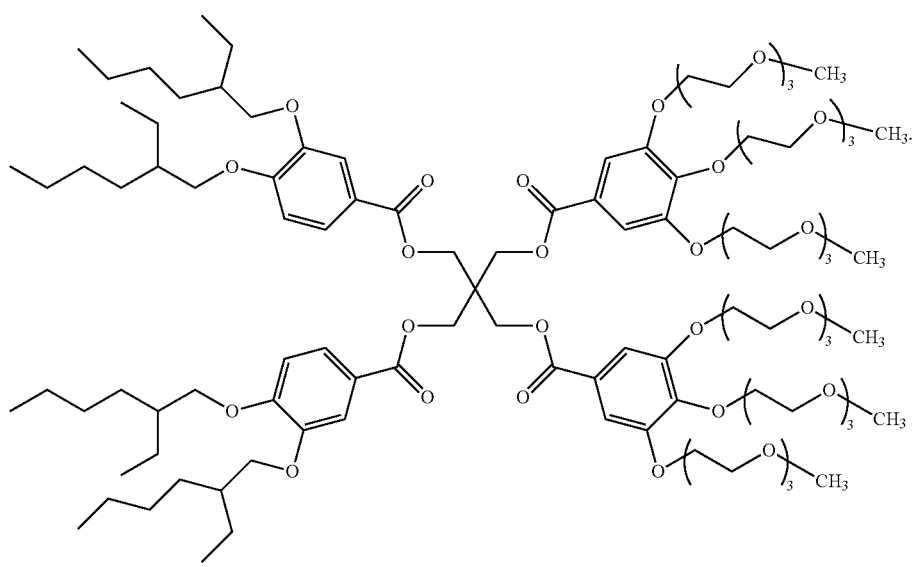
7. The amphiphilic Janus dendrimer of claim 1 having the formula:
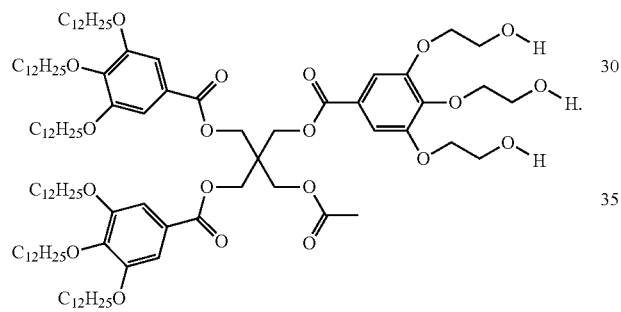
8. The amphiphilic Janus dendrimer of claim 1 having the formula:
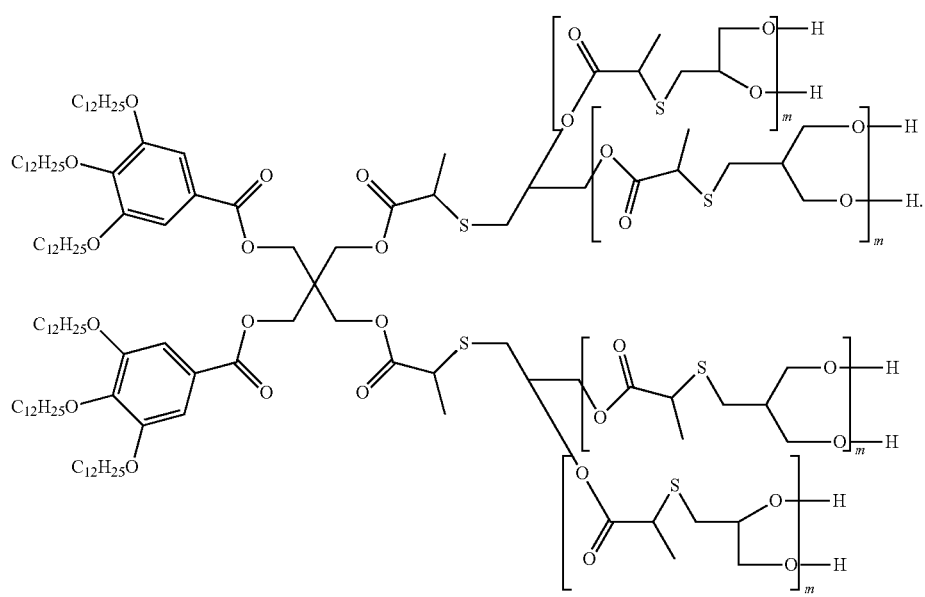

9. The amphiphilic Janus dendrimer of claim 8, wherein m is an integer from 1 to 6.

10. The amphiphilic Janus dendrimer of claim 1 having the formula:

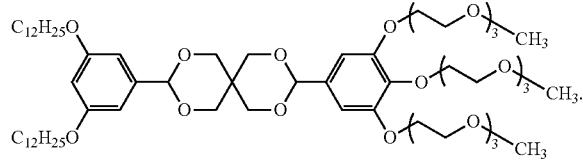

11. The amphiphilic Janus dendrimer of claim 1 having the formula:

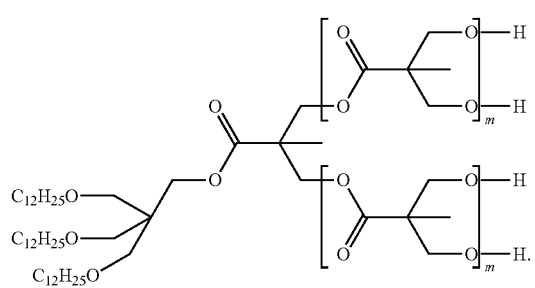

12. The amphiphilic Janus dendrimer of claim 11, wherein m is an integer from 1 to 6.

13. The amphiphilic Janus dendrimer having the formula:

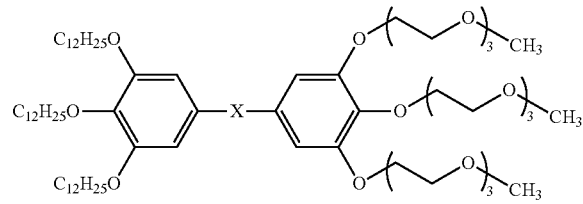

wherein X is —CH$_2$—NH—CO— or —NH—CO—; or

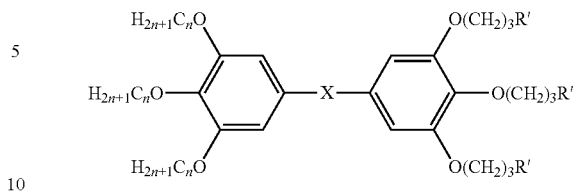

wherein X is —CH$_2$—NH—CO— or —NH—CO—; R' is —NHBoc or —NH$_3^+$Cl$^-$.

14. The amphiphilic Janus dendrimer of claim 1, wherein n is 4 or 12.

15. The amphiphilic Janus dendrimer of claim 1 having the formula:

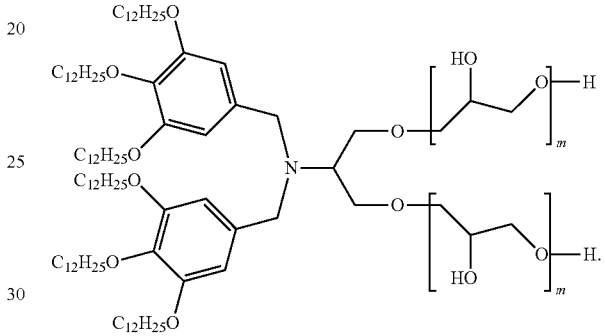

16. A liposome comprising a plurality of amphiphilic Janus dendrimers of claim 1.

17. A method of forming a liposome comprising contacting a mixture of an alcohol and a plurality of amphiphilic Janus dendrimer of claim 1 with water.

18. The method of claim 17, wherein the alcohol is ethanol.

19. A method of delivery of a therapeutic composition comprising contacting a liposome comprising a plurality of amphiphilic Janus dendrimers of claim 1 and said therapeutic composition with a mammal under conditions effective to deliver said liposome to a cell or tissue within said mammal.

20. The method of claim 19, wherein said mammal is a human.

* * * * *